(12) United States Patent
Palka-Hamblin et al.

(10) Patent No.: US 7,205,121 B2
(45) Date of Patent: Apr. 17, 2007

(54) DEP-1 RECEPTOR PROTEIN TYROSINE PHOSPHATASE INTERACTING PROTEINS AND RELATED METHODS

(75) Inventors: Helena L. Palka-Hamblin, Chicago, IL (US); Nicholas K. Tonks, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 453 days.

(21) Appl. No.: 10/723,606

(22) Filed: Nov. 26, 2003

(65) Prior Publication Data

US 2004/0161821 A1    Aug. 19, 2004

Related U.S. Application Data

(60) Provisional application No. 60/429,746, filed on Nov. 26, 2002.

(51) Int. Cl.
*C12Q 1/42* (2006.01)
*C12N 9/16* (2006.01)
*C07H 21/04* (2006.01)

(52) U.S. Cl. .................. 435/21; 435/196; 536/23.2

(58) Field of Classification Search .............. 435/21, 435/196, 23.2
See application file for complete search history.

(56) References Cited

U.S. PATENT DOCUMENTS

| 5,912,138 A | 6/1999 | Tonks et al. ............ 435/21 |
| 5,951,979 A | 9/1999 | Tonks et al. ............ 424/94.6 |
| 6,114,140 A | 9/2000 | Tonks et al. ............ 435/69.1 |
| 6,552,169 B1 | 4/2003 | Tonks et al. ............ 530/350 |
| 2003/0148491 A1 | 8/2003 | Tonks et al. ............ 435/196 |

FOREIGN PATENT DOCUMENTS

| WO | WO 95/30008 | 11/1995 |
| WO | WO 98/04712 | 2/1998 |
| WO | WO 00/75339 A1 | 12/2000 |

OTHER PUBLICATIONS

Baker, J. et al., "Protein Tyrosine Phosphate CD148-Mediated Inhibition of T-Cell Receptor Signal Transduction is Associated with Reduced LAT and Phospholipase Cγ1 Phosphorylation," *Mol Cell Biol. 21* (7):2393-403, Apr. 2001.

Bardelli, A. et al., "Gab1 Coupling to the HGF/Met receptor Multifunctional Docking Site Requires Binding of Grb2 and Correlates with the Transforming Potential," *Oncogene 15*(25):3103-11, Dec. 1997.

Barford, D. et al., "The Structure and Mechanism of Protein Phosphatases: Insights Into Catalysis and Regulation," *Annu Rev Biophys Biomol Struct. 27*:133-64, 1998.

Barnea, G. et al., "Idnetification of a Carbonic Anyhydrase-Like Domain in the Extracellular Region of RPTPγ Defines a New Subfamily of Receptor Tyrosine Phosphatases," *Mol. Cell. Biol.13* (3):1497-1506, Mar. 1993.

Ben-Ze'ev, A. et al., "The Integration of Cell Adhesion with Gene Expression: The Role of β-Catenin," *Exp Cell Res. 261*(1):75-82, Nov. 2000.

Borges, L. et al., "Cloning and Characterization of Rat Density-Enhanced Phosphatase-1, A Protein Tryosine Phosphatase Expressed by Vascular Cells," *Circ Res. 79*(3):570-80, Sep. 1996.

Bork, P. et al., "Proposed Acquisition of an Animal Protein Domain by Bacteria," *Proc. Natl. Acad. Sci. USA 89*:8990-8994, 1992.

Brady-Kalnay, S. et al., "Homophilic Binding of a PTPμ, a Receptor-Type Protein Phosphatase, Can Mediate Cell-Cell Aggregation," *J. Cell Biol. 122*:961-972, 1993.

Brown-Shimer, S. et al., "Effect of Protein Tyrosine Phosphatase 1B Expression on Transformation by the Human *neu* Oncogene," *Cancer Res. 52*;478-482, Jan. 1992.

Buzzi, M. et al., "Differentiation-Induced Changes in Protein-Tyrosine Phosphatase Activity and Commensurate Epxression of CD45 in Human Leukemia Cell Lines," *Cancer Res. 52*:4027-4035, Jul. 1992.

Capecchi, M.R., "Altering the Genome by Homologous Recombination," *Science 244*:1288-1292, Jun. 1989.

Carr, D. et al., "Blotting and Bandshifting: Techniques for Studying Protein-Protein Interactions," *Trends in Biochemical Sci. 17*246-249, Jul. 1992.

Carr, D. et al., "Association of the Type II cAMP-dependent Protein Kinase with a Human Thyroid RII-Anchoring Protein," *J. Biol. Chem. 267*(19):13376-13382, Jul. 1992.

Charbonneau, H. et al., "1002 Protein Phosphatases," *Ann. Rev. Cell Biol. 8*:463-493, 1992.

Conacci-Sorrell, M. et al., "The Cadherin-Catenin Adhesion System in Signaling and Cancer," *J Clin Invest. 109*(8):987-91, Apr. 2002.

Cool, D. et al., "cDNA Isolated from a Human T-Cell Library Encodes a Member of the Protein-Tyrosine-Phosphatase Family," *Proc. Natl. Acad. Sci. USA 86*:5257-5261, 1989.

Edelman G. et al., "Cell Adhesion Molecules: Implications for a Molecular Histology," *Ann Rev. Biochem. 60*:155-190, 1991.

Fields S. et al., "A Novel Genetic System to Detech Protein-Protein Interactions," *Nature 340*:245-246, Jul. 1989.

(Continued)

*Primary Examiner*—Tekchand Saidha
(74) *Attorney, Agent, or Firm*—Seed IP Law Group PLLC

(57) ABSTRACT

Proteins are identified from human breast tumor cell lines (MDA-MB-231, T-47D and T-47D/Met) that interact specifically with the substrate-trapping mutant form of Density Enhanced Phosphatase-1 (DEP-1). These proteins include the functional component p120 catenin (p120$^{ctn}$), the adaptor protein Gab 1, and the HGF/SF receptor Met. The invention relates to isolated complexes comprising DEP-1 polypeptides in specific association with Met, Gab 1, or p120$^{ctn}$, identified herein as DEP-1 substrate polypeptides. Screening assays for agents that alter DEP-1 interaction with DEP-1 substrate polypeptides are also disclosed, as are methods for altering biological signals in cells that are transduced via DEP-1 pathways.

8 Claims, 5 Drawing Sheets

OTHER PUBLICATIONS

Fischer, E. et al., "Protein Tyrosine Phosphatases: A Diverse Family of Intracellular and Transmembrane Enzymes," *Science* 253:401-406, Jul. 1991.

Fixman, E. et al., "Efficient Cell Transformation by the Tpr-Met Oncoprotein is Dependent Upon Tyrosine 489 in the Carboxy-Terminus," *Oncogene* 10(2):237-49, Jan. 1995.

Flint, A. et al., "Multi-site Phosphorylation of the Protein Tyrosine Phosphatase, PTPIB: Identification of Cell Cycle Regulated and Phorbol Ester Stimulated Sites of Phosphorylation," *EMBO J.* 12(5):1937-1946, May 1993.

Flint, A. et al., "Development of 'substrate-trapping' mutants to identify physiological substrates of protein tyrosine phosphatases," *Proc Natl Acad Sci U S A.* 94(5):1680-5, Mar. 1997.

Florio, T. et al., "Oncogene Transformation of PC C13 Clonal Thyroid Cell Line Induces an Autonomous Pattern of Proliferation that Correlates with a Loss of Basal and Stimulated Phosphotyrosine Phosphatase Activity," *Endocrionology* 138(9):3756-63, Sep. 1997.

Fournier, T. et al., Branching Tubulogenesis but not Scatter of Madin-Darby Canine Kidney Cells Requires a Functional Grb2 Binding site in the Met Receptor Tyrosine Kinase, *J Biol Chem.* 271(36):22211-7, Sep. 1996.

Frangioni, J. et al., "The Nontransmembrani Tyrosine Phosphatase PTP-B1 Lacalizes to the Endoplasmic Reticulum via its 35 Amino Acid C-Terminal Sequence," *Cell* 68:545-560, Feb. 1992.

Furge, K. et al., "Met Receptor Tyrosine Kinase: Enhanced Signaling Through Adapter Proteins," *Oncogene* 19(49):5582-9, Nov. 2000.

Gebbink, M. et al., "Cloning, Expression and Chromosomal Localization of a New Putative Receptor-Like Protein Tyrosine Phosphatase," *FEBS Lett.* 290(1,2):123-130, Sep. 1991.

Giordano, S. et al., "The Semaphorin 4D Receptor Controls Invasive Growth by Coupling with Met," *Nat Cell Biol.* 4(9):720-4, Sep. 2002.

Gottardi, C. et al., "E-Cadherin Suppresses Cellular Transformation by Inhibiting β-Catenin Signaling in an Adhesion-Independent Manner." *J Cell Biol.* 153(5):1049-59, May 2001.

Gu, M. et al., "Cloning and Expression of a Cytosolic Megakarycyte Protein-Tyrosine-Phosphatase with a Sequence Homology to Retinaldehyde-Binding Protein and Yeast SEC14p," *Proc. Natl. Acad. Sci. USA* 89:2980-2984, Apr. 1992.

Hirsch, A. et al., "Cloning and Expression of an Intron-less Gene for AKAP 75, an Anchor Protein for the Regulatory Subunit of cAMP-Dependent Protein Kinase IIβ," *J. Biol. Chem.* 267(4):2131-2134, Feb. 1992.

Holsinger, L. et al., "The Transmembrane Receptor Protein Tyrosine Phosphatase DEPI Interacts with p120$^{ctn}$," *Oncogene* 21(46):7067-76, Oct. 2002.

Honda, H. et al., "Identification of Novel Protein-Tyrosine Phosphatases in a Human Leukemia Cell Line, F-36P," *Leukemia* 7(5):742-746, May 1993.

Honda, H. et al., "Molecular Cloning Characterization and Chromosomal Localization of a Novel Protein-Tyrosine Phosphatase HPTPη," *Blood* 84(12):4186-4194, Dec. 1994.

Huynh, T. et al., "Constructing and Screening cDNA Libraries in λgt10 and λgt11," *DNA Cloning* vol. 1, edited by Glover, IRL Press, pp. 49-78, 1985.

Jia, Z., "Protein Phosphatases: Structures and Implications," *Biochem Cell Biol.* 75(1):17-26, 1997.

Keane, M. et al., "The Protein Tyrosine Phosphatase DEP-1 is Induced During Differentiation and Inhibits Growth of Breast Cancer Cells," *Cancer Res.* 56(18):4236-43, Sep. 1996.

Keirsebilck, A. et al., "Molecular Cloning of the Huma p120$^{ctn}$ Catenin Gene (CTNNDI): Expression of Multiple Alternatively Spliced Isoforms.," *Genomics* 50(2):129-46, Jun. 1998.

Klarlund, J., "Transformation of Cells by an Inhibitor of Phosphatases Acting on Phosphotyrosine in Proteins," *Cell* 41(3):707-717, Jul. 1985.

Komada, M. et al., "The Cell Dissociation and Motility Trigered by Scatter Factor/Hepatocyte Growth Factor are Mediated Through the Cytoplasmic Domain of the c-Met Receptor," *Oncogene* 8(9):2381-90, Sep. 1993.

Kovalenko, M. et al., "Site-Selective Dephosphorylation of the Platelet-Derived Growth Factor β-Receptor by the Receptor-Like Protein-Tyrosine Phosphatase DEP-1," *J Biol Chem.* 275(21):16219-26, May 2000.

Kozak, M., "The Scanning Model for the Translation: An Update," *J. Cell Biol.* 108:229-241, Feb. 1989.

Krueger, N. et al., "A Human Transmembrane Protein-Tyrosine-Phosphatase, PTPζ is Expressed in Brain and has an N-terminal Receptor Domain Homologous to Carbonic Anhydrases," *Proc. Notl. Acad. Sci. USA* 89(16):7417-7421, Aug. 1992.

Krueger, N. et al., "Structural Diversity and Evolution of Human Receptor-like Protein Tyrosine Phosphatases," *EMBO J.* 9(10):3241-3252, 1990.

Kuramochi, S. et al., "Molecular Cloning and Characterization of Byp, a Murine Receptor-Type Tyrosine Phosphatase Similar to Human DEP-1," *FEBS Lett.* 378(1):Jan. 7-14, 1996.

Leahy, D. et al., "Structure of a Fibronectin Type III Domain from Tenascin Phased by MAD Analysis of the Selenomethionyl Protein," *Science* 258(5084):987-991, Nov. 1992.

Lock, L. et al., "Identification of an Atypical Grb2 Carboxyl-Terminal SH3 Domain Binding Site in Gab Docking Proteins Reveals Grb2-Dependent and -Independent Recruitment of Gab1 to Receptor Tyrosine Kinases.," *J Biol Chem.* 275(40):31536-45, Oct. 2000.

Longo, F. et al., "Leukocyte Common Antigen-Related Receptor-linked Tyrosine Phosphatase," *J. Biol. Chem.* 268(35):26503-25611, 1993.

Main, A. et al., "The Three Dimensional Structure of the Tenth Type III Module of Fibronectin: An Insight into RGD-Mediated Interactions," *Cell* 71(4):671-678, Nov. 1992.

Maina, F. et al., "Uncoupling of Grb2 from the Met Receptor in Vivo Reveals Complex Roles in Muscle Development.," *Cell* 87(3):531-42, Nov. 1996.

Martelli, M. et al., "Protein Tyrosine Phosphatase-η Expression is Upregulated by the PKA-Dependent and is Downregulated by the PKC-Dependent Pathways in Thyroid Cells," *Exp. Cell Res.* 245(1):195-202, Nov. 1998.

Matozaki, T. et al., "Molecular Cloning of a Human Transmembrane-type Protein Tyrosine Phosphatase and its Expression in Gastrointestinal Cancers," *J. Biol. Chem.* 269(3):2075-2081, 1994.

Maulik, G. et al., "Role of the Hepatocyte Growth Factor Receptor, c-Met, in Oncogenesis and Potential for Therapeutic Inhibition," *Cytokine Growth Factor Rev.* 13(1):41-59, Feb. 2002.

Mikayama, T. et al., "Molecular Cloning and Functional Expression of a cDNA Encoding Glycosylation-Inhibiting Factor," *Proc. Natl. Acad. Sci. USA* 90(21):10056-10060, Nov. 1993.

Nguyen, L. et al., "Assoication of the Multisubstrate Docking Protein Gab1 with the Hepatocyte Growth Factor Receptor Requires a Functional Grb2 Binding Site Involving Tyrosine 1356," *J. Biol. Chem.* 272(33):20811-9, Aug. 1997.

Oon, S. et al., "Alternative Splicing in a Novel Tyrosine Phosphatase Gene (*DPTP4E*) of *Drosophila melanogaster* Generates Two Large Receptor-Like Proteins which Differ in their Carboxyl Termini," *J. Biol. Chem.* 268(32):23964-23971, 1993.

Osborne, J. et al., "Murine DEP-1, A Receptor Protein Tyrosine Phosphatase, is Expressed in Macrophages and is Regulated by CSF-1 and LPS," *J. Leukoc. Biol.* 64(5):692-701, Nov. 1998.

Ostman, A. et al., "Expression of DEP-1, A Receptor-Like Protein-Tyrosine-Phosphatase, is Enhanced with Increasing Cell Density," *Proc. Natl. Acad. Sci. USA* 91(21):9680-4, Oct. 1994.

Palka, H. et al., "Hepatocyte Growth Factor Receptor Tyrosine Kinase Met is a Substrate of the Receptor Proteiin-Tyrosine Phosphatase DEP-1," *J. Biol. Chem.* 278(8):5728-35, Feb. 2003. Epub Dec. 9, 2002.

Pallen, C. et al., "Elevation of Membrane Tyrosine Phosphatase Activity in Density-Dependent Growth-Arrested Fibroblasts," *Proc. Natl. Acad. Sci. USA* 88(16):6996-7000, Aug. 1991.

Palou, E. et al., "CD148, A Membrane Protein Tyrosine Phosphatase, is Able to Induce Tyrosine Phosphorylation on Human Lymphocytes," *Immunol. Lett.* 57(1-3):101-3, Jun. 1997.

Park, M. et al., "Sequence of MET Protooncogene cDNA has Features Characteristic of the Tyrosine Kinase Family of Growth-Factor Receptors," *Proc. Natl. Acad. Sci. USA* 84(18):6379-83, Sep. 1987.
Patthy, L., "Homology of a Domain of the Growth Hormone/ Prolactin Receptor Family with Type III Modules of Fibronectin," *Cell* 61(1):Apr. 13-14, 1990.
Pelicci, G. et al., "The Motogenic and Mitogenic Responses to HGF are Amplified by the Shc Adaptor Protein," *Oncogene* 10(8):1631-8, Apr. 1995.
Pingel, J. et al., "Evidence that the Leukocyte-Common Antigen is Required for the Antigen-Induced T Lymphocyte Proliferation," *Cell* 58(6):1055-1065, Sep. 1989.
Ponzetto, C. et al., "A Multifunctional Docking Site Mediates Signaling and Transformation by the Hepatocyte Growth Factor/ Scatter Factor Receptor Family," *Cell.* 77(2):261-71, Apr. 1994.
Ponzetto, C. et al., "Specific Uncoupling of GRB2 from the Met Receptor. Differential Effects on Transformation and Motility," *J Biol Chem.* 271(24):14119-23, Jun. 1996.
Rijksen, G. et al., "Orthovanadate Both Mimics and Antagonizes the Transforming Growth Factor β Action on Normal Rat Kidney Cells," *J. Cell Physiol.* 154(2):393-401, 1993.
Rodrigues, G. et al., "Autophosphorylation Modulates the Kinase Activity and Oncogenic Potential of the Met Receptor Tyrosine Kinase," *Oncogene* 9(7):2019-27, Jul. 1994.
Ruivenkamp, C. et al., "*Ptprj* is a Candidate for the Mouse Colon-Cancer Susceptibility Locus *Sccl* and is Frequently Deleted in Human Cancers," *Nat. Genet.* 31(3):295-300, Jul. 2002.
Sachs, M. et al., "Essential Role of Gab1 for Signaling by the c-Met Receptor in Vivo," *J. Cell Biol.* 150(6):1375-84, Sep. 2000.
Sachs, M. et al., "Motogenic and Morphogenic Activity of Epithelial Receptor Tyrosine Kinases," *J Cell Biol.* 133(5):1095-1107, Jun. 1996.
Sambrook et al., *Molecular Cloning*, CSH Laboratory Press, 1989, pp. 16.17-16.22.
Sambrook et al., *Molecular Cloning*, CSH Laboratory Press, 1989, pp. 16.32-16.40.
Shulz, L. et al., "Mutations at the Murine Motheaten Locus are wihin the Hematopoietic Cell Protein-Tyrosine Phosphatase (*Hcph*) Gene," *Cell* 73(7):1445-1454, 1993.
Schwarzbauer, J., "Fibronectin: From Gene to Protein," *Curr. Opin. Cell. Biol.* 3(5):786-791, 1991.
Scottt, J. et al., "Searching for Peptide Ligands with an Epitope Library," *Science* 249(4967):386-390, Jul. 1990.
Seed, B. et al., "Molecular Cloning of the CD2 Antigen, the T-Cell Erythrocyte Receptor, by a Rapid Immunoselection Procedure," *Proc. Natl. Acad. Sci. USA* 84(10):3365-3369, May 1987.
Shibamoto, S. et al., "Tyrosine Phosphorylation of β-Catenin and Plakoglobin Enhanced by Hepatocyte Growth Factor and Epidermal Growth Factor in Human Carcinoma Cells," *Cell Adhes. Commun.* 1(4):295-305, Jan. 1994.
Stockinger, A. et al., "E-Cadherin Regulates Cell Growth by Modulating Proliferation-Dependent β-Catenin Transcriptional Activity," *J. Cell Biol.* 154(6):1185-96, Sep. 2001.
Stoker, M. et al., "Density Dependent Inhibition of Cell Growth in Culture," *Nature* 215(97):171-172, Jul. 1967.
Streuli, M. et al., "A New Member of the Immunoglobulin Superfamily that has a Cytoplasmic Region Homologous to the Leukocyte Common Antigen," *J. Exp. Med.* 168(5):1523-1530, Nov. 1988.
Streuli, M. et al., "Expression of the Receptor-linked Protein Tryosine Phosphatase LAR: Proteolytic Cleavage and Shedding of CAM-Like Extracellular Region," *EMBO J.* 11(3):897-907, Mar. 1992.
Sun, H. et al., "MKP-1 (3CH134), An Immediate Early Gene Product, is a Dual Specificity Phosphatase that Dephosphorylates MAP Kinase in Vivo," *Cell* 75(3):487-93, Nov. 1993.
Takahashi, T. et al., "Endothelial Localization of Receptor Tyrosine Phosphatase, ECRTP/DEP-1, in Developing and Mature Renal Vasculature," *J Am Soc Nephrol.* 10(10):2135-45, Oct. 1999.
Tian, S-S. et al., "Three Receptor-Linked Protein-Tyrosine Phosphatases are Selectively Expressed on Central Nervous System Axons in the Drosophila Embryo," *Cell* 67(4):675-685, Nov. 1991.

Tonks, N. et al., "Purification of the Major Protein-tyrosine-phosphatases of Human Placenta," *J. Biol. Chem.* 263(14):6722-6730, May 1988.
Tonks, N., "Protein Phosphatases: Key Players in the Regulation of Cell Function," *Curr. Opin. Cell. Biol.* 2(6):1114-1124, Dec. 1990.
Trapasso, F. et al., "Rat Protein Tyrosine Phosphatase η Suppresses the Neoplastic Phenotype of Retrovirally Transformed Thyroid Cells Through the Stabilizaiton of p27$^{Kip1}$," *Mol Cell Biol.* 20(24):9236-46, Dec. 2000.
Vadnais, J. et al., "Autocrine Activation of the Hepatocyte Growth Factor Receptor/Met Tyrosine Kinase Induces Tumor Cell Motility by Regulating Pseudopodial Protrusion," *J. Biol Chem.* 277(50):48342-50, Dec. 2002.
Van Vactor, D. et al., "Genetic Analysis of Protein Tyrosine Phosphatases," *Curr. Opin. Genet. Dev.* 8(1):112-26, Feb. 1998.
Voet et al., *Biochemistry*, John Wiley & Sons, Inc., pp. 126-128 & 228-234, 1990.
Vojtek, A. et al., "Mammalian RAS Interacts directly with the Serine/Threonine Kinase Raf," *Cell* 74(1):205-214, Jul. 1993.
Wary, K. et al., "A Homozygous Deletion Within the Carbonic Anhydrase-Like Domain of the *Ptprg* Gene in Murine L-Cells," *Cancer Res.* 53(7):1498-1502, Apr. 1993.
Weidner, K. et al., "Interaction Between Gab1 and the c-Met Receptor Tyrosine Kinase is Responsible for Epithelial Morphogenesis," *Nature* 384(6605):173-6, Nov. 1996.
Weidner, K. et al., "Mutation of Juxtamembrane Tyrosine Residue 1001 Suppresses Loss-of-Function Mutations of the Met Receptor in Epithelial Cells," *Proc. Natl. Acad. Sci. USA* 92(7):2597-2601, Mar. 1995.
Weidner, K. et al.,"The *Met* Receptor Tyrosine Kinase Transduces Motility, Proliferation, and Morphogenic Signals of Scatter Factor/ Hepatocyte Growth Factor in Epithelial Cells," *J. Cell Biol.* 121(1):145-154, Apr. 1993.
Yang, Q. et al., "Isolation of cDNA Clone Encoding a Human Protein-Tyrosine Phosphatase with Homology to the Cytoskeletal-Associated Proteins Band 4.1, erzin, and talin," *Proc. Natl. Acad. Sci. USA* 88(14):5949-5953, Jul. 1991.
Yang, X. et al., "A Protein Kinase Substrate Identified by the Two-Hybrid System," *Science* 257(5070):680-682, Jul. 1992.
Yang, X. et al., "Two Drosophila Receptor-like Tyrosine Phosphatase Genes are Expressed in a Subset of Developing Axons and Pioneer Neurons in the Embryonic CNS," *Cell* 67(4):661-673, Nov. 1991.
Young, R. et al., "Efficient Isolation of Genes by Using Antibody Probes," *Proc. Natl. Acad. Sci. USA* 80(5):1194-1198, Mar. 1983.
Zhang, L. et al., "Thyroid Cell Transformation Inhibits the Expression of a Novel Rat Protein Tyrosine Phosphatase," *Exp Cell Res.* 235(1):62-70, Aug. 1997.
Zhu, H. et al., "Receptor Chimeras Indicate that the *Met* Tyrosine Kinase Mediates the Motility and Morphogenic Responses of Hepatocyte Growth/Scatter Factor," *Cell Growth Differ.* 5(4):359-66, Apr. 1994.
OMIM database Accession No. 116806, retrieved Apr. 21, 2004.
OMIM database Accession No. 164860, retrieved Apr. 21, 2004.
OMIM database Accession No. 173325, retrieved Apr. 21, 2004.
OMIM database Accession No. 601045, retrieved Apr. 21, 2004.
OMIM database Accession No. 604439, retrieved Apr. 21, 2004.
Genbank Accession No. 1204266A, May 20, 1996.
Genbank Accession No. AAA59591, Jan. 7, 1995.
Genbank Accession No. AAB36687, Nov. 26, 1996.
Genbank Accession No. AF062317, Jul. 2, 1998.
Genbank Accession No. AF062319, Jul. 2, 1998.
Genbank Accession No. AF062321, Jul. 2, 1998.
Genbank Accession No. AF062338, Jul. 2, 1998.
Genbank Accession No. AF062342, Jul. 2, 1998.
Genbank Accession No. BC011865, Oct. 4, 2003.
Genbank Accession No. NM_000245, Feb. 23, 2004.
Genbank Accession No. NM_001904, Dec. 20, 2003.
Genbank Accession No. NM_002039, Apr. 14, 2004.
Genbank Accession No. NM_021991, Dec. 21, 2003.
Genbank Accession No. NP_000236, Feb. 23, 2004.
Genbank Accession No. NP_005202, Dec. 20, 2003.
Genbank Accession No. P08581, Jun. 15, 2004.
Genbank Accession No. P07333, Jun. 15, 2004.
Genbank Accession No. Z68228, Dec. 14, 1995.

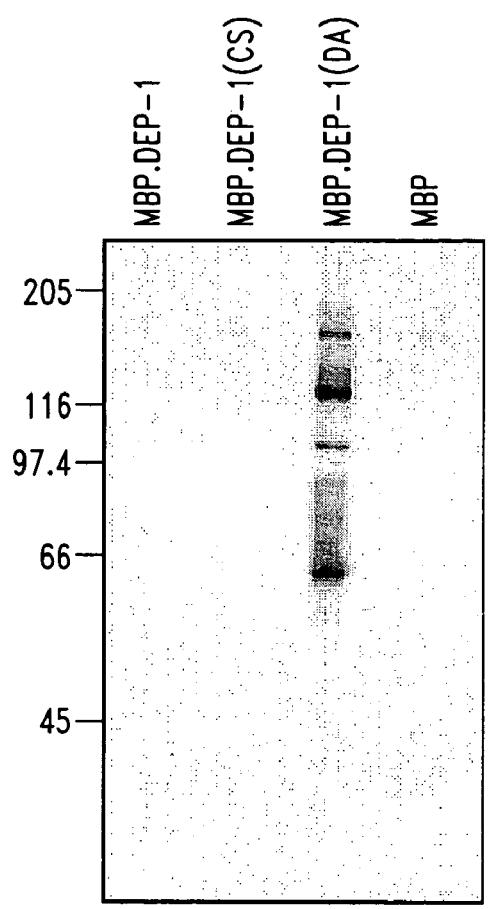
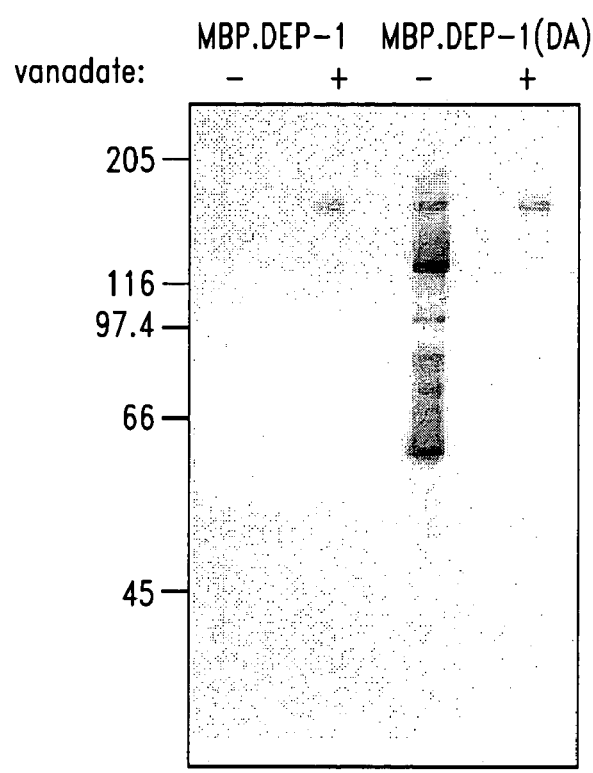
FIG. 2A
FIG. 2B

SEQUENCE LISTING

<160> NUMBER OF SEQ ID NOS: 22

<210> SEQ ID NO 1
<211> LENGTH: 5117
<212> TYPE: DNA
<213> ORGANISM: Homo sapiens

<400> SEQUENCE: 1

| | | | | | | |
|---|---|---|---|---|---|---|
| ccccagccgc | atgacgcgcg | gaggaggcag | cgggacgagc | gcgggagccg | ggaccgggta | 60 |
| gccgcgcgct | gggggtgggc | gccgctcgct | ccgccccgcg | aagcccctgc | gcgctcaggg | 120 |
| acgcggcccc | cccgcggcag | ccgcgctagg | ctccggcgtg | tggccgcggc | cgccgccgcg | 180 |
| ctgccatgtc | tccgggcaag | ccggggcggg | cggagcgggg | acgaggcgga | ccggctggcg | 240 |
| gaggaggagg | cgaaggagac | ggcaggaggc | ggcgacgacg | gtgcccgggc | tcgggcgcac | 300 |
| ggcgggggccc | gattcgcgcg | tccggggcac | gttccagggc | gcgcgggggca | tgaagccggc | 360 |
| ggcgcgggag | gcgcggctgc | ctccgcgctc | gcccgggctg | cgctgggcgc | tgccgctgct | 420 |
| gctgctgctg | ctgcgcctgg | gccagatcct | gtgcgcaggt | ggcaccccta | gtccaattcc | 480 |
| tgacccttca | gtagcaactg | ttgccacagg | ggaaaatggc | ataacgcaga | tcagcagtac | 540 |
| agcagaatcc | tttcataaac | agaatggaac | tggaacacct | caggtggaaa | caaacaccag | 600 |
| tgaggatggt | gaaagctctg | gagccaacga | tagtttaaga | cacctgaac | aaggatctaa | 660 |
| tgggactgat | ggggcatctc | aaaaaactcc | cagtagcact | gggcccagtc | ctgtgtttga | 720 |
| cattaaagct | gtttccatca | gtccaaccaa | tgtgatctta | acttggaaaa | gtaatgacac | 780 |
| agctgcttct | gagtacaagt | atgtagtaaa | gcataagatg | gaaaatgaga | agacaattac | 840 |
| tgttgtgcat | caaccatggt | gtaacatcac | aggcttacgt | ccagcgactt | catatgtatt | 900 |
| ctccatcact | ccaggaatag | gcaatgagac | ttggggagat | cccagagtca | taaaagtcat | 960 |
| cacagagccg | atcccagttt | ctgatctccg | tgttgccctc | acgggtgtga | ggaaggctgc | 1020 |
| tctctcctgg | agcaatggca | atggcaccgc | ctcctgccgg | gttcttcttg | aaagcattgg | 1080 |
| aagccatgag | gagttgactc | aagactcaag | acttcaggtc | aatatctcgg | acctgaagcc | 1140 |
| agggggttcaa | tacaacatca | acccgtatct | tctacaatca | aataagcaaa | agggagaccc | 1200 |
| cttgggcaca | gaaggtggct | tggatgccag | caatacagag | agaagccggg | cagggagccc | 1260 |
| caccgccccct | gtgcatgatg | agtccctcgt | gggacctgtg | gacccatcct | ccggccagca | 1320 |
| gtcccgagac | acggaagtcc | tgcttgtcgg | gttagagcct | ggcacccgat | acaatgccac | 1380 |
| cgtttattcc | caagcagcga | atggcacaga | aggacagccc | caggccatag | agttcaggac | 1440 |
| aaatgctatt | caggttttttg | acgtcaccgc | tgtgaacatc | agtgccacaa | gcctgaccct | 1500 |
| gatctggaaa | gtcagcgata | acgagtcgtc | atctaactat | acctacaaga | tacatgtggc | 1560 |
| gggggagaca | gattcttcca | atctcaacgt | cagtgagcct | cgcgctgtca | tccccggact | 1620 |
| ccgctccagc | accttctaca | acatcacagt | gtgtcctgtc | ctaggtgaca | tcgagggcac | 1680 |
| gccgggcttc | ctccaagtgc | acacccccccc | tgttccagtt | tctgacttcc | gagtgacagt | 1740 |
| ggtcagcacg | acggagatcg | gcttagcatg | gagcagccat | gatgcagaat | catttcagat | 1800 |
| gcatatcaca | caggagggag | ctggcaattc | tcgggtagaa | ataaccacca | accaaagtat | 1860 |
| tatcattggt | ggcttgttcc | ctggaaccaa | gtattgcttt | gaaatagttc | caaaaggacc | 1920 |
| aaatgggact | gaagggggcat | ctcggacagt | ttgcaataga | actgttccca | gtgcagtgtt | 1980 |
| tgacatccac | gtggtctacg | tcaccaccac | ggagatgtgg | ctggactgga | agagccctga | 2040 |

-continued

```
cggtgcttcc gagtatgtct accatttagt catagagtcc aagcatggct ctaaccacac    2100
aagcacgtat gacaaagcga ttactctcca gggcctgatt ccgggcacct tatataacat    2160
caccatctct ccagaagtgg accacgtctg ggggacccc aactccactg cacagtacac     2220
acggcccagc aatgtgtcca acattgatgt aagtaccaac accacagcag caactttaag    2280
ttggcagaac tttgatgacg cctctcccac gtactcctac tgccttctta ttgagaaggc    2340
tggaaattcc agcaacgcaa cacaagtagt cacggacatt ggaattactg acgctacagt    2400
cactgaatta atacctggct catcatacac agtggagatc tttgcacaag taggggatgg    2460
gatcaagtca ctggaacctg ccggaagtc attctgtaca gatcctgcgt ccatggcctc     2520
cttcgactgc gaagtggtcc ccaaagagcc agccctggtt ctcaaatgga cctgccctcc    2580
tggcgccaat gcaggctttg agctggaggt cagcagtgga gcctggaaca atgcgaccca    2640
cctggagagc tgctcctctg agaatggcac tgagtataga acggaagtca cgtatttgaa    2700
tttttctacc tcgtacaaca tcagcatcac cactgtgtcc tgtggaaaga tggcagcccc    2760
cacccggaac acctgcacta ctggcatcac agatccccct cctccagatg gatcccctaa    2820
tattacatct gtcagtcaca attcagtaaa ggtcaagttc agtggatttg aagccagcca    2880
cggacccatc aaagcctatg ctgtcattct caccaccggg gaagctggtc acccttctgc    2940
agatgtcctg aaatacacgt atgacgattt caaaaaggga gcctcagata cttatgtgac    3000 ataccctcata agaacagaag aaaagggacg ttctcagagc ttgtctgaag ttttgaaata   3060
tgaaattgac gttgggaatg agtcaaccac acttggttat acaatggga agctggaacc     3120 tctgggctcc taccgggctt gtgtggctgg cttcaccaac attaccttcc accctcaaaa    3180
caaggggctc attgatgggg ctgagagcta tgtgtccttc agtcgctact cagatgctgt    3240
ttccttgccc caggatccag gtgtcatctg tggagcggtt tttggctgta tctttggtgc    3300
cctggttatt gtgactgtgg gaggcttcat cttctggaga aagaaggagga aagatgcaaa    3360 gaataatgaa gtgtccttt ctcaaattaa acctaaaaaa tctaagttaa tcagagtgga    3420
gaattttgag gcctacttca agaagcagca agctgactcc aactgtgggt cgcagagga    3480 atacgaagat ctgaagcttg ttggaattag tcaacctaaa tatgcagcag aactggctga    3540
gaatagagga aagaatcgct ataataatgt tctgcctat gatatttccc gtgtcaaact     3600
ttcggtccag acccattcaa cggatgacta catcaatgcc aactacatgc tggctacca    3660 ctccaagaaa gatttattg ccacacaagg acctttaccg aacactttga aagatttttg    3720
gcgtatggtt tgggagaaaa atgtatatgc catcattatg ttgactaaat gtgttgaaca    3780
gggaagaacc aaatgtgagg agtattggcc ctccaagcag gctcaggact atggagacat    3840
aactgtggca atgacatcag aaattgttct tccggaatgg accatcagag atttcacagt    3900
gaaaaatatc cagacaagtg agagtcaccc tctgagacag ttccatttca cctcctggcc    3960
agaccacggt gttcccgaca ccactgacct gctcatcaac ttccggtacc tcgttcgtga    4020
ctacatgaag cagagtcctc ccgaatcgcc gattctggtg cattgcagtg ctggggtcgg    4080
aaggacgggc actttcattg ccattgatcg tctcatctac cagatagaga atgagaacac    4140
cgtggatgtg tatgggattg tgtatgacct tcgaatgcat aggcctttaa tggtgcagac    4200
agaggaccag tatgtttcc tcaatcagtg tgttttggat attgtcagat cccagaaaga    4260
ctcaaaagta gatcttatct accagaacac aactgcaatg acaatctatg aaaaccttgc    4320
gcccgtgacc acatttggaa agaccaatgg ttacatcgcc taattccaaa ggaataacct    4380
```

-continued

```
ttctggagtg aaccagaccg tcgcacccac agcgaaggca catgccccga tgtcgacatg    4440
tttttatatg tctaatatct taattctttg ttctgttttg tgagaactaa ttttgagggc    4500
atgaagctgc atatgataga tgacaaattg gggctgtcgg gggctgtgga tgggtgggga    4560
gcaaatcatc tgcattcctg atgaccaatg ggatgaggtc acttttttt ttttcccct     4620 tgaggattgc ggaaaaccag gaaaagggat ctatgatttt tttttccaaa acaatttctt    4680
ttttaaaaag actattttat atgattcaca tgctaaagcc aggattgtgt tgggttgaat    4740
atattttaag tatcagaggt ctattttac ctactgtgtc ttggaatcta gccgatggaa    4800
aatacctaat tgtggatgat gattgcgcag ggaggggtac gtggcacctc ttccgaatgg    4860
gttttctatt tgaacatgtg cctttctga attatgcttc cacaggcaaa actcagtaga    4920
gatctatatt tttgtactga atctcataat tggaatatac ggaatattta aacagtagct    4980
tagcatcaga ggtttgcttc ctcagtaaca tttctgttct catttgatca ggggaggcct    5040
ctttgccccg gccccgcttc ccctgccccc gtgtgatttg tgctccattt tttcttccct    5100
tttccctccc agttttc                                                  5117
```

<210> SEQ ID NO 2
<211> LENGTH: 1337
<212> TYPE: PRT
<213> ORGANISM: Homo sapiens

<400> SEQUENCE: 2

```
Met Lys Pro Ala Ala Arg Glu Ala Arg Leu Pro Pro Arg Ser Pro Gly
  1               5                  10                  15

Leu Arg Trp Ala Leu Pro Leu Leu Leu Leu Leu Arg Leu Gly Gln
             20                  25                  30

Ile Leu Cys Ala Gly Gly Thr Pro Ser Pro Ile Pro Asp Pro Ser Val
         35                  40                  45

Ala Thr Val Ala Thr Gly Glu Asn Gly Ile Thr Gln Ile Ser Ser Thr
     50                  55                  60

Ala Glu Ser Phe His Lys Gln Asn Gly Thr Gly Thr Pro Gln Val Glu
 65                  70                  75                  80

Thr Asn Thr Ser Glu Asp Gly Glu Ser Ser Gly Ala Asn Asp Ser Leu
                 85                  90                  95

Arg Thr Pro Glu Gln Gly Ser Asn Gly Thr Asp Gly Ala Ser Gln Lys
            100                 105                 110

Thr Pro Ser Ser Thr Gly Pro Ser Pro Val Phe Asp Ile Lys Ala Val
        115                 120                 125

Ser Ile Ser Pro Thr Asn Val Ile Leu Thr Trp Lys Ser Asn Asp Thr
    130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
                165                 170                 175

Arg Pro Ala Thr Ser Tyr Val Phe Ser Ile Thr Pro Gly Ile Gly Asn
            180                 185                 190

Glu Thr Trp Gly Asp Pro Arg Val Ile Lys Val Ile Thr Glu Pro Ile
        195                 200                 205

Pro Val Ser Asp Leu Arg Val Ala Leu Thr Gly Val Arg Lys Ala Ala
    210                 215                 220

Leu Ser Trp Ser Asn Gly Asn Gly Thr Ala Ser Cys Arg Val Leu Leu
225                 230                 235                 240
```

```
Glu Ser Ile Gly Ser His Glu Leu Thr Gln Asp Ser Arg Leu Gln
                245                 250                 255

Val Asn Ile Ser Asp Leu Lys Pro Gly Val Gln Tyr Asn Ile Asn Pro
            260                 265                 270

Tyr Leu Leu Gln Ser Asn Lys Thr Lys Gly Asp Pro Leu Gly Thr Glu
                275                 280                 285

Gly Gly Leu Asp Ala Ser Asn Thr Glu Arg Ser Arg Ala Gly Ser Pro
290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
                340                 345                 350

Thr Glu Gly Gln Pro Gln Ala Ile Glu Phe Arg Thr Asn Ala Ile Gln
                355                 360                 365

Val Phe Asp Val Thr Ala Val Asn Ile Ser Ala Thr Ser Leu Thr Leu
            370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415

Pro Arg Ala Val Ile Pro Gly Leu Arg Ser Ser Thr Phe Tyr Asn Ile
                420                 425                 430

Thr Val Cys Pro Val Leu Gly Asp Ile Glu Gly Thr Pro Gly Phe Leu
            435                 440                 445

Gln Val His Thr Pro Pro Val Pro Val Ser Asp Phe Arg Val Thr Val
            450                 455                 460

Val Ser Thr Thr Glu Ile Gly Leu Ala Trp Ser Ser His Asp Ala Glu
465                 470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Ile Gly Gly Leu Phe Pro Gly
                500                 505                 510

Thr Lys Tyr Cys Phe Glu Ile Val Pro Lys Gly Pro Asn Gly Thr Glu
            515                 520                 525

Gly Ala Ser Arg Thr Val Cys Asn Arg Thr Val Pro Ser Ala Val Phe
530                 535                 540

Asp Ile His Val Val Tyr Val Thr Thr Thr Glu Met Trp Leu Asp Trp
545                 550                 555                 560

Lys Ser Pro Asp Gly Ala Ser Glu Tyr Val Tyr His Leu Val Ile Glu
                565                 570                 575

Ser Lys His Gly Ser Asn His Thr Ser Thr Tyr Asp Lys Ala Ile Thr
            580                 585                 590

Leu Gln Gly Leu Ile Pro Gly Thr Leu Tyr Asn Ile Thr Ile Ser Pro
            595                 600                 605

Glu Val Asp His Val Trp Gly Asp Pro Asn Ser Thr Ala Gln Tyr Thr
                610                 615                 620

Arg Pro Ser Asn Val Ser Asn Ile Asp Val Ser Thr Asn Thr Thr Ala
625                 630                 635                 640

Ala Thr Leu Ser Trp Gln Asn Phe Asp Asp Ala Ser Pro Thr Tyr Ser
                645                 650                 655

Tyr Cys Leu Leu Ile Glu Lys Ala Gly Asn Ser Ser Asn Ala Thr Gln
```

-continued

```
            660                 665                 670
Val Val Thr Asp Ile Gly Ile Thr Asp Ala Thr Val Thr Glu Leu Ile
            675                 680                 685
Pro Gly Ser Ser Tyr Thr Val Glu Ile Phe Ala Gln Val Gly Asp Gly
            690                 695                 700
Ile Lys Ser Leu Glu Pro Gly Arg Lys Ser Phe Cys Thr Asp Pro Ala
705                 710                 715                 720
Ser Met Ala Ser Phe Asp Cys Glu Val Val Pro Lys Glu Pro Ala Leu
                    725                 730                 735
Val Leu Lys Trp Thr Cys Pro Gly Ala Asn Ala Gly Phe Glu Leu
            740                 745                 750
Glu Val Ser Ser Gly Ala Trp Asn Asn Ala Thr His Leu Glu Ser Cys
            755                 760                 765
Ser Ser Glu Asn Gly Thr Glu Tyr Arg Thr Glu Val Thr Tyr Leu Asn
            770                 775                 780
Phe Ser Thr Ser Tyr Asn Ile Ser Ile Thr Thr Val Ser Cys Gly Lys
785                 790                 795                 800
Met Ala Ala Pro Thr Arg Asn Thr Cys Thr Thr Gly Ile Thr Asp Pro
                    805                 810                 815
Pro Pro Pro Asp Gly Ser Pro Asn Ile Thr Ser Val Ser His Asn Ser
                    820                 825                 830
Val Lys Val Lys Phe Ser Gly Phe Glu Ala Ser His Gly Pro Ile Lys
            835                 840                 845
Ala Tyr Ala Val Ile Leu Thr Thr Gly Glu Ala Gly His Pro Ser Ala
            850                 855                 860
Asp Val Leu Lys Tyr Thr Tyr Asp Asp Phe Lys Lys Gly Ala Ser Asp
865                 870                 875                 880
Thr Tyr Val Thr Tyr Leu Ile Arg Thr Glu Glu Lys Gly Arg Ser Gln
                    885                 890                 895
Ser Leu Ser Glu Val Leu Lys Tyr Glu Ile Asp Val Gly Asn Glu Ser
            900                 905                 910
Thr Thr Leu Gly Tyr Tyr Asn Gly Lys Leu Glu Pro Leu Gly Ser Tyr
            915                 920                 925
Arg Ala Cys Val Ala Gly Phe Thr Asn Ile Thr Phe His Pro Gln Asn
            930                 935                 940
Lys Gly Leu Ile Asp Gly Ala Glu Ser Tyr Val Ser Phe Ser Arg Tyr
945                 950                 955                 960
Ser Asp Ala Val Ser Leu Pro Gln Asp Pro Gly Val Ile Cys Gly Ala
                    965                 970                 975
Val Phe Gly Cys Ile Phe Gly Ala Leu Val Ile Val Thr Val Gly Gly
                    980                 985                 990
Phe Ile Phe Trp Arg Lys Arg Lys Asp Ala Lys Asn Asn Glu Val
            995                 1000                1005
Ser Phe Ser Gln Ile Lys Pro Lys Lys Ser Lys Leu Ile Arg Val Glu
            1010                1015                1020
Asn Phe Glu Ala Tyr Phe Lys Lys Gln Gln Ala Asp Ser Asn Cys Gly
1025                1030                1035                1040
Phe Ala Glu Glu Tyr Glu Asp Leu Lys Leu Val Gly Ile Ser Gln Pro
                    1045                1050                1055
Lys Tyr Ala Ala Glu Leu Ala Glu Asn Arg Gly Lys Asn Arg Tyr Asn
                    1060                1065                1070
Asn Val Leu Pro Tyr Asp Ile Ser Arg Val Lys Leu Ser Val Gln Thr
            1075                1080                1085
```

His Ser Thr Asp Asp Tyr Ile Asn Ala Asn Tyr Met Pro Gly Tyr His
    1090                1095                1100

Ser Lys Lys Asp Phe Ile Ala Thr Gln Gly Pro Leu Pro Asn Thr Leu
1105                1110                1115                1120

Lys Asp Phe Trp Arg Met Val Trp Glu Lys Asn Val Tyr Ala Ile Ile
                1125                1130                1135

Met Leu Thr Lys Cys Val Glu Gln Gly Arg Thr Lys Cys Glu Glu Tyr
            1140                1145                1150

Trp Pro Ser Lys Gln Ala Gln Asp Tyr Gly Asp Ile Thr Val Ala Met
        1155                1160                1165

Thr Ser Glu Ile Val Leu Pro Glu Trp Thr Ile Arg Asp Phe Thr Val
    1170                1175                1180

Lys Asn Ile Gln Thr Ser Glu Ser His Pro Leu Arg Gln Phe His Phe
1185                1190                1195                1200

Thr Ser Trp Pro Asp His Gly Val Pro Asp Thr Thr Asp Leu Leu Ile
                1205                1210                1215

Asn Phe Arg Tyr Leu Val Arg Asp Tyr Met Lys Gln Ser Pro Pro Glu
            1220                1225                1230

Ser Pro Ile Leu Val His Cys Ser Ala Gly Val Gly Arg Thr Gly Thr
        1235                1240                1245

Phe Ile Ala Ile Asp Arg Leu Ile Tyr Gln Ile Glu Asn Glu Asn Thr
    1250                1255                1260

Val Asp Val Tyr Gly Ile Val Tyr Asp Leu Arg Met His Arg Pro Leu
1265                1270                1275                1280

Met Val Gln Thr Glu Asp Gln Tyr Val Phe Leu Asn Gln Cys Val Leu
                1285                1290                1295

Asp Ile Val Arg Ser Gln Lys Asp Ser Lys Val Asp Leu Ile Tyr Gln
            1300                1305                1310

Asn Thr Thr Ala Met Thr Ile Tyr Glu Asn Leu Ala Pro Val Thr Thr
        1315                1320                1325

Phe Gly Lys Thr Asn Gly Tyr Ile Ala
    1330                1335

<210> SEQ ID NO 3
<211> LENGTH: 341
<212> TYPE: PRT
<213> ORGANISM: Homo sapiens

<400> SEQUENCE: 3

Arg Lys Lys Arg Lys Asp Ala Lys Asn Asn Glu Val Ser Phe Ser Gln
1               5                   10                  15

Ile Lys Pro Lys Lys Ser Lys Leu Ile Arg Val Glu Asn Phe Glu Ala
                20                  25                  30

Tyr Phe Lys Lys Gln Gln Ala Asp Ser Asn Cys Gly Phe Ala Glu Glu
            35                  40                  45

Tyr Glu Asp Leu Lys Leu Val Gly Ile Ser Gln Pro Lys Tyr Ala Ala
        50                  55                  60

Glu Leu Ala Glu Asn Arg Gly Lys Asn Arg Tyr Asn Asn Val Leu Pro
65                  70                  75                  80

Tyr Asp Ile Ser Arg Val Lys Leu Ser Val Gln Thr His Ser Thr Asp
                85                  90                  95

Asp Tyr Ile Asn Ala Asn Tyr Met Pro Gly Tyr His Ser Lys Lys Asp
            100                 105                 110

Phe Ile Ala Thr Gln Gly Pro Leu Pro Asn Thr Leu Lys Asp Phe Trp

```
                   115                 120                 125
Arg Met Val Trp Glu Lys Asn Val Tyr Ala Ile Ile Met Leu Thr Lys
    130                 135                 140

Cys Val Glu Gln Gly Arg Thr Lys Cys Glu Glu Tyr Trp Pro Ser Lys
145                 150                 155                 160

Gln Ala Gln Asp Tyr Gly Asp Ile Thr Val Ala Met Thr Ser Glu Ile
                165                 170                 175

Val Leu Pro Glu Trp Thr Ile Arg Asp Phe Thr Val Lys Asn Ile Gln
            180                 185                 190

Thr Ser Glu Ser His Pro Leu Arg Gln Phe His Phe Thr Ser Trp Pro
        195                 200                 205

Asp His Gly Val Pro Asp Thr Thr Asp Leu Leu Ile Asn Phe Arg Tyr
    210                 215                 220

Leu Val Arg Asp Tyr Met Lys Gln Ser Pro Pro Glu Ser Pro Ile Leu
225                 230                 235                 240

Val His Cys Ser Ala Gly Val Gly Arg Thr Gly Thr Phe Ile Ala Ile
                245                 250                 255

Asp Arg Leu Ile Tyr Gln Ile Glu Asn Glu Asn Thr Val Asp Val Tyr
            260                 265                 270

Gly Ile Val Tyr Asp Leu Arg Met His Arg Pro Leu Met Val Gln Thr
        275                 280                 285

Glu Asp Gln Tyr Val Phe Leu Asn Gln Cys Val Leu Asp Ile Val Arg
    290                 295                 300

Ser Gln Lys Asp Ser Lys Val Asp Leu Ile Tyr Gln Asn Thr Thr Ala
305                 310                 315                 320

Met Thr Ile Tyr Glu Asn Leu Ala Pro Val Thr Thr Phe Gly Lys Thr
                325                 330                 335

Asn Gly Tyr Ile Ala
            340

<210> SEQ ID NO 4
<211> LENGTH: 1390
<212> TYPE: PRT
<213> ORGANISM: Homo sapiens

<400> SEQUENCE: 4

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140
```

```
Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
            165                 170                 175

Val Ser Ala Leu Gly Ala Lys Val Leu Ser Ser Val Lys Asp Arg Phe
        180                 185                 190

Ile Asn Phe Phe Val Gly Asn Thr Ile Asn Ser Ser Tyr Phe Pro Asp
    195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
```

```
                  565                 570                 575
Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990
```

```
Thr Glu Met Val Ser Asn Glu Ser Val Asp Tyr Arg Ala Thr Phe Pro
        995                 1000                1005
Glu Asp Gln Phe Pro Asn Ser Ser Gln Asn Gly Ser Cys Arg Gln Val
    1010                1015                1020
Gln Tyr Pro Leu Thr Asp Met Ser Pro Ile Leu Thr Ser Gly Asp Ser
1025                1030                1035                1040
Asp Ile Ser Ser Pro Leu Leu Gln Asn Thr Val His Ile Asp Leu Ser
            1045                1050                1055
Ala Leu Asn Pro Glu Leu Val Gln Ala Val Gln His Val Val Ile Gly
        1060                1065                1070
Pro Ser Ser Leu Ile Val His Phe Asn Glu Val Ile Gly Arg Gly His
        1075                1080                1085
Phe Gly Cys Val Tyr His Gly Thr Leu Leu Asp Asn Asp Gly Lys Lys
        1090                1095                1100
Ile His Cys Ala Val Lys Ser Leu Asn Arg Ile Thr Asp Ile Gly Glu
1105                1110                1115                1120
Val Ser Gln Phe Leu Thr Glu Gly Ile Ile Met Lys Asp Phe Ser His
            1125                1130                1135
Pro Asn Val Leu Ser Leu Leu Gly Ile Cys Leu Arg Ser Glu Gly Ser
        1140                1145                1150
Pro Leu Val Val Leu Pro Tyr Met Lys His Gly Asp Leu Arg Asn Phe
        1155                1160                1165
Ile Arg Asn Glu Thr His Asn Pro Thr Val Lys Asp Leu Ile Gly Phe
        1170                1175                1180
Gly Leu Gln Val Ala Lys Gly Met Lys Tyr Leu Ala Ser Lys Lys Phe
1185                1190                1195                1200
Val His Arg Asp Leu Ala Ala Arg Asn Cys Met Leu Asp Glu Lys Phe
            1205                1210                1215
Thr Val Lys Val Ala Asp Phe Gly Leu Ala Arg Asp Met Tyr Asp Lys
        1220                1225                1230
Glu Tyr Tyr Ser Val His Asn Lys Thr Gly Ala Lys Leu Pro Val Lys
        1235                1240                1245
Trp Met Ala Leu Glu Ser Leu Gln Thr Gln Lys Phe Thr Thr Lys Ser
        1250                1255                1260
Asp Val Trp Ser Phe Gly Val Val Leu Trp Glu Leu Met Thr Arg Gly
1265                1270                1275                1280
Ala Pro Pro Tyr Pro Asp Val Asn Thr Phe Asp Ile Thr Val Tyr Leu
            1285                1290                1295
Leu Gln Gly Arg Arg Leu Leu Gln Pro Glu Tyr Cys Pro Asp Pro Leu
        1300                1305                1310
Tyr Glu Val Met Leu Lys Cys Trp His Pro Lys Ala Glu Met Arg Pro
        1315                1320                1325
Ser Phe Ser Glu Leu Val Ser Arg Ile Ser Ala Ile Phe Ser Thr Phe
        1330                1335                1340
Ile Gly Glu His Tyr Val His Val Asn Ala Thr Tyr Val Asn Val Lys
1345                1350                1355                1360
Cys Val Ala Pro Tyr Pro Ser Leu Leu Ser Ser Glu Asp Asn Ala Asp
            1365                1370                1375
Asp Glu Val Asp Thr Arg Pro Ala Ser Phe Trp Glu Thr Ser
        1380                1385                1390

<210> SEQ ID NO 5
<211> LENGTH: 1408
```

```
<212> TYPE: PRT
<213> ORGANISM: Homo sapiens

<400> SEQUENCE: 5

Met Lys Ala Pro Ala Val Leu Ala Pro Gly Ile Leu Val Leu Leu Phe
 1               5                  10                  15

Thr Leu Val Gln Arg Ser Asn Gly Glu Cys Lys Glu Ala Leu Ala Lys
             20                  25                  30

Ser Glu Met Asn Val Asn Met Lys Tyr Gln Leu Pro Asn Phe Thr Ala
         35                  40                  45

Glu Thr Pro Ile Gln Asn Val Ile Leu His Glu His His Ile Phe Leu
 50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400
```

-continued

```
Thr Leu Leu Arg Asn Ser Ser Gly Cys Glu Ala Arg Arg Asp Glu Tyr
            405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
                515                 520                 525
Cys Leu Ser Ala Pro Pro Phe Val Gln Cys Gly Trp Cys His Asp Lys
            530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
            610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
            690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Thr Trp Trp Lys Glu Pro Leu Asn Ile Val Ser Phe Leu
            755                 760                 765
Phe Cys Phe Ala Ser Gly Gly Ser Thr Ile Thr Gly Val Gly Lys Asn
770                 775                 780
Leu Asn Ser Val Ser Val Pro Arg Met Val Ile Asn Val His Glu Ala
785                 790                 795                 800
Gly Arg Asn Phe Thr Val Ala Cys Gln His Arg Ser Asn Ser Glu Ile
                805                 810                 815
```

-continued

```
Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
            850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
            915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
            980                 985                 990

Val His Thr Pro His Leu Asp Arg Leu Val Ser Ala Arg Ser Val Ser
            995                 1000                1005

Pro Thr Thr Glu Met Val Ser Asn Glu Ser Val Asp Tyr Arg Ala Thr
            1010                1015                1020

Phe Pro Glu Asp Gln Phe Pro Asn Ser Ser Gln Asn Gly Ser Cys Arg
1025                1030                1035                1040

Gln Val Gln Tyr Pro Leu Thr Asp Met Ser Pro Ile Leu Thr Ser Gly
                1045                1050                1055

Asp Ser Asp Ile Ser Ser Pro Leu Leu Gln Asn Thr Val His Ile Asp
            1060                1065                1070

Leu Ser Ala Leu Asn Pro Glu Leu Val Gln Ala Val Gln His Val Val
            1075                1080                1085

Ile Gly Pro Ser Ser Leu Ile Val His Phe Asn Glu Val Ile Gly Arg
            1090                1095                1100

Gly His Phe Gly Cys Val Tyr His Gly Thr Leu Leu Asp Asn Asp Gly
1105                1110                1115                1120

Lys Lys Ile His Cys Ala Val Lys Ser Leu Asn Arg Ile Thr Asp Ile
            1125                1130                1135

Gly Glu Val Ser Gln Phe Leu Thr Glu Gly Ile Ile Met Lys Asp Phe
            1140                1145                1150

Ser His Pro Asn Val Leu Ser Leu Leu Gly Ile Cys Leu Arg Ser Glu
            1155                1160                1165

Gly Ser Pro Leu Val Val Leu Pro Tyr Met Lys His Gly Asp Leu Arg
            1170                1175                1180

Asn Phe Ile Arg Asn Glu Thr His Asn Pro Thr Val Lys Asp Leu Ile
1185                1190                1195                1200

Gly Phe Gly Leu Gln Val Ala Lys Ala Met Lys Tyr Leu Ala Ser Lys
                1205                1210                1215

Lys Phe Val His Arg Asp Leu Ala Ala Arg Asn Cys Met Leu Asp Glu
            1220                1225                1230

Lys Phe Thr Val Lys Val Ala Asp Phe Gly Leu Ala Arg Asp Met Tyr
```

-continued

```
                    1235                1240                1245

Asp Lys Glu Tyr Tyr Ser Val His Asn Lys Thr Gly Ala Lys Leu Pro
    1250                1255                1260

Val Lys Trp Met Ala Leu Glu Ser Leu Gln Thr Gln Lys Phe Thr Thr
1265                1270                1275                1280

Lys Ser Asp Val Trp Ser Phe Gly Val Val Leu Trp Glu Leu Met Thr
                1285                1290                1295

Arg Gly Ala Pro Pro Tyr Pro Asp Val Asn Thr Phe Asp Ile Thr Val
            1300                1305                1310

Tyr Leu Leu Gln Gly Arg Arg Leu Leu Gln Pro Glu Tyr Cys Pro Asp
        1315                1320                1325

Pro Leu Tyr Glu Val Met Leu Lys Cys Trp His Pro Lys Ala Glu Met
    1330                1335                1340

Arg Pro Ser Phe Ser Glu Leu Val Ser Arg Ile Ser Ala Ile Phe Ser
1345                1350                1355                1360

Thr Phe Ile Gly Glu His Tyr Val His Val Asn Ala Thr Tyr Val Asn
                1365                1370                1375

Val Lys Cys Val Ala Pro Tyr Pro Ser Leu Leu Ser Ser Glu Asp Asn
            1380                1385                1390

Ala Asp Asp Glu Val Asp Thr Arg Pro Ala Ser Phe Trp Glu Thr Ser
        1395                1400                1405

<210> SEQ ID NO 6
<211> LENGTH: 1408
<212> TYPE: PRT
<213> ORGANISM: Homo sapiens

<400> SEQUENCE: 6

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205
```

-continued

```
His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
```

```
              625                 630                 635                 640
Ser Asn Gly His Gly Thr Thr Gln Tyr Ser Thr Phe Ser Tyr Val Asp
                    645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
        690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Thr Trp Trp Lys Glu Pro Leu Asn Ile Val Ser Phe Leu
            755                 760                 765
Phe Cys Phe Ala Ser Gly Gly Ser Thr Ile Thr Gly Val Gly Lys Asn
        770                 775                 780
Leu Asn Ser Val Ser Val Pro Arg Met Val Ile Asn Val His Glu Ala
785                 790                 795                 800
Gly Arg Asn Phe Thr Val Ala Cys Gln His Arg Ser Asn Ser Glu Ile
                805                 810                 815
Ile Cys Cys Thr Thr Pro Ser Leu Gln Gln Leu Asn Leu Gln Leu Pro
                820                 825                 830
Leu Lys Thr Lys Ala Phe Phe Met Leu Asp Gly Ile Leu Ser Lys Tyr
            835                 840                 845
Phe Asp Leu Ile Tyr Val His Asn Pro Val Phe Lys Pro Phe Glu Lys
        850                 855                 860
Pro Val Met Ile Ser Met Gly Asn Glu Asn Val Leu Glu Ile Lys Gly
865                 870                 875                 880
Asn Asp Ile Asp Pro Glu Ala Val Lys Gly Glu Val Leu Lys Val Gly
                885                 890                 895
Asn Lys Ser Cys Glu Asn Ile His Leu His Ser Glu Ala Val Leu Cys
                900                 905                 910
Thr Val Pro Asn Asp Leu Leu Lys Leu Asn Ser Glu Leu Asn Ile Glu
            915                 920                 925
Trp Lys Gln Ala Ile Ser Thr Val Leu Gly Lys Val Ile Val Gln
        930                 935                 940
Pro Asp Gln Asn Phe Thr Gly Leu Ile Ala Gly Val Val Ser Ile Ser
945                 950                 955                 960
Thr Ala Leu Leu Leu Leu Gly Phe Phe Leu Trp Leu Lys Lys Arg
                965                 970                 975
Lys Gln Ile Lys Asp Leu Gly Ser Glu Leu Val Arg Tyr Asp Ala Arg
                980                 985                 990
Val His Thr Pro His Leu Asp Arg Leu Val Ser Ala Arg Ser Val Ser
            995                 1000                1005
Pro Thr Thr Glu Met Val Ser Asn Glu Ser Val Asp Tyr Arg Ala Thr
        1010                1015                1020
Phe Pro Glu Asp Gln Phe Pro Asn Ser Ser Gln Asn Gly Ser Cys Arg
1025                1030                1035                1040
Gln Val Gln Tyr Pro Leu Thr Asp Met Ser Pro Ile Leu Thr Ser Gly
                1045                1050                1055
```

```
Asp Ser Asp Ile Ser Ser Pro Leu Leu Gln Asn Thr Val His Ile Asp
            1060                1065                1070

Leu Ser Ala Leu Asn Pro Glu Leu Val Gln Ala Val Gln His Val Val
        1075                1080                1085

Ile Gly Pro Ser Ser Leu Ile Val His Phe Asn Glu Val Ile Gly Arg
    1090                1095                1100

Gly His Phe Gly Cys Val Tyr His Gly Thr Leu Leu Asp Asn Asp Gly
1105                1110                1115                1120

Lys Lys Ile His Cys Ala Val Lys Ser Leu Asn Arg Ile Thr Asp Ile
                1125                1130                1135

Gly Glu Val Ser Gln Phe Leu Thr Glu Gly Ile Ile Met Lys Asp Phe
            1140                1145                1150

Ser His Pro Asn Val Leu Ser Leu Leu Gly Ile Cys Leu Arg Ser Glu
        1155                1160                1165

Gly Ser Pro Leu Val Val Leu Pro Tyr Met Lys His Gly Asp Leu Arg
    1170                1175                1180

Asn Phe Ile Arg Asn Glu Thr His Asn Pro Thr Val Lys Asp Leu Ile
1185                1190                1195                1200

Gly Phe Gly Leu Gln Val Ala Lys Ala Met Lys Tyr Leu Ala Ser Lys
                1205                1210                1215

Lys Phe Val His Arg Asp Leu Ala Ala Arg Asn Cys Met Leu Asp Glu
            1220                1225                1230

Lys Phe Thr Val Lys Val Ala Asp Phe Gly Leu Ala Arg Asp Met Tyr
        1235                1240                1245

Asp Lys Glu Tyr Tyr Ser Val His Asn Lys Thr Gly Ala Lys Leu Pro
    1250                1255                1260

Val Lys Trp Met Ala Leu Glu Ser Leu Gln Thr Gln Lys Phe Thr Thr
1265                1270                1275                1280

Lys Ser Asp Val Trp Ser Phe Gly Val Val Leu Trp Glu Leu Met Thr
                1285                1290                1295

Arg Gly Ala Pro Pro Tyr Pro Asp Val Asn Thr Phe Asp Ile Thr Val
            1300                1305                1310

Tyr Leu Leu Gln Gly Arg Arg Leu Leu Gln Pro Glu Tyr Cys Pro Asp
        1315                1320                1325

Pro Leu Tyr Glu Val Met Leu Lys Cys Trp His Pro Lys Ala Glu Met
    1330                1335                1340

Arg Pro Ser Phe Ser Glu Leu Val Ser Arg Ile Ser Ala Ile Phe Ser
1345                1350                1355                1360

Thr Phe Ile Gly Glu His Tyr Val His Val Asn Ala Thr Tyr Val Asn
                1365                1370                1375

Val Lys Cys Val Ala Pro Tyr Pro Ser Leu Leu Ser Ser Glu Asp Asn
            1380                1385                1390

Ala Asp Asp Glu Val Asp Thr Arg Pro Ala Ser Phe Trp Glu Thr Ser
        1395                1400                1405

<210> SEQ ID NO 7
<211> LENGTH: 979
<212> TYPE: PRT
<213> ORGANISM: Artificial Sequence
<220> FEATURE:
<223> OTHER INFORMATION: CSF-MET fusion protein.

<400> SEQUENCE: 7

Met Gly Pro Gly Val Leu Leu Leu Leu Leu Val Ala Thr Ala Trp His
1               5                   10                  15
```

-continued

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

-continued

```
Gln Cys Ser Gly His Thr Asp Arg Cys Asp Glu Ala Gln Val Leu Gln
            435                 440                 445
Val Trp Asp Asp Pro Tyr Pro Glu Val Leu Ser Gln Glu Pro Phe His
        450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr Asp Leu Gly Lys Val
            500                 505                 510
Ile Val Gln Pro Asp Gln Asn Phe Thr Gly Leu Ile Ala Gly Val Val
        515                 520                 525
Ser Ile Ser Thr Ala Leu Leu Leu Leu Leu Gly Phe Phe Leu Trp Leu
530                 535                 540
Lys Lys Arg Lys Gln Ile Lys Asp Leu Gly Ser Glu Leu Val Arg Tyr
545                 550                 555                 560
Asp Ala Arg Val His Thr Pro His Leu Asp Arg Leu Val Ser Ala Arg
                565                 570                 575
Ser Val Ser Pro Thr Thr Glu Met Val Ser Asn Glu Ser Val Asp Tyr
            580                 585                 590
Arg Ala Thr Phe Pro Glu Asp Gln Phe Pro Asn Ser Ser Gln Asn Gly
        595                 600                 605
Ser Cys Arg Gln Val Gln Tyr Pro Leu Thr Asp Met Ser Pro Ile Leu
610                 615                 620
Thr Ser Gly Asp Ser Asp Ile Ser Ser Pro Leu Leu Gln Asn Thr Val
625                 630                 635                 640
His Ile Asp Leu Ser Ala Leu Asn Pro Glu Leu Val Gln Ala Val Gln
                645                 650                 655
His Val Val Ile Gly Pro Ser Ser Leu Ile Val His Phe Asn Glu Val
            660                 665                 670
Ile Gly Arg Gly His Phe Gly Cys Val Tyr His Gly Thr Leu Leu Asp
        675                 680                 685
Asn Asp Gly Lys Lys Ile His Cys Ala Val Lys Ser Leu Asn Arg Ile
690                 695                 700
Thr Asp Ile Gly Glu Val Ser Gln Phe Leu Thr Glu Gly Ile Ile Met
705                 710                 715                 720
Lys Asp Phe Ser His Pro Asn Val Leu Ser Leu Leu Gly Ile Cys Leu
                725                 730                 735
Arg Ser Glu Gly Ser Pro Leu Val Val Leu Pro Tyr Met Lys His Gly
            740                 745                 750
Asp Leu Arg Asn Phe Ile Arg Asn Glu Thr His Asn Pro Thr Val Lys
        755                 760                 765
Asp Leu Ile Gly Phe Gly Leu Gln Val Ala Lys Ala Met Lys Tyr Leu
770                 775                 780
Ala Ser Lys Lys Phe Val His Arg Asp Leu Ala Ala Arg Asn Cys Met
785                 790                 795                 800
Leu Asp Glu Lys Phe Thr Val Lys Val Ala Asp Phe Gly Leu Ala Arg
                805                 810                 815
Asp Met Tyr Asp Lys Glu Tyr Tyr Ser Val His Asn Lys Thr Gly Ala
            820                 825                 830
Lys Leu Pro Val Lys Trp Met Ala Leu Glu Ser Leu Gln Thr Gln Lys
        835                 840                 845
Phe Thr Thr Lys Ser Asp Val Trp Ser Phe Gly Val Val Leu Trp Glu
```

```
                    850                 855                 860
Leu Met Thr Arg Gly Ala Pro Pro Tyr Pro Asp Val Asn Thr Phe Asp
865                 870                 875                 880

Ile Thr Val Tyr Leu Leu Gln Gly Arg Arg Leu Leu Gln Pro Glu Tyr
                885                 890                 895

Cys Pro Asp Pro Leu Tyr Glu Val Met Leu Lys Cys Trp His Pro Lys
            900                 905                 910

Ala Glu Met Arg Pro Ser Phe Ser Glu Leu Val Ser Arg Ile Ser Ala
        915                 920                 925

Ile Phe Ser Thr Phe Ile Gly Glu His Tyr Val His Val Asn Ala Thr
    930                 935                 940

Tyr Val Asn Val Lys Cys Val Ala Pro Tyr Pro Ser Leu Leu Ser Ser
945                 950                 955                 960

Glu Asp Asn Ala Asp Asp Glu Val Asp Thr Arg Pro Ala Ser Phe Trp
                965                 970                 975

Glu Thr Ser

<210> SEQ ID NO 8
<211> LENGTH: 939
<212> TYPE: PRT
<213> ORGANISM: Homo sapiens

<400> SEQUENCE: 8

Met Asp Asp Ser Glu Val Glu Ser Thr Ala Ser Ile Leu Ala Ser Val
1               5                   10                  15

Lys Glu Gln Glu Ala Gln Phe Glu Lys Leu Thr Arg Ala Leu Glu Glu
            20                  25                  30

Glu Arg Arg His Val Ser Ala Gln Leu Glu Arg Val Arg Val Ser Pro
        35                  40                  45

Gln Asp Ala Asn Pro Leu Met Ala Asn Gly Thr Leu Thr Arg Arg His
    50                  55                  60

Gln Asn Gly Arg Phe Val Gly Asp Ala Asp Leu Glu Arg Gln Lys Phe
65                  70                  75                  80

Ser Asp Leu Lys Leu Asn Gly Pro Gln Asp His Ser His Leu Leu Tyr
                85                  90                  95

Ser Thr Ile Pro Arg Met Gln Glu Pro Gly Gln Ile Val Glu Thr Tyr
            100                 105                 110

Thr Glu Glu Asp Pro Glu Gly Ala Met Ser Val Val Ser Val Glu Thr
        115                 120                 125

Ser Asp Asp Gly Thr Thr Arg Arg Thr Glu Thr Thr Val Lys Lys Val
    130                 135                 140

Val Lys Thr Val Thr Thr Arg Thr Val Gln Pro Val Ala Met Gly Pro
145                 150                 155                 160

Asp Gly Leu Pro Val Asp Ala Ser Ser Val Ser Asn Asn Tyr Ile Gln
                165                 170                 175

Thr Leu Gly Arg Asp Phe Arg Lys Asn Gly Asn Gly Pro Gly Pro
            180                 185                 190

Tyr Val Gly Gln Ala Gly Thr Ala Thr Leu Pro Arg Asn Phe His Tyr
        195                 200                 205

Pro Pro Asp Gly Tyr Ser Arg His Tyr Glu Asp Gly Tyr Pro Gly Gly
    210                 215                 220

Ser Asp Asn Tyr Gly Ser Leu Ser Arg Val Thr Arg Ile Glu Glu Arg
225                 230                 235                 240

Tyr Arg Pro Ser Met Glu Gly Tyr Arg Ala Pro Ser Arg Gln Asp Val
```

-continued

```
                245                 250                 255
Tyr Gly Pro Gln Pro Gln Val Arg Val Gly Ser Ser Val Asp Leu
            260                 265                 270
His Arg Phe His Pro Glu Pro Tyr Gly Leu Glu Asp Asp Gln Arg Ser
        275                 280                 285
Met Gly Tyr Asp Asp Leu Asp Tyr Gly Met Met Ser Asp Tyr Gly Thr
        290                 295                 300
Ala Arg Arg Thr Gly Thr Pro Ser Asp Pro Arg Arg Leu Arg Ser
305                 310                 315                 320
Tyr Glu Asp Met Ile Gly Glu Glu Val Pro Ser Asp Gln Tyr Tyr Trp
                325                 330                 335
Ala Pro Leu Ala Gln His Glu Arg Gly Ser Leu Ala Ser Leu Asp Ser
                340                 345                 350
Leu Arg Lys Gly Gly Pro Pro Pro Asn Trp Arg Gln Pro Glu Leu
            355                 360                 365
Pro Glu Val Ile Ala Met Leu Gly Phe Arg Leu Asp Ala Val Lys Ser
            370                 375                 380
Asn Ala Ala Tyr Leu Gln His Leu Cys Tyr Arg Asn Asp Lys Val
385                 390                 395                 400
Lys Thr Asp Val Arg Lys Leu Lys Gly Ile Pro Val Leu Val Gly Leu
                405                 410                 415
Leu Asp His Pro Lys Lys Glu Val His Leu Gly Ala Cys Gly Ala Leu
            420                 425                 430
Lys Asn Ile Ser Phe Gly Arg Asp Gln Asp Asn Lys Ile Ala Ile Lys
            435                 440                 445
Asn Cys Asp Gly Val Pro Ala Leu Val Arg Leu Leu Arg Lys Ala Arg
450                 455                 460
Asp Met Asp Leu Thr Glu Val Ile Thr Gly Thr Leu Trp Asn Leu Ser
465                 470                 475                 480
Ser His Asp Ser Ile Lys Met Glu Ile Val Asp His Ala Leu His Ala
                485                 490                 495
Leu Thr Asp Glu Val Ile Ile Pro His Ser Gly Trp Glu Arg Glu Pro
            500                 505                 510
Asn Glu Asp Cys Lys Pro Arg His Ile Glu Trp Glu Ser Val Leu Thr
            515                 520                 525
Asn Thr Ala Gly Cys Leu Arg Asn Val Ser Ser Glu Arg Ser Glu Ala
            530                 535                 540
Arg Arg Lys Leu Arg Glu Cys Asp Gly Leu Val Asp Ala Leu Ile Phe
545                 550                 555                 560
Ile Val Gln Ala Glu Ile Gly Gln Lys Asp Ser Asp Ser Lys Leu Val
                565                 570                 575
Glu Asn Cys Val Cys Leu Leu Arg Asn Leu Ser Tyr Gln Val His Arg
                580                 585                 590
Glu Ile Pro Gln Ala Glu Arg Tyr Gln Glu Ala Ala Pro Asn Val Ala
            595                 600                 605
Asn Asn Thr Gly Pro His Ala Ala Ser Cys Phe Gly Ala Lys Lys Gly
            610                 615                 620
Lys Asp Glu Trp Phe Ser Arg Gly Lys Lys Pro Ile Glu Asp Pro Ala
625                 630                 635                 640
Asn Asp Thr Val Asp Phe Pro Lys Arg Thr Ser Pro Ala Arg Gly Tyr
                645                 650                 655
Glu Leu Leu Phe Gln Pro Glu Val Val Arg Ile Tyr Ile Ser Leu Leu
            660                 665                 670
```

-continued

Lys Glu Ser Lys Thr Pro Ala Ile Leu Glu Ala Ser Ala Gly Ala Ile
            675                 680                 685

Gln Asn Leu Cys Ala Gly Arg Trp Thr Tyr Gly Arg Tyr Ile Arg Ser
        690                 695                 700

Ala Leu Arg Gln Glu Lys Ala Leu Ser Ala Ile Ala Asp Leu Leu Thr
705                 710                 715                 720

Asn Glu His Glu Arg Val Val Lys Ala Ala Ser Gly Ala Leu Arg Asn
                725                 730                 735

Leu Ala Val Asp Ala Arg Asn Lys Glu Leu Ile Gly Lys His Ala Ile
            740                 745                 750

Pro Asn Leu Val Lys Asn Leu Pro Gly Gly Gln Gln Asn Ser Ser Trp
        755                 760                 765

Asn Phe Ser Glu Asp Thr Val Ile Ser Ile Leu Asn Thr Ile Asn Glu
    770                 775                 780

Val Ile Ala Glu Asn Leu Glu Ala Ala Lys Lys Leu Arg Glu Thr Gln
785                 790                 795                 800

Gly Ile Glu Lys Leu Val Leu Ile Asn Lys Ser Gly Asn Arg Ser Glu
                805                 810                 815

Lys Glu Val Arg Ala Ala Ala Leu Val Leu Gln Thr Ile Trp Gly Tyr
            820                 825                 830

Lys Glu Leu Arg Lys Pro Leu Glu Lys Glu Gly Trp Lys Lys Ser Asp
        835                 840                 845

Phe Gln Val Asn Leu Asn Asn Ala Ser Arg Ser Gln Ser Ser His Ser
    850                 855                 860

Tyr Asp Asp Ser Thr Leu Pro Leu Ile Asp Arg Asn Gln Lys Ser Asp
865                 870                 875                 880

Lys Lys Pro Asp Arg Glu Glu Ile Gln Met Ser Asn Met Gly Ser Asn
                885                 890                 895

Thr Lys Ser Leu Asp Asn Asn Tyr Ser Thr Pro Asn Glu Arg Gly Asp
            900                 905                 910

His Asn Arg Thr Leu Asp Arg Ser Gly Asp Leu Gly Asp Met Glu Pro
        915                 920                 925

Leu Lys Gly Thr Thr Pro Leu Met Gln Lys Ile
    930                 935

<210> SEQ ID NO 9
<211> LENGTH: 941
<212> TYPE: PRT
<213> ORGANISM: Homo sapiens

<400> SEQUENCE: 9

Met Asp Asp Ser Glu Val Glu Ser Thr Ala Ser Ile Leu Ala Ser Val
1               5                   10                  15

Lys Glu Gln Glu Ala Gln Phe Glu Lys Leu Thr Arg Ala Leu Glu Glu
                20                  25                  30

Glu Arg Arg His Val Ser Ala Gln Leu Glu Arg Val Arg Val Ser Pro
            35                  40                  45

Gln Asp Ala Asn Pro Leu Met Ala Asn Gly Thr Leu Thr Arg Arg His
        50                  55                  60

Gln Asn Gly Arg Phe Val Gly Asp Ala Asp Leu Glu Arg Gln Lys Phe
65                  70                  75                  80

Ser Asp Leu Lys Leu Asn Gly Pro Gln Asp His Ser His Leu Leu Tyr
                85                  90                  95

Ser Thr Ile Pro Arg Met Gln Glu Pro Gly Gln Ile Val Glu Thr Tyr

-continued

```
                100             105             110
Thr Glu Glu Asp Pro Glu Gly Ala Met Ser Val Val Ser Val Glu Thr
            115                 120                 125

Ser Asp Asp Gly Thr Thr Arg Arg Thr Glu Thr Thr Val Lys Lys Val
            130                 135                 140

Val Lys Thr Val Thr Thr Arg Thr Val Gln Pro Val Ala Met Gly Pro
145                 150                 155                 160

Asp Gly Leu Pro Val Asp Ala Ser Ser Val Ser Asn Asn Tyr Ile Gln
                        165                 170                 175

Thr Leu Gly Arg Asp Phe Arg Lys Asn Gly Asn Gly Pro Gly Pro
                    180                 185                 190

Tyr Val Gly Gln Ala Gly Thr Ala Thr Leu Pro Arg Asn Phe His Tyr
        195                 200                 205

Pro Pro Asp Gly Tyr Ser Arg His Tyr Glu Asp Gly Tyr Pro Gly Gly
            210                 215                 220

Ser Asp Asn Tyr Gly Ser Leu Ser Arg Val Thr Arg Ile Glu Glu Arg
225                 230                 235                 240

Tyr Arg Pro Ser Met Glu Gly Tyr Arg Ala Pro Ser Arg Gln Asp Val
                        245                 250                 255

Tyr Gly Pro Gln Pro Gln Val Arg Val Gly Ser Ser Val Asp Leu
                    260                 265                 270

His Arg Phe His Pro Glu Pro Tyr Gly Leu Glu Asp Gln Arg Ser
        275                 280                 285

Met Gly Tyr Asp Asp Leu Asp Tyr Gly Met Met Ser Asp Tyr Gly Thr
            290                 295                 300

Ala Arg Arg Thr Gly Thr Pro Ser Asp Pro Arg Arg Leu Arg Ser
305                 310                 315                 320

Tyr Glu Asp Met Ile Gly Glu Val Pro Ser Asp Gln Tyr Tyr Trp
                        325                 330                 335

Ala Pro Leu Ala Gln His Glu Arg Gly Ser Leu Ala Ser Leu Asp Ser
                    340                 345                 350

Leu Arg Lys Gly Gly Pro Pro Pro Asn Trp Arg Gln Pro Glu Leu
        355                 360                 365

Pro Glu Val Ile Ala Met Leu Gly Phe Arg Leu Asp Ala Val Lys Ser
            370                 375                 380

Asn Ala Ala Tyr Leu Gln His Leu Cys Tyr Arg Asn Asp Lys Val
385                 390                 395                 400

Lys Thr Asp Val Arg Lys Leu Lys Gly Ile Pro Val Leu Val Gly Leu
                        405                 410                 415

Leu Asp His Pro Lys Lys Glu Val His Leu Gly Ala Cys Gly Ala Leu
                    420                 425                 430

Lys Asn Ile Ser Phe Gly Arg Asp Gln Asp Asn Lys Ile Ala Ile Lys
        435                 440                 445

Asn Cys Asp Gly Val Pro Ala Leu Val Arg Leu Leu Arg Lys Ala Arg
            450                 455                 460

Asp Met Asp Leu Thr Glu Val Ile Thr Gly Thr Leu Trp Asn Leu Ser
465                 470                 475                 480

Ser His Asp Ser Ile Lys Met Glu Ile Val Asp His Ala Leu His Ala
                        485                 490                 495

Leu Thr Asp Glu Val Ile Ile Pro His Ser Gly Trp Glu Arg Glu Pro
                    500                 505                 510

Asn Glu Asp Cys Lys Pro Arg His Ile Glu Trp Glu Ser Val Leu Thr
        515                 520                 525
```

```
Asn Thr Ala Gly Cys Leu Arg Asn Val Ser Ser Glu Arg Ser Glu Ala
            530                 535                 540

Arg Arg Lys Leu Arg Glu Cys Asp Gly Leu Val Asp Ala Leu Ile Phe
545                 550                 555                 560

Ile Val Gln Ala Glu Ile Gly Gln Lys Asp Ser Asp Ser Lys Leu Val
                565                 570                 575

Glu Asn Cys Val Cys Leu Leu Arg Asn Leu Ser Tyr Gln Val His Arg
            580                 585                 590

Glu Ile Pro Gln Ala Glu Arg Tyr Gln Glu Ala Ala Pro Asn Val Ala
            595                 600                 605

Asn Asn Thr Gly Pro His Ala Ala Ser Cys Phe Gly Ala Lys Lys Gly
            610                 615                 620

Lys Gly Lys Lys Pro Ile Glu Asp Pro Ala Asn Asp Thr Val Asp Phe
625                 630                 635                 640

Pro Lys Arg Thr Ser Pro Ala Arg Gly Tyr Glu Leu Leu Phe Gln Pro
                645                 650                 655

Glu Val Val Arg Ile Tyr Ile Ser Leu Leu Lys Glu Ser Lys Thr Pro
            660                 665                 670

Ala Ile Leu Glu Ala Ser Ala Gly Ala Ile Gln Asn Leu Cys Ala Gly
            675                 680                 685

Arg Trp Thr Tyr Gly Arg Tyr Ile Arg Ser Ala Leu Arg Gln Glu Lys
            690                 695                 700

Ala Leu Ser Ala Ile Ala Asp Leu Leu Thr Asn Glu His Glu Arg Val
705                 710                 715                 720

Val Lys Ala Ala Ser Gly Ala Leu Arg Asn Leu Ala Val Asp Ala Arg
                725                 730                 735

Asn Lys Glu Leu Ile Gly Lys His Ala Ile Pro Asn Leu Val Lys Asn
            740                 745                 750

Leu Pro Gly Gly Gln Gln Asn Ser Ser Trp Asn Phe Ser Glu Asp Thr
            755                 760                 765

Val Ile Ser Ile Leu Asn Thr Ile Asn Glu Val Ile Ala Glu Asn Leu
770                 775                 780

Glu Ala Ala Lys Lys Leu Arg Glu Thr Gln Gly Ile Glu Lys Leu Val
785                 790                 795                 800

Leu Ile Asn Lys Ser Gly Asn Arg Ser Glu Lys Glu Val Arg Ala Ala
                805                 810                 815

Ala Leu Val Leu Gln Thr Ile Trp Gly Tyr Lys Glu Leu Arg Lys Pro
            820                 825                 830

Leu Glu Lys Glu Gly Trp Lys Lys Ser Asp Phe Gln Val Asn Leu Asn
            835                 840                 845

Asn Ala Ser Arg Ser Gln Ser Ser His Ser Tyr Asp Asp Ser Thr Leu
850                 855                 860

Pro Leu Ile Asp Arg Asn Gln Lys Ser Asp Asn Asn Tyr Ser Thr Pro
865                 870                 875                 880

Asn Glu Arg Gly Asp His Asn Arg Thr Leu Asp Arg Ser Gly Asp Leu
                885                 890                 895

Gly Asp Met Glu Pro Leu Lys Gly Thr Thr Pro Leu Met Gln Asp Glu
            900                 905                 910

Gly Gln Glu Ser Leu Glu Glu Leu Asp Val Leu Val Leu Asp Asp
            915                 920                 925

Glu Gly Gly Gln Val Ser Tyr Pro Ser Met Gln Lys Ile
930                 935                 940
```

```
<210> SEQ ID NO 10
<211> LENGTH: 914
<212> TYPE: PRT
<213> ORGANISM: Homo sapiens

<400> SEQUENCE: 10
```

| | | | | | | | | | | | | | | |
|---|---|---|---|---|---|---|---|---|---|---|---|---|---|---|
| Met | Ala | Asn | Gly | Thr | Leu | Thr | Arg | Arg | His | Gln | Asn | Gly | Arg | Phe | Val |
| 1 | | | | 5 | | | | | 10 | | | | | 15 |
| Gly | Asp | Ala | Asp | Leu | Glu | Arg | Gln | Lys | Phe | Ser | Asp | Leu | Lys | Leu | Asn |
| | | | 20 | | | | | 25 | | | | | 30 | | |
| Gly | Pro | Gln | Asp | His | Ser | His | Leu | Leu | Tyr | Ser | Thr | Ile | Pro | Arg | Met |
| | | 35 | | | | | 40 | | | | | 45 | | | |
| Gln | Glu | Pro | Gly | Gln | Ile | Val | Glu | Thr | Tyr | Thr | Glu | Glu | Asp | Pro | Glu |
| | 50 | | | | | 55 | | | | | 60 | | | | |
| Gly | Ala | Met | Ser | Val | Val | Ser | Val | Glu | Thr | Ser | Asp | Asp | Gly | Thr | Thr |
| 65 | | | | | 70 | | | | | 75 | | | | | 80 |
| Arg | Arg | Thr | Glu | Thr | Thr | Val | Lys | Lys | Val | Val | Lys | Thr | Val | Thr | Thr |
| | | | | 85 | | | | | 90 | | | | | 95 | |
| Arg | Thr | Val | Gln | Pro | Val | Ala | Met | Gly | Pro | Asp | Gly | Leu | Pro | Val | Asp |
| | | | 100 | | | | | 105 | | | | | 110 | | |
| Ala | Ser | Ser | Val | Ser | Asn | Asn | Tyr | Ile | Gln | Thr | Leu | Gly | Arg | Asp | Phe |
| | | 115 | | | | | 120 | | | | | 125 | | | |
| Arg | Lys | Asn | Gly | Asn | Gly | Gly | Pro | Gly | Pro | Tyr | Val | Gly | Gln | Ala | Gly |
| | 130 | | | | | 135 | | | | | 140 | | | | |
| Thr | Ala | Thr | Leu | Pro | Arg | Asn | Phe | His | Tyr | Pro | Pro | Asp | Gly | Tyr | Ser |
| 145 | | | | | 150 | | | | | 155 | | | | | 160 |
| Arg | His | Tyr | Glu | Asp | Gly | Tyr | Pro | Gly | Gly | Ser | Asp | Asn | Tyr | Gly | Ser |
| | | | | 165 | | | | | 170 | | | | | 175 | |
| Leu | Ser | Arg | Val | Thr | Arg | Ile | Glu | Glu | Arg | Tyr | Arg | Pro | Ser | Met | Glu |
| | | | 180 | | | | | 185 | | | | | 190 | | |
| Gly | Tyr | Arg | Ala | Pro | Ser | Arg | Gln | Asp | Val | Tyr | Gly | Pro | Gln | Pro | Gln |
| | | 195 | | | | | 200 | | | | | 205 | | | |
| Val | Arg | Val | Gly | Gly | Ser | Ser | Val | Asp | Leu | His | Arg | Phe | His | Pro | Glu |
| | 210 | | | | | 215 | | | | | 220 | | | | |
| Pro | Tyr | Gly | Leu | Glu | Asp | Asp | Gln | Arg | Ser | Met | Gly | Tyr | Asp | Asp | Leu |
| 225 | | | | | 230 | | | | | 235 | | | | | 240 |
| Asp | Tyr | Gly | Met | Met | Ser | Asp | Tyr | Gly | Thr | Ala | Arg | Arg | Thr | Gly | Thr |
| | | | | 245 | | | | | 250 | | | | | 255 | |
| Pro | Ser | Asp | Pro | Arg | Arg | Arg | Leu | Arg | Ser | Tyr | Glu | Asp | Met | Ile | Gly |
| | | | 260 | | | | | 265 | | | | | 270 | | |
| Glu | Glu | Val | Pro | Ser | Asp | Gln | Tyr | Tyr | Trp | Ala | Pro | Leu | Ala | Gln | His |
| | | 275 | | | | | 280 | | | | | 285 | | | |
| Glu | Arg | Gly | Ser | Leu | Ala | Ser | Leu | Asp | Ser | Leu | Arg | Lys | Gly | Gly | Pro |
| | 290 | | | | | 295 | | | | | 300 | | | | |
| Pro | Pro | Pro | Asn | Trp | Arg | Gln | Pro | Glu | Leu | Pro | Glu | Val | Ile | Ala | Met |
| 305 | | | | | 310 | | | | | 315 | | | | | 320 |
| Leu | Gly | Phe | Arg | Leu | Asp | Ala | Val | Lys | Ser | Asn | Ala | Ala | Ala | Tyr | Leu |
| | | | | 325 | | | | | 330 | | | | | 335 | |
| Gln | His | Leu | Cys | Tyr | Arg | Asn | Asp | Lys | Val | Lys | Thr | Asp | Val | Arg | Lys |
| | | | 340 | | | | | 345 | | | | | 350 | | |
| Leu | Lys | Gly | Ile | Pro | Val | Leu | Val | Gly | Leu | Leu | Asp | His | Pro | Lys | Lys |
| | | 355 | | | | | 360 | | | | | 365 | | | |
| Glu | Val | His | Leu | Gly | Ala | Cys | Gly | Ala | Leu | Lys | Asn | Ile | Ser | Phe | Gly |
| | 370 | | | | | 375 | | | | | 380 | | | | |

```
Arg Asp Gln Asp Asn Lys Ile Ala Ile Lys Asn Cys Asp Gly Val Pro
385                 390                 395                 400

Ala Leu Val Arg Leu Leu Arg Lys Ala Arg Asp Met Asp Leu Thr Glu
            405                 410                 415

Val Ile Thr Gly Thr Leu Trp Asn Leu Ser Ser His Asp Ser Ile Lys
            420                 425                 430

Met Glu Ile Val Asp His Ala Leu His Ala Leu Thr Asp Glu Val Ile
        435                 440                 445

Ile Pro His Ser Gly Trp Glu Arg Pro Asn Glu Asp Cys Lys Pro
    450                 455                 460

Arg His Ile Glu Trp Glu Ser Val Leu Thr Asn Thr Ala Gly Cys Leu
465             470                 475                 480

Arg Asn Val Ser Ser Glu Arg Ser Glu Ala Arg Arg Lys Leu Arg Glu
                485                 490                 495

Cys Asp Gly Leu Val Asp Ala Leu Ile Phe Ile Val Gln Ala Glu Ile
            500                 505                 510

Gly Gln Lys Asp Ser Asp Ser Lys Leu Val Glu Asn Cys Val Cys Leu
            515                 520                 525

Leu Arg Asn Leu Ser Tyr Gln Val His Arg Glu Ile Pro Gln Ala Glu
530                 535                 540

Arg Tyr Gln Glu Ala Ala Pro Asn Val Ala Asn Thr Gly Pro His
545             550                 555                 560

Ala Ala Ser Cys Phe Gly Ala Lys Lys Gly Lys Asp Glu Trp Phe Ser
                565                 570                 575

Arg Gly Lys Lys Pro Ile Glu Asp Pro Ala Asn Asp Thr Val Asp Phe
            580                 585                 590

Pro Lys Arg Thr Ser Pro Ala Arg Gly Tyr Glu Leu Leu Phe Gln Pro
            595                 600                 605

Glu Val Val Arg Ile Tyr Ile Ser Leu Leu Lys Glu Ser Lys Thr Pro
610                 615                 620

Ala Ile Leu Glu Ala Ser Ala Gly Ala Ile Gln Asn Leu Cys Ala Gly
625                 630                 635                 640

Arg Trp Thr Tyr Gly Arg Tyr Ile Arg Ser Ala Leu Arg Gln Glu Lys
            645                 650                 655

Ala Leu Ser Ala Ile Ala Asp Leu Leu Thr Asn Glu His Glu Arg Val
            660                 665                 670

Val Lys Ala Ala Ser Gly Ala Leu Arg Asn Leu Ala Val Asp Ala Arg
        675                 680                 685

Asn Lys Glu Leu Ile Gly Lys His Ala Ile Pro Asn Leu Val Lys Asn
    690                 695                 700

Leu Pro Gly Gly Gln Gln Asn Ser Ser Trp Asn Phe Ser Glu Asp Thr
705                 710                 715                 720

Val Ile Ser Ile Leu Asn Thr Ile Asn Glu Val Ile Ala Glu Asn Leu
            725                 730                 735

Glu Ala Ala Lys Lys Leu Arg Glu Thr Gln Gly Ile Glu Lys Leu Val
            740                 745                 750

Leu Ile Asn Lys Ser Gly Asn Arg Ser Glu Lys Glu Val Arg Ala Ala
            755                 760                 765

Ala Leu Val Leu Gln Thr Ile Trp Gly Tyr Lys Glu Leu Arg Lys Pro
        770                 775                 780

Leu Glu Lys Glu Gly Trp Lys Lys Ser Asp Phe Gln Val Asn Leu Asn
785                 790                 795                 800
```

-continued

```
Asn Ala Ser Arg Ser Gln Ser His Ser Tyr Asp Ser Thr Leu
            805                 810                 815

Pro Leu Ile Asp Arg Asn Gln Lys Ser Asp Lys Pro Asp Arg Glu
            820                 825                 830

Glu Ile Gln Met Ser Asn Met Gly Ser Asn Thr Lys Ser Leu Asp Asn
            835                 840                 845

Asn Tyr Ser Thr Pro Asn Glu Arg Gly Asp His Asn Arg Thr Leu Asp
            850                 855                 860

Arg Ser Gly Asp Leu Gly Asp Met Glu Pro Leu Lys Gly Thr Thr Pro
865                 870                 875                 880

Leu Met Gln Asp Glu Gly Gln Glu Ser Leu Glu Glu Leu Asp Val
                    885                 890                 895

Leu Val Leu Asp Asp Glu Gly Gly Gln Val Ser Tyr Pro Ser Met Gln
                    900                 905                 910

Lys Ile
```

<210> SEQ ID NO 11
<211> LENGTH: 861
<212> TYPE: PRT
<213> ORGANISM: Homo sapiens

<400> SEQUENCE: 11

```
Met Gln Glu Pro Gly Gln Ile Val Glu Thr Tyr Thr Glu Glu Asp Pro
1               5                   10                  15

Glu Gly Ala Met Ser Val Val Ser Val Glu Thr Ser Asp Asp Gly Thr
                20                  25                  30

Thr Arg Arg Thr Glu Thr Thr Val Lys Lys Val Val Lys Thr Val Thr
            35                  40                  45

Thr Arg Thr Val Gln Pro Val Ala Met Gly Pro Asp Gly Leu Pro Val
        50                  55                  60

Asp Ala Ser Ser Val Ser Asn Asn Tyr Ile Gln Thr Leu Gly Arg Asp
65                  70                  75                  80

Phe Arg Lys Asn Gly Asn Gly Pro Gly Pro Tyr Val Gly Gln Ala
                85                  90                  95

Gly Thr Ala Thr Leu Pro Arg Asn Phe His Tyr Pro Pro Asp Gly Tyr
                100                 105                 110

Ser Arg His Tyr Glu Asp Gly Tyr Pro Gly Gly Ser Asp Asn Tyr Gly
            115                 120                 125

Ser Leu Ser Arg Val Thr Arg Ile Glu Glu Arg Tyr Arg Pro Ser Met
        130                 135                 140

Glu Gly Tyr Arg Ala Pro Ser Arg Gln Asp Val Tyr Gly Pro Gln Pro
145                 150                 155                 160

Gln Val Arg Val Gly Gly Ser Ser Val Asp Leu His Arg Phe His Pro
                165                 170                 175

Glu Pro Tyr Gly Leu Glu Asp Asp Gln Arg Ser Met Gly Tyr Asp Asp
                180                 185                 190

Leu Asp Tyr Gly Met Met Ser Asp Tyr Gly Thr Ala Arg Arg Thr Gly
            195                 200                 205

Thr Pro Ser Asp Pro Arg Arg Arg Leu Arg Ser Tyr Glu Asp Met Ile
        210                 215                 220

Gly Glu Glu Val Pro Ser Asp Gln Tyr Tyr Trp Ala Pro Leu Ala Gln
225                 230                 235                 240

His Glu Arg Gly Ser Leu Ala Ser Leu Asp Ser Leu Arg Lys Gly Gly
                245                 250                 255
```

-continued

Pro Pro Pro Pro Asn Trp Arg Gln Pro Glu Leu Pro Glu Val Ile Ala
            260                 265                 270

Met Leu Gly Phe Arg Leu Asp Ala Val Lys Ser Asn Ala Ala Ala Tyr
            275                 280                 285

Leu Gln His Leu Cys Tyr Arg Asn Asp Lys Val Lys Thr Asp Val Arg
            290                 295                 300

Lys Leu Lys Gly Ile Pro Val Leu Val Gly Leu Leu Asp His Pro Lys
305                 310                 315                 320

Lys Glu Val His Leu Gly Ala Cys Gly Ala Leu Lys Asn Ile Ser Phe
            325                 330                 335

Gly Arg Asp Gln Asp Asn Lys Ile Ala Ile Lys Asn Cys Asp Gly Val
            340                 345                 350

Pro Ala Leu Val Arg Leu Leu Arg Lys Ala Arg Asp Met Asp Leu Thr
            355                 360                 365

Glu Val Ile Thr Gly Thr Leu Trp Asn Leu Ser Ser His Asp Ser Ile
            370                 375                 380

Lys Met Glu Ile Val Asp His Ala Leu His Ala Leu Thr Asp Glu Val
385                 390                 395                 400

Ile Ile Pro His Ser Gly Trp Glu Arg Glu Pro Asn Glu Asp Cys Lys
            405                 410                 415

Pro Arg His Ile Glu Trp Glu Ser Val Leu Thr Asn Thr Ala Gly Cys
            420                 425                 430

Leu Arg Asn Val Ser Ser Glu Arg Ser Glu Ala Arg Arg Lys Leu Arg
            435                 440                 445

Glu Cys Asp Gly Leu Val Asp Ala Leu Ile Phe Ile Val Gln Ala Glu
            450                 455                 460

Ile Gly Gln Lys Asp Ser Asp Ser Lys Leu Val Glu Asn Cys Val Cys
465                 470                 475                 480

Leu Leu Arg Asn Leu Ser Tyr Gln Val His Arg Glu Ile Pro Gln Ala
            485                 490                 495

Glu Arg Tyr Gln Glu Ala Ala Pro Asn Val Ala Asn Asn Thr Gly Pro
            500                 505                 510

His Ala Ala Ser Cys Phe Gly Ala Lys Lys Gly Lys Gly Lys Lys Pro
            515                 520                 525

Ile Glu Asp Pro Ala Asn Asp Thr Val Asp Phe Pro Lys Arg Thr Ser
            530                 535                 540

Pro Ala Arg Gly Tyr Glu Leu Leu Phe Gln Pro Glu Val Val Arg Ile
545                 550                 555                 560

Tyr Ile Ser Leu Leu Lys Glu Ser Lys Thr Pro Ala Ile Leu Glu Ala
            565                 570                 575

Ser Ala Gly Ala Ile Gln Asn Leu Cys Ala Gly Arg Trp Thr Tyr Gly
            580                 585                 590

Arg Tyr Ile Arg Ser Ala Leu Arg Gln Glu Lys Ala Leu Ser Ala Ile
            595                 600                 605

Ala Asp Leu Leu Thr Asn Glu His Glu Arg Val Val Lys Ala Ala Ser
            610                 615                 620

Gly Ala Leu Arg Asn Leu Ala Val Asp Ala Arg Asn Lys Glu Leu Ile
625                 630                 635                 640

Gly Lys His Ala Ile Pro Asn Leu Val Lys Asn Leu Pro Gly Gly Gln
            645                 650                 655

Gln Asn Ser Ser Trp Asn Phe Ser Glu Asp Thr Val Ile Ser Ile Leu
            660                 665                 670

Asn Thr Ile Asn Glu Val Ile Ala Glu Asn Leu Glu Ala Ala Lys Lys

-continued

```
            675                 680                 685
Leu Arg Glu Thr Gln Gly Ile Glu Lys Leu Val Leu Ile Asn Lys Ser
    690                 695                 700

Gly Asn Arg Ser Glu Lys Glu Val Arg Ala Ala Ala Leu Val Leu Gln
705                 710                 715                 720

Thr Ile Trp Gly Tyr Lys Glu Leu Arg Lys Pro Leu Glu Lys Glu Gly
                725                 730                 735

Trp Lys Lys Ser Asp Phe Gln Val Asn Leu Asn Asn Ala Ser Arg Ser
                740                 745                 750

Gln Ser Ser His Ser Tyr Asp Asp Ser Thr Leu Pro Leu Ile Asp Arg
    755                 760                 765

Asn Gln Lys Ser Asp Lys Lys Pro Asp Arg Glu Glu Ile Gln Met Ser
    770                 775                 780

Asn Met Gly Ser Asn Thr Lys Ser Leu Asp Asn Asn Tyr Ser Thr Pro
785                 790                 795                 800

Asn Glu Arg Gly Asp His Asn Arg Thr Leu Asp Arg Ser Gly Asp Leu
                805                 810                 815

Gly Asp Met Glu Pro Leu Lys Gly Thr Thr Pro Leu Met Gln Asp Glu
                820                 825                 830

Gly Gln Glu Ser Leu Glu Glu Leu Asp Val Leu Val Leu Asp Asp
    835                 840                 845

Glu Gly Gly Gln Val Ser Tyr Pro Ser Met Gln Lys Ile
    850                 855                 860

<210> SEQ ID NO 12
<211> LENGTH: 645
<212> TYPE: PRT
<213> ORGANISM: Homo sapiens

<400> SEQUENCE: 12

Met Ile Gly Glu Glu Val Pro Ser Asp Gln Tyr Tyr Trp Ala Pro Leu
1               5                   10                  15

Ala Gln His Glu Arg Gly Ser Leu Ala Ser Leu Asp Ser Leu Arg Lys
                20                  25                  30

Gly Gly Pro Pro Pro Asn Trp Arg Gln Pro Glu Leu Pro Glu Val
            35                  40                  45

Ile Ala Met Leu Gly Phe Arg Leu Asp Ala Val Lys Ser Asn Ala Ala
    50                  55                  60

Ala Tyr Leu Gln His Leu Cys Tyr Arg Asn Asp Lys Val Lys Thr Asp
65                  70                  75                  80

Val Arg Lys Leu Lys Gly Ile Pro Val Leu Val Gly Leu Leu Asp His
                85                  90                  95

Pro Lys Lys Glu Val His Leu Gly Ala Cys Gly Ala Leu Lys Asn Ile
                100                 105                 110

Ser Phe Gly Arg Asp Gln Asp Asn Lys Ile Ala Ile Lys Asn Cys Asp
            115                 120                 125

Gly Val Pro Ala Leu Val Arg Leu Leu Arg Lys Ala Arg Asp Met Asp
130                 135                 140

Leu Thr Glu Val Ile Thr Gly Thr Leu Trp Asn Leu Ser Ser His Asp
145                 150                 155                 160

Ser Ile Lys Met Glu Ile Val Asp His Ala Leu His Ala Leu Thr Asp
                165                 170                 175

Glu Val Ile Ile Pro His Ser Gly Trp Glu Arg Glu Pro Asn Glu Asp
                180                 185                 190
```

```
Cys Lys Pro Arg His Ile Glu Trp Glu Ser Val Leu Thr Asn Thr Ala
        195                 200                 205
Gly Cys Leu Arg Asn Val Ser Ser Glu Arg Ser Glu Ala Arg Arg Lys
    210                 215                 220
Leu Arg Glu Cys Asp Gly Leu Val Asp Ala Leu Ile Phe Ile Val Gln
225                 230                 235                 240
Ala Glu Ile Gly Gln Lys Asp Ser Asp Ser Lys Leu Val Glu Asn Cys
                245                 250                 255
Val Cys Leu Leu Arg Asn Leu Ser Tyr Gln Val His Arg Glu Ile Pro
            260                 265                 270
Gln Ala Glu Arg Tyr Gln Glu Ala Pro Asn Val Ala Asn Asn Thr
        275                 280                 285
Gly Pro His Ala Ala Ser Cys Phe Gly Ala Lys Gly Lys Asp Glu
290                 295                 300
Trp Phe Ser Arg Gly Lys Lys Pro Ile Glu Asp Pro Ala Asn Asp Thr
305                 310                 315                 320
Val Asp Phe Pro Lys Arg Thr Ser Pro Ala Arg Gly Tyr Glu Leu Leu
                325                 330                 335
Phe Gln Pro Glu Val Val Arg Ile Tyr Ile Ser Leu Leu Lys Glu Ser
            340                 345                 350
Lys Thr Pro Ala Ile Leu Glu Ala Ser Ala Gly Ala Ile Gln Asn Leu
        355                 360                 365
Cys Ala Gly Arg Trp Thr Tyr Gly Arg Tyr Ile Arg Ser Ala Leu Arg
    370                 375                 380
Gln Glu Lys Ala Leu Ser Ala Ile Ala Asp Leu Leu Thr Asn Glu His
385                 390                 395                 400
Glu Arg Val Val Lys Ala Ala Ser Gly Ala Leu Arg Asn Leu Ala Val
                405                 410                 415
Asp Ala Arg Asn Lys Glu Leu Ile Gly Lys His Ala Ile Pro Asn Leu
            420                 425                 430
Val Lys Asn Leu Pro Gly Gly Gln Gln Asn Ser Ser Trp Asn Phe Ser
        435                 440                 445
Glu Asp Thr Val Ile Ser Ile Leu Asn Thr Ile Asn Glu Val Ile Ala
    450                 455                 460
Glu Asn Leu Glu Ala Ala Lys Lys Leu Arg Glu Thr Gln Gly Ile Glu
465                 470                 475                 480
Lys Leu Val Leu Ile Asn Lys Ser Gly Asn Arg Ser Glu Lys Glu Val
                485                 490                 495
Arg Ala Ala Ala Leu Val Leu Gln Thr Ile Trp Gly Tyr Lys Glu Leu
            500                 505                 510
Arg Lys Pro Leu Glu Lys Glu Gly Trp Lys Lys Ser Asp Phe Gln Val
        515                 520                 525
Asn Leu Asn Asn Ala Ser Arg Ser Gln Ser Ser His Ser Tyr Asp Asp
    530                 535                 540
Ser Thr Leu Pro Leu Ile Asp Arg Asn Gln Lys Ser Asp Lys Pro
545                 550                 555                 560
Asp Arg Glu Glu Ile Gln Met Ser Asn Met Gly Ser Asn Thr Lys Ser
                565                 570                 575
Leu Asp Asn Asn Tyr Ser Thr Pro Asn Glu Arg Gly Asp His Asn Arg
            580                 585                 590
Thr Leu Asp Arg Ser Gly Asp Leu Gly Asp Met Glu Pro Leu Lys Gly
        595                 600                 605
Thr Thr Pro Leu Met Gln Asp Glu Gly Gln Glu Ser Leu Glu Glu Glu
```

```
                      610                 615                 620
Leu Asp Val Leu Val Leu Asp Asp Glu Gly Gly Gln Val Ser Tyr Pro
625                 630                 635                 640

Ser Met Gln Lys Ile
            645

<210> SEQ ID NO 13
<211> LENGTH: 694
<212> TYPE: PRT
<213> ORGANISM: Homo sapiens

<400> SEQUENCE: 13

Met Ser Gly Gly Glu Val Val Cys Ser Gly Trp Leu Arg Lys Ser Pro
1               5                   10                  15

Pro Glu Lys Lys Leu Lys Arg Tyr Ala Trp Lys Arg Arg Trp Phe Val
            20                  25                  30

Leu Arg Ser Gly Arg Leu Thr Gly Asp Pro Asp Val Leu Glu Tyr Tyr
        35                  40                  45

Lys Asn Asp His Ala Lys Lys Pro Ile Arg Ile Ile Asp Leu Asn Leu
50                  55                  60

Cys Gln Gln Val Asp Ala Gly Leu Thr Phe Asn Lys Lys Glu Phe Glu
65                  70                  75                  80

Asn Ser Tyr Ile Phe Asp Ile Asn Thr Ile Asp Arg Ile Phe Tyr Leu
                85                  90                  95

Val Ala Asp Ser Glu Glu Glu Met Asn Lys Trp Val Arg Cys Ile Cys
            100                 105                 110

Asp Ile Cys Gly Phe Asn Pro Thr Glu Glu Asp Pro Val Lys Pro Pro
        115                 120                 125

Gly Ser Ser Leu Gln Ala Pro Ala Asp Leu Pro Leu Ala Ile Asn Thr
130                 135                 140

Ala Pro Pro Ser Thr Gln Ala Asp Ser Ser Ala Thr Leu Pro Pro
145                 150                 155                 160

Pro Tyr Gln Leu Ile Asn Val Pro Pro His Leu Glu Thr Leu Gly Ile
                165                 170                 175

Gln Glu Asp Pro Gln Asp Tyr Leu Leu Leu Ile Asn Cys Gln Ser Lys
            180                 185                 190

Lys Pro Glu Pro Thr Arg Thr His Ala Asp Ser Gly Lys Ser Thr Ser
        195                 200                 205

Ser Glu Thr Asp Ser Asn Asp Asn Val Pro Ser His Lys Asn Pro Ala
210                 215                 220

Ser Ser Gln Ser Lys His Gly Met Asn Gly Phe Phe Gln Gln Gln Met
225                 230                 235                 240

Ile Tyr Asp Ser Pro Pro Ser Arg Ala Pro Ser Ala Ser Val Asp Ser
                245                 250                 255

Ser Leu Tyr Asn Leu Pro Arg Ser Tyr Ser His Asp Val Leu Pro Lys
            260                 265                 270

Val Ser Pro Ser Ser Thr Glu Ala Asp Gly Glu Leu Tyr Val Phe Asn
        275                 280                 285

Thr Pro Ser Gly Thr Ser Val Glu Thr Gln Met Arg His Val Ser
290                 295                 300

Ile Ser Tyr Asp Ile Pro Pro Thr Pro Gly Asn Thr Tyr Gln Ile Pro
305                 310                 315                 320

Arg Thr Phe Pro Glu Gly Thr Leu Gly Gln Thr Ser Lys Leu Asp Thr
                325                 330                 335
```

```
Ile Pro Asp Ile Pro Pro Arg Pro Lys Pro His Pro Ala His
            340                 345                 350

Asp Arg Ser Pro Val Glu Thr Cys Ser Ile Pro Arg Thr Ala Ser Asp
        355                 360                 365

Thr Asp Ser Ser Tyr Cys Ile Pro Thr Ala Gly Met Ser Pro Ser Arg
    370                 375                 380

Ser Asn Thr Ile Ser Thr Val Asp Leu Asn Lys Leu Arg Lys Asp Ala
385                 390                 395                 400

Ser Ser Gln Asp Cys Tyr Asp Ile Pro Arg Ala Phe Pro Ser Asp Arg
            405                 410                 415

Ser Ser Ser Leu Glu Gly Phe His Asn His Phe Lys Val Lys Asn Val
            420                 425                 430

Leu Thr Val Gly Ser Val Ser Ser Glu Glu Leu Asp Glu Asn Tyr Val
            435                 440                 445

Pro Met Asn Pro Asn Ser Pro Pro Arg Gln His Ser Ser Ser Phe Thr
        450                 455                 460

Glu Pro Ile Gln Glu Ala Asn Tyr Val Pro Met Thr Pro Gly Thr Phe
465                 470                 475                 480

Asp Phe Ser Ser Phe Gly Met Gln Val Pro Pro Ala His Met Gly
            485                 490                 495

Phe Arg Ser Ser Pro Lys Thr Pro Pro Arg Arg Pro Val Pro Val Ala
            500                 505                 510

Asp Cys Glu Pro Pro Val Asp Arg Asn Leu Lys Pro Asp Arg Lys
    515                 520                 525

Val Lys Pro Ala Pro Leu Glu Ile Lys Pro Leu Pro Glu Trp Glu Glu
    530                 535                 540

Leu Gln Ala Pro Val Arg Ser Pro Ile Thr Arg Ser Phe Ala Arg Asp
545                 550                 555                 560

Ser Ser Arg Phe Pro Met Ser Pro Arg Pro Asp Ser Val His Ser Thr
            565                 570                 575

Thr Ser Ser Ser Asp Ser His Asp Ser Glu Glu Asn Tyr Val Pro Met
            580                 585                 590

Asn Pro Asn Leu Ser Ser Glu Asp Pro Asn Leu Phe Gly Ser Asn Ser
        595                 600                 605

Leu Asp Gly Gly Ser Ser Pro Met Ile Lys Pro Lys Gly Asp Lys Gln
    610                 615                 620

Val Glu Tyr Leu Asp Leu Asp Leu Asp Ser Gly Lys Ser Thr Pro Pro
625                 630                 635                 640

Arg Lys Gln Lys Ser Ser Gly Ser Gly Ser Ser Val Ala Asp Glu Arg
            645                 650                 655

Val Asp Tyr Val Val Asp Gln Gln Lys Thr Leu Ala Leu Lys Ser
            660                 665                 670

Thr Arg Glu Ala Trp Thr Asp Gly Arg Gln Ser Thr Glu Ser Glu Thr
            675                 680                 685

Pro Ala Lys Ser Val Lys
    690

<210> SEQ ID NO 14
<211> LENGTH: 745
<212> TYPE: PRT
<213> ORGANISM: Homo sapiens

<400> SEQUENCE: 14

Met Glu Val Met Asn Leu Met Glu Gln Pro Ile Lys Val Thr Glu Trp
1               5                   10                  15
```

```
Gln Gln Thr Tyr Thr Tyr Asp Ser Gly Ile His Ser Gly Ala Asn Thr
             20                  25                  30
Cys Val Pro Ser Val Ser Ser Lys Gly Ile Met Glu Glu Asp Glu Ala
             35                  40                  45
Cys Gly Arg Gln Tyr Thr Leu Lys Lys Thr Thr Tyr Thr Gln Gly
             50                  55                  60
Val Pro Pro Ser Gln Gly Asp Leu Glu Tyr Gln Met Ser Thr Thr Ala
 65                  70                  75                  80
Arg Ala Lys Arg Val Arg Glu Ala Met Cys Pro Gly Val Ser Gly Glu
                 85                  90                  95
Asp Ser Ser Leu Leu Leu Ala Thr Gln Val Glu Gly Gln Ala Thr Asn
                100                 105                 110
Leu Gln Arg Leu Ala Glu Pro Ser Gln Leu Leu Lys Ser Ala Ile Val
            115                 120                 125
His Leu Ile Asn Tyr Gln Asp Asp Ala Glu Leu Ala Thr Arg Ala Leu
            130                 135                 140
Pro Glu Leu Thr Lys Leu Leu Asn Asp Glu Asp Pro Val Val Val Thr
145                 150                 155                 160
Lys Ala Ala Met Ile Val Asn Gln Leu Ser Lys Lys Glu Ala Ser Arg
                165                 170                 175
Arg Ala Leu Met Gly Ser Pro Gln Leu Val Ala Val Val Arg Thr
                180                 185                 190
Met Gln Asn Thr Ser Asp Leu Asp Thr Ala Arg Cys Thr Thr Ser Ile
                195                 200                 205
Leu His Asn Leu Ser His His Arg Glu Gly Leu Leu Ala Ile Phe Lys
            210                 215                 220
Ser Gly Gly Ile Pro Ala Leu Val Arg Met Leu Ser Ser Pro Val Glu
225                 230                 235                 240
Ser Val Leu Phe Tyr Ala Ile Thr Thr Leu His Asn Leu Leu Leu Tyr
                245                 250                 255
Gln Glu Gly Ala Lys Met Ala Val Arg Leu Ala Asp Gly Leu Gln Lys
                260                 265                 270
Met Val Pro Leu Leu Asn Lys Asn Asn Pro Lys Phe Leu Ala Ile Thr
            275                 280                 285
Thr Asp Cys Leu Gln Leu Leu Ala Tyr Gly Asn Gln Glu Ser Lys Leu
            290                 295                 300
Ile Ile Leu Ala Asn Gly Gly Pro Gln Ala Leu Val Gln Ile Met Arg
305                 310                 315                 320
Asn Tyr Ser Tyr Glu Lys Leu Leu Trp Thr Thr Ser Arg Val Leu Lys
                325                 330                 335
Val Leu Ser Val Cys Pro Ser Asn Lys Pro Ala Ile Val Glu Ala Gly
            340                 345                 350
Gly Met Gln Ala Leu Gly Lys His Leu Thr Ser Asn Ser Pro Arg Leu
            355                 360                 365
Val Gln Asn Cys Leu Trp Thr Leu Arg Asn Leu Ser Asp Val Ala Thr
    370                 375                 380
Lys Gln Glu Gly Leu Glu Ser Val Leu Lys Ile Leu Val Asn Gln Leu
385                 390                 395                 400
Ser Val Asp Asp Val Asn Val Leu Thr Cys Ala Thr Gly Thr Leu Ser
                405                 410                 415
Asn Leu Thr Cys Asn Asn Ser Lys Asn Lys Thr Leu Val Thr Gln Asn
            420                 425                 430
```

```
Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
    450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
            500                 505                 510

Ala Asn His Ala Pro Leu Gln Glu Ala Ala Val Ile Pro Arg Leu Val
        515                 520                 525

Gln Leu Leu Val Lys Ala His Gln Asp Ala Gln Arg His Val Ala Ala
    530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
            580                 585                 590

Leu Tyr Ser Ser Val Glu Asn Ile Gln Arg Val Ala Ala Gly Val Leu
    595                 600                 605

Cys Glu Leu Ala Gln Asp Lys Glu Ala Ala Asp Ala Ile Asp Ala Glu
610                 615                 620

Gly Ala Ser Ala Pro Leu Met Glu Leu Leu His Ser Arg Asn Glu Gly
625                 630                 635                 640

Thr Ala Thr Tyr Ala Ala Ala Val Leu Phe Arg Ile Ser Glu Asp Lys
                645                 650                 655

Asn Pro Asp Tyr Arg Lys Arg Val Ser Val Glu Leu Thr Asn Ser Leu
            660                 665                 670

Phe Lys His Asp Pro Ala Ala Trp Glu Ala Ala Gln Ser Met Ile Pro
    675                 680                 685

Ile Asn Glu Pro Tyr Gly Asp Asp Leu Asp Ala Thr Tyr Arg Pro Met
690                 695                 700

Tyr Ser Ser Asp Val Pro Leu Asp Pro Leu Glu Met His Met Asp Met
705                 710                 715                 720

Asp Gly Asp Tyr Pro Ile Asp Thr Tyr Ser Asp Gly Leu Arg Pro Pro
                725                 730                 735

Tyr Pro Thr Ala Asp His Met Leu Ala
            740                 745

<210> SEQ ID NO 15
<211> LENGTH: 745
<212> TYPE: PRT
<213> ORGANISM: Homo sapiens

<400> SEQUENCE: 15

Met Glu Val Met Asn Leu Met Glu Gln Pro Ile Lys Val Thr Glu Trp
1               5                   10                  15

Gln Gln Thr Tyr Thr Tyr Asp Ser Gly Ile His Ser Gly Ala Asn Thr
            20                  25                  30

Cys Val Pro Ser Val Ser Lys Gly Ile Met Glu Glu Asp Glu Ala
        35                  40                  45

Cys Gly Arg Gln Tyr Thr Leu Lys Lys Thr Thr Thr Tyr Thr Gln Gly
    50                  55                  60
```

```
Val Pro Pro Ser Gln Gly Asp Leu Glu Tyr Gln Met Ser Thr Thr Ala
 65                  70                  75                  80

Arg Ala Lys Arg Val Arg Glu Ala Met Cys Pro Gly Val Ser Gly Glu
             85                  90                  95

Asp Ser Ser Leu Leu Leu Ala Thr Gln Val Glu Gly Gln Ala Thr Asn
        100                 105                 110

Leu Gln Arg Leu Ala Glu Pro Ser Gln Leu Leu Lys Ser Ala Ile Val
        115                 120                 125

His Leu Ile Asn Tyr Gln Asp Asp Ala Glu Leu Ala Thr Arg Ala Leu
130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Val Val Arg Thr
                180                 185                 190

Met Gln Asn Thr Ser Asp Leu Asp Thr Ala Arg Cys Thr Thr Ser Ile
                195                 200                 205

Leu His Asn Leu Ser His His Arg Glu Gly Leu Leu Ala Ile Phe Lys
210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
                245                 250                 255

Gln Glu Gly Ala Lys Met Ala Val Arg Leu Ala Asp Gly Leu Gln Lys
                260                 265                 270

Met Val Pro Leu Leu Asn Lys Asn Pro Lys Phe Leu Ala Ile Thr
                275                 280                 285

Thr Asp Cys Leu Gln Leu Leu Ala Tyr Gly Asn Gln Glu Ser Lys Leu
290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
                340                 345                 350

Gly Met Gln Ala Leu Gly Lys His Leu Thr Ser Asn Ser Pro Arg Leu
                355                 360                 365

Val Gln Asn Cys Leu Trp Thr Leu Arg Asn Leu Ser Asp Val Ala Thr
370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
                405                 410                 415

Asn Leu Thr Cys Asn Asn Ser Lys Asn Lys Thr Leu Val Thr Gln Asn
                420                 425                 430

Ser Gly Val Glu Ala Leu Ile His Ala Ile Leu Arg Ala Gly Asp Lys
                435                 440                 445

Asp Asp Ile Thr Glu Pro Ala Val Cys Ala Leu Arg His Leu Thr Ser
450                 455                 460

Arg His Pro Glu Ala Glu Met Ala Gln Asn Ser Val Arg Leu Asn Tyr
465                 470                 475                 480
```

```
Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
                500                 505                 510

Ala Asn His Ala Pro Leu Gln Glu Ala Ala Val Ile Pro Arg Leu Val
                515                 520                 525

Gln Leu Leu Val Lys Ala His Gln Asp Ala Gln Arg His Val Ala Ala
            530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
                580                 585                 590

Leu Tyr Ser Ser Val Glu Asn Ile Gln Arg Val Ala Ala Gly Val Leu
            595                 600                 605

Cys Glu Leu Ala Gln Asp Lys Glu Ala Ala Asp Ala Ile Asp Ala Glu
            610                 615                 620

Gly Ala Ser Ala Pro Leu Met Glu Leu Leu His Ser Arg Asn Glu Gly
625                 630                 635                 640

Thr Ala Thr Tyr Ala Ala Ala Val Leu Phe Arg Ile Ser Glu Asp Lys
                645                 650                 655

Asn Pro Asp Tyr Arg Lys Arg Val Ser Val Glu Leu Thr Asn Ser Leu
                660                 665                 670

Phe Lys His Asp Pro Ala Ala Trp Glu Ala Ala Gln Ser Met Ile Pro
            675                 680                 685

Ile Asn Glu Pro Tyr Gly Asp Asp Met Asp Ala Thr Tyr Arg Pro Met
            690                 695                 700

Tyr Ser Ser Asp Val Pro Leu Asp Pro Leu Glu Met His Met Asp Met
705                 710                 715                 720

Asp Gly Asp Tyr Pro Ile Asp Thr Tyr Ser Asp Gly Leu Arg Pro Pro
                725                 730                 735

Tyr Pro Thr Ala Asp His Met Leu Ala
                740                 745

<210> SEQ ID NO 16
<211> LENGTH: 781
<212> TYPE: PRT
<213> ORGANISM: Homo sapiens

<400> SEQUENCE: 16

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Ala Pro Ser Leu Ser Gly
            35                  40                  45

Lys Gly Asn Pro Glu Glu Glu Asp Val Asp Thr Ser Gln Val Leu Tyr
        50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
                100                 105                 110
```

```
Gln Phe Asp Ala Ala His Pro Thr Asn Val Gln Arg Leu Ala Glu Pro
        115                 120                 125
Ser Gln Met Leu Lys His Ala Val Val Asn Leu Ile Asn Tyr Gln Asp
        130                 135                 140
Asp Ala Glu Leu Ala Thr Arg Ala Ile Pro Glu Leu Thr Lys Leu Leu
145                 150                 155                 160
Asn Asp Glu Asp Gln Val Val Asn Lys Ala Ala Val Met Val His
                165                 170                 175
Gln Leu Ser Lys Lys Glu Ala Ser Arg His Ala Ile Met Arg Ser Pro
            180                 185                 190
Gln Met Val Ser Ala Ile Val Arg Thr Met Gln Asn Thr Asn Asp Val
        195                 200                 205
Glu Thr Ala Arg Cys Thr Ala Gly Thr Leu His Asn Leu Ser His His
        210                 215                 220
Arg Glu Gly Leu Leu Ala Ile Phe Lys Ser Gly Ile Pro Ala Leu
225                 230                 235                 240
Val Lys Met Leu Gly Ser Pro Val Asp Ser Val Leu Phe Tyr Ala Ile
                245                 250                 255
Thr Thr Leu His Asn Leu Leu His Gln Glu Gly Ala Lys Met Ala
            260                 265                 270
Val Arg Leu Ala Gly Gly Leu Gln Lys Met Val Ala Leu Leu Asn Lys
        275                 280                 285
Thr Asn Val Lys Phe Leu Ala Ile Thr Thr Asp Cys Leu Gln Ile Leu
        290                 295                 300
Ala Tyr Gly Asn Gln Glu Ser Lys Leu Ile Ile Leu Ala Ser Gly Gly
305                 310                 315                 320
Pro Gln Ala Leu Val Asn Ile Met Arg Thr Tyr Thr Tyr Glu Lys Leu
                325                 330                 335
Leu Trp Thr Thr Ser Arg Val Leu Lys Val Leu Ser Val Cys Ser Ser
            340                 345                 350
Asn Lys Pro Ala Ile Val Glu Ala Gly Gly Met Gln Ala Leu Gly Leu
        355                 360                 365
His Leu Thr Asp Pro Ser Gln Arg Leu Val Gln Asn Cys Leu Trp Thr
        370                 375                 380
Leu Arg Asn Leu Ser Asp Ala Ala Thr Lys Gln Glu Gly Met Glu Gly
385                 390                 395                 400
Leu Leu Gly Thr Leu Val Gln Leu Leu Gly Ser Asp Ile Asn Val
                405                 410                 415
Val Thr Cys Ala Ala Gly Ile Leu Ser Asn Leu Thr Cys Asn Asn Tyr
            420                 425                 430
Lys Asn Lys Met Met Val Cys Gln Val Gly Gly Ile Glu Ala Leu Val
        435                 440                 445
Arg Thr Val Leu Arg Ala Gly Asp Arg Glu Asp Ile Thr Glu Pro Ala
        450                 455                 460
Ile Cys Ala Leu Arg His Leu Thr Ser Arg His Gln Glu Ala Glu Met
465                 470                 475                 480
Ala Gln Asn Ala Val Arg Leu His Tyr Gly Leu Pro Val Val Val Lys
                485                 490                 495
Leu Leu His Pro Pro Ser His Trp Pro Leu Ile Lys Ala Thr Val Gly
            500                 505                 510
Leu Ile Arg Asn Leu Ala Leu Cys Pro Ala Asn His Ala Pro Leu Arg
        515                 520                 525
```

```
Glu Gln Gly Ala Ile Pro Arg Leu Val Gln Leu Leu Val Arg Ala His
    530                 535                 540
Gln Asp Thr Gln Arg Arg Thr Ser Met Gly Gly Thr Gln Gln Gln Phe
545                 550                 555                 560
Val Glu Gly Val Arg Met Glu Glu Ile Val Glu Gly Cys Thr Gly Ala
                565                 570                 575
Leu His Ile Leu Ala Arg Asp Val His Asn Arg Ile Val Ile Arg Gly
                580                 585                 590
Leu Asn Thr Ile Pro Leu Phe Val Gln Leu Leu Tyr Ser Pro Ile Glu
            595                 600                 605
Asn Ile Gln Arg Val Ala Ala Gly Val Leu Cys Glu Leu Ala Gln Asp
        610                 615                 620
Lys Glu Ala Ala Glu Ala Ile Glu Ala Glu Gly Ala Thr Ala Pro Leu
625                 630                 635                 640
Thr Glu Leu Leu His Ser Arg Asn Glu Gly Val Ala Thr Tyr Ala Ala
                645                 650                 655
Ala Val Leu Phe Arg Met Ser Glu Asp Lys Pro Gln Asp Tyr Lys Lys
                660                 665                 670
Arg Leu Ser Val Glu Leu Thr Ser Ser Leu Phe Arg Thr Glu Pro Met
            675                 680                 685
Ala Trp Asn Glu Thr Ala Asp Leu Gly Leu Asp Ile Gly Ala Gln Gly
        690                 695                 700
Glu Pro Leu Gly Tyr Arg Gln Asp Pro Ser Tyr Arg Ser Phe His
705                 710                 715                 720
Ser Gly Gly Tyr Gly Gln Asp Ala Leu Gly Met Asp Pro Met Met Glu
                725                 730                 735
His Glu Met Gly Gly His His Pro Gly Ala Asp Tyr Pro Val Asp Gly
                740                 745                 750
Leu Pro Asp Leu Gly His Ala Gln Asp Leu Met Asp Gly Leu Pro Pro
            755                 760                 765
Gly Asp Ser Asn Gln Leu Ala Trp Phe Asp Thr Asp Leu
770                 775                 780

<210> SEQ ID NO 17
<211> LENGTH: 7
<212> TYPE: PRT
<213> ORGANISM: Unknown
<220> FEATURE:
<223> OTHER INFORMATION: Conserved catalytic domain that is a unique
      signature sequence motif that is invariant among
      all PTPs.
<220> FEATURE:
<221> NAME/KEY: VARIANT
<222> LOCATION: 2,3,4,5,6
<223> OTHER INFORMATION: Xaa = any amino acid

<400> SEQUENCE: 17

Cys Xaa Xaa Xaa Xaa Xaa Arg
 1               5

<210> SEQ ID NO 18
<211> LENGTH: 11
<212> TYPE: PRT
<213> ORGANISM: unknown
<220> FEATURE:
<223> OTHER INFORMATION: Eleven amino acid conserved sequence found in a
      majority of PTPs.
<220> FEATURE:
<221> NAME/KEY: VARIANT
<222> LOCATION: 1
<223> OTHER INFORMATION: Xaa = Ile or Val
```

```
<220> FEATURE:
<221> NAME/KEY: VARIANT
<222> LOCATION: 10
<223> OTHER INFORMATION: Xaa = Ser or Thr

<400> SEQUENCE: 18

Xaa His Cys Xaa Ala Gly Xaa Xaa Arg Xaa Gly
1               5                   10

<210> SEQ ID NO 19
<211> LENGTH: 17
<212> TYPE: PRT
<213> ORGANISM: Artificial Sequence
<220> FEATURE:
<223> OTHER INFORMATION: DEP-1 extracellular domain peptide.

<400> SEQUENCE: 19

Cys Asp Ala Ser Asn Thr Glu Arg Ser Arg Ala Gly Ser Pro Thr Ala
1               5                   10                  15
Pro

<210> SEQ ID NO 20
<211> LENGTH: 8
<212> TYPE: PRT
<213> ORGANISM: unknown
<220> FEATURE:
<223> OTHER INFORMATION: Sequence which matched the src substrate and
      adherens junction component, p120ctn

<400> SEQUENCE: 20

Asn Leu Ser Tyr Gln Val His Arg
1               5

<210> SEQ ID NO 21
<211> LENGTH: 17
<212> TYPE: PRT
<213> ORGANISM: unknown
<220> FEATURE:
<223> OTHER INFORMATION: Sequences which matched the src substrate and
      adherens junction component, p120ctn

<400> SEQUENCE: 21

Ser Gln Ser Ser His Ser Tyr Asp Asp Ser Thr Leu Pro Leu Ile Asp
1               5                   10                  15
Arg

<210> SEQ ID NO 22
<211> LENGTH: 745
<212> TYPE: PRT
<213> ORGANISM: Homo sapiens

<400> SEQUENCE: 22

Met Glu Val Met Asn Leu Met Glu Gln Pro Ile Lys Val Thr Glu Trp
1               5                   10                  15

Gln Gln Thr Tyr Thr Tyr Asp Ser Gly Ile His Ser Gly Ala Asn Thr
            20                  25                  30

Cys Val Pro Ser Val Ser Lys Gly Ile Met Glu Asp Glu Ala
        35                  40                  45

Cys Gly Arg Gln Tyr Thr Leu Lys Lys Thr Thr Thr Tyr Thr Gln Gly
    50                  55                  60

Val Pro Pro Ser Gln Gly Asp Leu Glu Tyr Gln Met Ser Thr Thr Ala
65                  70                  75                  80

Arg Ala Lys Arg Val Arg Glu Ala Met Cys Pro Gly Val Ser Gly Glu
```

```
                      85                  90                  95
Asp Ser Ser Leu Leu Ala Thr Gln Val Glu Gly Gln Ala Thr Asn
            100                 105                 110
Leu Gln Arg Leu Ala Glu Pro Ser Gln Leu Leu Lys Ser Ala Ile Val
            115                 120                 125
His Leu Ile Asn Tyr Gln Asp Ala Glu Leu Ala Thr Arg Ala Leu
    130                 135                 140
Pro Glu Leu Thr Lys Leu Leu Asn Asp Glu Asp Pro Val Val Val Thr
145                 150                 155                 160
Lys Ala Ala Met Ile Val Asn Gln Leu Ser Lys Glu Ala Ser Arg
                165                 170                 175
Arg Ala Leu Met Gly Ser Pro Gln Leu Val Ala Val Val Arg Thr
            180                 185                 190
Met Gln Asn Thr Ser Asp Leu Asp Thr Ala Arg Cys Thr Thr Ser Ile
    195                 200                 205
Leu His Asn Leu Ser His His Arg Glu Gly Leu Leu Ala Ile Phe Lys
    210                 215                 220
Ser Gly Gly Ile Pro Ala Leu Val Arg Met Leu Ser Ser Pro Val Glu
225                 230                 235                 240
Ser Val Leu Phe Tyr Ala Ile Thr Thr Leu His Asn Leu Leu Leu Tyr
                245                 250                 255
Gln Glu Gly Ala Lys Met Ala Val Arg Leu Ala Asp Gly Leu Gln Lys
            260                 265                 270
Met Val Pro Leu Leu Asn Lys Asn Pro Lys Phe Leu Ala Ile Thr
    275                 280                 285
Thr Asp Cys Leu Gln Leu Leu Ala Tyr Gly Asn Gln Glu Ser Lys Leu
    290                 295                 300
Ile Ile Leu Ala Asn Gly Gly Pro Gln Ala Leu Val Gln Ile Met Arg
305                 310                 315                 320
Asn Tyr Ser Tyr Glu Lys Leu Leu Trp Thr Thr Ser Arg Val Leu Lys
                325                 330                 335
Val Leu Ser Val Cys Pro Ser Asn Lys Pro Ala Ile Val Glu Ala Gly
            340                 345                 350
Gly Met Gln Ala Leu Gly Lys His Leu Thr Ser Asn Ser Pro Arg Leu
            355                 360                 365
Val Gln Asn Cys Leu Trp Thr Leu Arg Asn Leu Ser Asp Val Ala Thr
    370                 375                 380
Lys Gln Glu Gly Leu Glu Ser Val Leu Lys Ile Leu Val Asn Gln Leu
385                 390                 395                 400
Ser Val Asp Asp Val Asn Val Leu Thr Cys Ala Thr Gly Thr Leu Ser
            405                 410                 415
Asn Leu Thr Cys Asn Asn Ser Lys Asn Lys Thr Leu Val Thr Gln Asn
            420                 425                 430
Ser Gly Val Glu Ala Leu Ile His Ala Ile Leu Arg Ala Gly Asp Lys
    435                 440                 445
Asp Asp Ile Thr Glu Pro Ala Val Cys Ala Leu Arg His Leu Thr Ser
450                 455                 460
Arg His Pro Glu Ala Glu Met Ala Gln Asn Ser Val Arg Leu Asn Tyr
465                 470                 475                 480
Gly Ile Pro Ala Ile Val Lys Leu Leu Asn Gln Pro Asn Gln Trp Pro
            485                 490                 495
Leu Val Lys Ala Thr Ile Gly Leu Ile Arg Asn Leu Ala Leu Cys Pro
            500                 505                 510
```

-continued

```
Ala Asn His Ala Pro Leu Gln Glu Ala Ala Val Ile Pro Arg Leu Val
        515                 520                 525

Gln Leu Leu Val Lys Ala His Gln Asp Ala Gln Arg His Val Ala Ala
        530                 535                 540

Gly Thr Gln Gln Pro Tyr Thr Asp Gly Val Arg Met Glu Glu Ile Val
545                     550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
            580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
        610                 615                 620

Gly Ala Ser Ala Pro Leu Met Glu Leu Leu His Ser Arg Asn Glu Gly
625                 630                 635                 640

Thr Ala Thr Tyr Ala Ala Ala Val Leu Phe Arg Ile Ser Glu Asp Lys
                645                 650                 655

Asn Pro Asp Tyr Arg Lys Arg Val Ser Val Glu Leu Thr Asn Ser Leu
                660                 665                 670

Phe Lys His Asp Pro Ala Ala Trp Glu Ala Ala Gln Ser Met Ile Pro
            675                 680                 685

Ile Asn Glu Pro Tyr Gly Asp Asp Met Asp Ala Thr Tyr Arg Pro Met
        690                 695                 700

Tyr Ser Ser Asp Val Pro Leu Asp Pro Leu Glu Met His Met Asp Met
705                 710                 715                 720

Asp Gly Asp Tyr Pro Ile Asp Thr Tyr Ser Asp Gly Leu Arg Pro Pro
                725                 730                 735

Tyr Pro Thr Ala Asp His Met Leu Ala
            740             745
```

DEP-1 RECEPTOR PROTEIN TYROSINE PHOSPHATASE INTERACTING PROTEINS AND RELATED METHODS

CROSS-REFERENCE TO RELATED APPLICATION

This application claims the benefit of U.S. Provisional Patent Application No. 60/429,746 filed Nov. 26, 2002, which is incorporated herein by reference in its entirety.

STATEMENT REGARDING FEDERALLY SPONSORED RESEARCH OR DEVELOPMENT

This invention was made with government support under Grant Nos. RO1-GM55989 and T32-CA09311 awarded by the National Institutes of Health. The government may have certain rights in this invention.

BACKGROUND OF THE INVENTION

1. Field of the Invention

The present invention relates generally to biomolecules that mediate biological signal transduction in cells, which signals are communicated by phosphorylation and dephosphorylation of cellular proteins for processes such as cellular differentiation, activation, proliferation and survival. More specifically, the invention relates to specific interactions between the protein tyrosine phosphatase known as density enhanced phosphatase-1 (DEP-1) and several distinct cellular proteins, and to related compositions and methods.

2. Description of the Related Art

Protein tyrosine phosphorylation is an essential element in signal transduction pathways that control fundamental cellular processes including growth and differentiation, cell cycle progression, and cytoskeletal function. Briefly, the binding of hormones, cytokines, growth factors, or other ligands to a cognate receptor protein tyrosine kinase (PTK) triggers autophosphorylation of tyrosine residues in the receptor itself and phosphorylation of tyrosine residues in the enzyme's target substrates. Within the cell, tyrosine phosphorylation is a reversible process; the phosphorylation state of a particular tyrosine residue in a target substrate is governed by the coordinated action of both PTKs that catalyze phosphorylation and protein tyrosine phosphatases (PTPs) that catalyze dephosphorylation.

The PTPs are a large and diverse family of enzymes found ubiquitously in eukaryotes (Charbonneau and Tonks, *Ann. Rev. Cell Biol.* 8:463–93 (1993)). Structural diversity within the PTP family arises primarily from variation in non-catalytic (potentially regulatory) sequences that are linked to one or more highly conserved catalytic domains. In general, soluble cytoplasmic PTP forms are termed non-receptor PTPs and those with at least one non-catalytic region that traverses the cell membrane are termed receptor-like PTPs (RPTPs).

A variety of non-receptor PTPs have been identified that characteristically possess a single catalytic domain flanked by non-catalytic sequences. Such non-catalytic sequences have been shown to include, among others, sequences homologous to cytoskeletal-associated proteins (Yang et al., *Proc. Natl. Acad. Sci. USA* 88:5949–53 (1991)) or to lipid binding proteins (Gu et al., *Proc. Natl. Acad. Sci. USA* 89:2980–84 (1992)), and/or sequences that mediate association of the enzyme with specific intracellular membranes (Frangioni et al., *Cell* 68:545–60 (1992)), suggesting that subcellular localization may play a significant role in regulation of PTP activity.

Among RPTPs, analysis of non-catalytic domain sequences suggests their involvement in signal transduction mechanisms; however, binding of specific ligands to the extracellular segment of RPTPs has been characterized in only a few instances. For example, homophilic binding has been demonstrated between molecules of PTPµ (Brady-Kalnay et al., *J. Cell. Biol.* 122:961–972 (1993)) i.e., the ligand for PTPµ expressed on a cell surface is another PTPµ molecule on the surface of an adjacent cell. Little is otherwise known about ligands that specifically bind to, and modulate the activity of, the majority of RPTPs.

Many receptor-like PTPs comprise an intracellular carboxyl segment with two catalytic domains, a single transmembrane domain and an extracellular amino terminal segment (Krueger et al., *EMBO J.* 9:3241–52 (1990)). Subclasses of RPTPs are distinguished from one another on the basis of categories or "types" of extracellular domains (Fischer et al., *Science* 253:401–406 (1991)). Type I RPTPs have a large extracellular domain with multiple glycosylation sites and a conserved cysteine-rich region. CD45 is a typical Type I RPTP. The Type II RPTPs contain at least one amino terminal immunoglobulin (Ig)-like domain adjacent to multiple tandem fibronectin type III (FNIII)-like repeats. Similar repeated FNIII domains, believed to participate in protein-protein interactions, have been identified in receptors for IL2, IL4, IL6, GM-CSF, prolactin, erythropoietin, and growth hormone (Patthy, *Cell* 61:13–14 (1992)). The leukocyte common antigen-related PTP known as LAR exemplifies the Type II RPTP structure (Streuli et al., *J. Exp. Med.* 168:1523–30 (1988)), and, like other Type II RPTPs, contains an extracellular region reminiscent of the NCAM class of cellular adhesion molecules (Edelman and Crossin, *Ann. Rev. Biochem.* 60:155–190 (1991)). The Type III RPTPs, such as HPTPβ (Krueger et al., *EMBO J.* 9:3241–52 (1990)), contain only multiple tandem FNIII repeats in the extracellular domain. The Type IV RPTPs, for example RPTPα (Krueger et al. (1990) supra), have relatively short extracellular sequences lacking cysteine residues but containing multiple glycosylation sites. A fifth type of RPTP, exemplified by PTPγ (Barnes et al., *Mol. Cell Biol.* 13:1497–506 (1993)) and PTPζ (Krueger and Saito, *Proc. Natl. Acad. Sci. USA* 89:7417–21 (1992)), is characterized by an extracellular domain containing a 280 amino acid segment that is homologous to carbonic anhydrase (CAH) but lacks essential histidine residues required for reversible hydration of carbon dioxide.

Characteristics shared by both the soluble PTPs and the RPTPs include an absolute specificity for phosphotyrosine residues, a high affinity for substrate proteins, and a specific activity that is one to three orders of magnitude in excess of that of the PTKs in vitro (Fischer et al., *Science* 253: 401–406 (1991); Tonks, *Curr. Opin. Cell. Biol.* 2:1114–24 (1990)). Supporting a significant physiological role for PTP activity is the observation that treatment of NRK-1 cells with vanadate, a potent inhibitor of PTP activity, resulted in enhanced levels of phosphotyrosine and generation of a transformed cellular morphology (Klarlund, *Cell* 41:707–17 (1985)). This observation implies potential therapeutic value for PTPs and agents that modulate PTP activity as indirect modifiers of PTK activity and, thus, levels of cellular phosphotyrosine.

Other studies have also highlighted aspects of the physiological importance of PTP activity. For example, mutations in the gene encoding a non-receptor hematopoietic cell protein tyrosine phosphatase, HCP, have been shown to result in severe immune dysfunction characteristic of the motheaten phenotype in mice (Schultz et al., *Cell*

73:1445–54 (1993)). Under normal conditions HCP may act as a suppressor of PTK-induced signaling pathways, for example, the CSF-1 receptor (Schultz et al., supra). Some PTP enzymes may be the products of tumor suppressor genes, and their mutation or deletion may contribute to the elevation in cellular phosphotyrosine associated with certain neoplasias (Brown-Shimer et al., Cancer Res. 52:478–82 (1992); Wary et al., Cancer Res. 53:1498–502 (1993)). Mutations observed in the gene for RPTPγ in murine L cells would be consistent with this hypothesis (Wary et al., Cancer Res. 53:1498–502 (1993)). The observation that the receptor-like PTP CD45 is required for normal T cell receptor-induced signaling (Pingel et al., Cell 58:1055–65 (1989)) provides evidence implicating PTP activity as a positive mediator of cellular signaling responses. Mice homozygous for a disrupted PTP-1B gene (PTP-1B −/−) exhibited enhanced sensitivity to insulin and resistance to weight gain, relative to controls having functional PTP-1B (Elchebly et al., 1999 Science 283:1544).

A variety of ligands trigger the reversible phosphorylation of tyrosyl residues in cellular proteins, a process that underlies the control of such fundamental cellular functions as growth and proliferation, migration and morphogenesis. Tyrosine phosphorylation is regulated by the coordinated action of protein tyrosine kinases (PTKs) and protein tyrosine phosphatases (PTPs). Classically it was thought that the PTKs provided the "on-switch" to initiate a physiological response, whereas the PTPs functioned to counteract the PTKs and to return the system to its basal state. However, it has been shown that PTPs may themselves function positively to promote signaling, for example by promoting the dephosphorylation and activation of PTKs, thus coordinating with, rather than antagonizing PTK function (reviewed in (Hermiston et al., J. Clin. Invest. 109:9–14 (2002)). A further level of complexity has been introduced with the realization that whether a defined PTP functions positively or negatively may depend upon the signaling context. Thus, SHP-2 is an activator of signaling through the HGF/SF receptor Met (Maroun et al., Mol. Cell Biol. 20:8513–25 (2000)) and the EGF receptor (Bennett et al., Mol. Cell Biol. 16:1189–202 (1996)), but is an inhibitor of signaling through the PDGF receptor (Meng et al., Mol. Cell 9:387–99 (2002)). Following ligand binding, a receptor PTK may become phosphorylated on multiple tyrosine residues, which serve as docking sites for distinct signaling proteins. The spectrum of such signaling molecules that associate with the PTK will determine the nature of the response that is initiated following ligand stimulation. The possibility exists, therefore, that a PTP may dephosphorylate a particular site in a receptor PTK and thereby determine the signaling outcome of a particular stimulus. Thus, dephosphorylation of receptor PTKs by members of the PTP family may function as a mechanism for regulating the specificity of a signaling event rather than simply as an "off-switch."

Normal cells in culture exhibit contact inhibition of growth, that is, as adjacent cells in a confluent monolayer touch each other, their growth is inhibited (Stoker et al., Nature 215:171–72 (1967)). Because PTKs promote cell growth, PTP action may underlie mechanisms of growth inhibition. Density Enhanced PTP-1 (DEP-1) is a Type III receptor PTP whose expression is enhanced as cells approach confluence (Ostman et al., Proc. Natl. Acad. Sci. USA 91:9680–84 (1994)). Initially cloned from human cDNA libraries (U.S. Pat. No. 6,114,140; WO95/30008), DEP-1 homologues were subsequently identified in rat and mouse (Kuramochi et al., FEBS Lett. 378:7–14 (1996); Borges et al., Circ. Res. 79:570–80 (1996)).

DEP-1 comprises an extracellular segment of eight-fibronectin type III repeats, a transmembrane domain and a single cytoplasmic PTP domain. Also known as PTP-η (Honda et al., Blood 84:4186–94 (1994)) and CD 148 (Palou et al., Immunol. Lett. 57:101–103 (1997)), DEP-1 is expressed in a variety of tissues and cell types. There is a growing body of evidence suggesting a role for DEP-1 in the inhibition of cell growth. After vascular injury DEP-1 expression is down regulated in migrating and proliferating rat endothelial cells (Borges et al., supra). Attempts have been made to express DEP-1 constitutively in breast cells and macrophages (Keane et al., Cancer Res. 56:4236–43 (1996); Osborne et al., J. Leukoc. Biol. 64:692–701 (1998)), however, this inhibited development of stable cell lines, further reinforcing a role for DEP-1 in growth inhibition.

In addition to its role in growth inhibition, DEP-1 has also been implicated in differentiation. The levels of DEP-1 mRNA are increased in various cell lines in response to factors that lead to differentiation (Borges et al., supra; Keane et al., supra; Zhang et al., Exp. Cell Res. 235:62–70 (1997); Martelli et al., Exp. Cell Res. 245:195–202 (1998)). Interestingly, in rat thyroid cells the expression of DEP-1 (rPTP-TI) mRNA decreases with increasing levels of transformation (Zhang et al., supra; Florio et al., Endocrinology 138:3756–63 (1997)). Re-introduction of DEP-1 into the transformed cells leads to reduced growth rates, stabilization of the cyclin-dependent kinase inhibitor $p27^{kip1}$ and partial re-acquisition of a differentiated phenotype (Trapasso et al., Mol. Cell Biol. 20:9236–46 (2000)). Loss of DEP-1 expression has also been observed in human thyroid tumors (id.). Furthermore, the DEP-1 gene Ptprj was identified as a positional candidate for the mouse colon-cancer susceptibility locus Scc1(Ruivenkamp et al., Nat. Genet. 31:295–300 (2002)). Frequent deletions, loss of heterozygosity (LOH) and missense mutations in the human Ptprj gene have also been identified in colon, lung and breast cancers (id.). Taken together these data indicate that DEP-1 may be a critical factor in controlling cellular growth and transformation.

DEP-1 has recently been shown to localize at cell borders in endothelial cells and its staining pattern overlapped with that of the functional protein VE-cadherin (Takahashi et al., J. Am. Soc. Nephrol. 10:2135–45 (1999)). Interestingly, members of the cadherin family of cell-cell adhesion molecules function in the suppression of cell growth and tumor invasion. Junctional components such as β-catenin, however, can also promote cell growth by inducing the transcription of genes involved in proliferation and cancer progression (reviewed in Ben-Ze'ev et al., Exp. Cell Res. 261:75–83 (2000)). The growth inhibitory effects of cadherins may involve binding and sequestration of the signaling pool of the catenins (Gottardi et al., J. Cell Biol. 153:1049–60 (2001); Stockinger et al., J. Cell Biol. 154: 1185–96 (2001)). Reversible tyrosine phosphorylation is an important aspect of the regulation of functional integrity and the control of signals emanating from these sites (reviewed in Conacci-Sorrell et al., J. Clin. Invest. 109:987–91 (2002)).

Clearly there is a need for the identification of PTPs, PTKs and other components of biological signal transduction pathways that interact with members of these enzyme families, in order to better understand the cellular and molecular mechanisms that govern such processes as cell growth, differentiation and survival in normal and pathological conditions. For instance, determination of the PTKs and PTPs that act upon the components of cell junctions will be important for understanding the regulation of cell morphology and the control of gene expression, events that ultimately influence growth and migration. The present invention contributes to such understanding of the biological signal transduction pathways in which DEP-1 functions by identifying several proteins with which DEP-1 specifically interacts, and offers other related advantages.

BRIEF SUMMARY OF THE INVENTION

It is an aspect of the present invention to provide an isolated complex comprising (a) a DEP-1 polypeptide that is capable of specific association with a DEP-1 substrate polypeptide; and (b) a DEP-1 substrate polypeptide that is in specific association with the DEP-1 polypeptide. In a certain embodiment the DEP-1 polypeptide is selected from (a) a polypeptide which comprises the amino acid sequence set forth in SEQ ID NO:2 (Genbank No. U10886); (b) a polypeptide which comprises the amino acid sequence set forth in SEQ ID NO:3 (positions 997–1337 of SEQ ID NO:2); (c) a polypeptide that is encoded by a polynucleotide that hybridizes under moderately stringent conditions to a nucleic acid molecule which comprises a nucleotide sequence that is a reverse complement of SEQ ID NO:1 (Genbank No. U10886); (d) a truncated DEP-1 polypeptide which comprises at least the amino acid sequence set forth at positions 1205–1245 of SEQ ID NO:2, or a variant thereof; (e) a mutant polypeptide which comprises at least one amino acid substitution in the amino acid sequence set forth in SEQ ID NO:2, wherein the amino acid substitution is selected from a substitution of aspartate at position 1205 and a substitution of cysteine at position 1239; (f) a mutant polypeptide according to (e) wherein aspartate at position 1205 is substituted with alanine; (g) a mutant polypeptide according to (e) wherein cysteine at position 1239 is substituted with serine; (h) a mutant polypeptide which comprises an amino acid sequence as set forth at positions 997–1337 of SEQ ID NO:2, the mutant polypeptide comprising at least one amino acid substitution that is selected from a substitution of aspartate at position 1205 and a substitution of cysteine at position 1239; (i) a mutant polypeptide according to (h) wherein aspartate at position 1205 is substituted with alanine; (j) a mutant polypeptide according to (h) wherein cysteine at position 1239 is substitute with serine; (k) a polypeptide that is encoded by a polynucleotide that hybridizes under moderately stringent conditions to a nucleic acid molecule which comprises a reverse complement of a nucleotide sequence that encodes a polypeptide selected from any one of (e)–(j); (l) a polypeptide to which binds an antibody that specifically recognizes a polypeptide that comprises the amino acid sequence set forth in SEQ ID NO:2; and (m) a polypeptide to which binds an antibody that specifically recognizes a polypeptide that comprises the amino acid sequence set forth in SEQ ID NO:3.

In another embodiment the invention provides an isolated complex comprising (a) a DEP-1 polypeptide that is capable of specific dephosphorylation of a DEP-1 substrate polypeptide; and (b) a DEP-1 substrate polypeptide that is in specific association with the DEP-1 polypeptide. According to certain further embodiments, in either of the above described isolated complexes the DEP-1 substrate polypeptide is selected from (a) a polypeptide which comprises the amino acid sequence set forth in any one of SEQ ID NOS:4–6 (SEQ ID NO:4, GenBank Acc. No. P08581; SEQ ID NO:5, Acc. No. AAA59591; SEQ ID NO:6, NM_000245); (b) a polypeptide which comprises a transmembrane domain and a cytoplasmic domain of the polypeptide of (a) as described in Zhu et al. (1994 *Cell Growth Differ.* 5(4):359–366), and which comprises the amino acid sequence set forth in SEQ ID NO:7; (c) at least one p120$^{ctn}$ polypeptide comprising an amino acid sequence as set forth in any one of SEQ ID NOS:8–12 (GenBank Acc. Nos. AF062321, AF062317, AF062319, AF062338, AF062342, respectively); and (d) a Gab1 polypeptide comprising an amino acid sequence as set forth in SEQ ID NO: 13 (GenBank Acc. No. NM_002039).

In certain other embodiments the invention provides an isolated complex comprising a DEP-1 polypeptide in specific association with a polypeptide selected from (i) a plakoglobin polypeptide comprising an amino acid sequence as set forth in any one of SEQ ID NOS:14–15, and 22 (Acc. No. BC011865, Acc. No. Z68228, Acc. No. NM_021991, respectively), and (ii) a beta-catenin polypeptide comprising an amino acid sequence as set forth in SEQ ID NO:16 (Acc. No. NM_001904), wherein the DEP-1 polypeptide is selected from the group consisting of members (a)–(m) as described above.

Turning to another aspect of the present invention, a method is provided of identifying an agent that alters interaction of a DEP-1 polypeptide with a DEP-1 substrate polypeptide, comprising (a) exposing, in the absence and presence of a candidate agent, a sample comprising a DEP-1 polypeptide and a DEP-1 substrate polypeptide to conditions sufficient for formation of a complex comprising the DEP-1 polypeptide in specific association with the DEP-1 substrate polypeptide; and (b) comparing a first level of the complex that is formed in the absence of the candidate agent to a second level of the complex that is formed in the presence of the candidate agent, wherein an alteration in the second level relative to the first level indicates that the agent alters interaction between the DEP-1 polypeptide and the DEP-1 substrate polypeptide.

In another embodiment the invention provides a method of identifying an agent that alters dephosphorylation by a DEP-1 polypeptide of a DEP-1 substrate polypeptide, comprising (a) exposing, in the absence and presence of a candidate agent, a sample comprising a DEP-1 polypeptide and a DEP-1 substrate polypeptide to conditions sufficient for (i) formation of a complex comprising the DEP-1 polypeptide in specific association with the DEP-1 substrate polypeptide and (ii) determination of dephosphorylation of the DEP-1 substrate polypeptide; and (b) comparing a first level of DEP-1 substrate polypeptide dephosphorylation in the absence of the candidate agent to a second level of DEP-1 substrate polypeptide dephosphorylation in the presence of the candidate agent, wherein an alteration in the second level relative to the first level indicates that the agent alters dephosphorylation by the DEP-1 polypeptide of the DEP-1 substrate polypeptide. In certain further embodiments of either of the methods just described, the DEP-1 polypeptide is selected from the group consisting of members (a)–(m) as described above. In certain other further embodiments of either of the methods just described, the DEP-1 substrate polypeptide is selected from (a) a polypeptide which comprises the amino acid sequence set forth in any one of SEQ ID NOS:4–6 (SEQ ID NO:4, GenBank Acc. No. P08581; (SEQ ID NO:5, Acc. No. AAA59591; (SEQ ID NO:6, NM_000245); (b) a polypeptide which comprises a transmembrane domain and a cytoplasmic domain of the polypeptide of (a) as described in Zhu et al. (1994 *Cell Growth Differ.* 5(4):359–366), such polypeptide comprising the amino acid sequence set forth in SEQ ID NO:7, (c) at least one p120$^{ctn}$ polypeptide comprising an amino acid sequence as set forth in any one of SEQ ID NOS:8–12 (GenBank Acc. Nos. AF062321, AF062317, AF062319, AF062338, AF062342, respectively); and (d) a Gab1 polypeptide comprising an amino acid sequence as set forth in SEQ ID NO: 13 (GenBank Acc. No. NM_002039).

Turning to another aspect, the present invention provides a recombinant expression construct comprising a regulated promoter operably linked to a polynucleotide encoding a DEP-1 polypeptide. In one embodiment the regulated promoter is an inducible promoter, and in another embodiment the regulated promoter is a tightly regulated promoter. In certain embodiments the DEP-1 polypeptide is selected from the group consisting of members (a)–(m) as described above. In a related embodiment the invention provides a host cell comprising the above-described recombinant expression construct, and in another embodiment the invention provides a cell line derived from such a host cell. In certain further embodiments the cell line is an immortal cell line, which in certain still further embodiments may be a cell line derived from a host cell that is a cancer cell, a transformed cell or a malignant cell.

It is another aspect of the invention to provide a method of altering transduction of a biological signal in a cell, comprising introducing into a cell a DEP-1 polypeptide that is capable of specific association with a DEP-1 substrate polypeptide under conditions and for a time sufficient to permit formation of a complex comprising the DEP-1 polypeptide in specific association with the DEP-1 substrate polypeptide, wherein (i) the DEP-1 polypeptide is selected from the group consisting of members (a)–(m) as described above, and wherein (ii) the cell comprises a DEP-1 substrate polypeptide that is selected from (a) a polypeptide which comprises the amino acid sequence set forth in any one of SEQ ID NOS:4–6 (SEQ ID NO:4, GenBank Acc. No. P08581; SEQ ID NO:5, Acc. No. AAA59591; SEQ ID NO:6, NM_000245); (b) a polypeptide which comprises a transmembrane domain and a cytoplasmic domain of the polypeptide of (a) as described in Zhu et al. (1994 Cell Growth Differ. 5(4):359–366), and which comprises the amino acid sequence set forth in SEQ ID NO:7; (c) at least one p120$^{ctn}$ polypeptide comprising an amino acid sequence as set forth in any one of SEQ ID NOS:8–12 (GenBank Acc. Nos. AF062321, AF062317, AF062319, AF062338, AF062342, respectively); and (d) a Gab1 polypeptide comprising an amino acid sequence as set forth in SEQ ID NO: 13 (GenBank Acc. No. NM_002039). In a further embodiment the step of introducing comprises inducing expression of a polynucleotide that encodes the DEP-1 polypeptide, wherein the polynucleotide is present within the cell. In another embodiment the step of introducing comprises transforming or transfecting the cell with a recombinant expression construct that comprises a polynucleotide that encodes the DEP-1 polypeptide.

In another embodiment the invention provides a method of altering transduction of a biological signal in a cell, comprising contacting a cell with an agent, (i) wherein the cell comprises a DEP-1 polypeptide and a DEP-1 substrate polypeptide, the DEP-1 polypeptide being capable of specific association with the DEP-1 substrate polypeptide to form a complex, (ii) wherein the agent is capable of altering the specific association of the DEP-1 polypeptide with the DEP-1 substrate polypeptide, (iii) wherein the DEP-1 polypeptide is selected from the group consisting of members (a)–(m) as described above, and (iv) wherein the DEP-1 substrate polypeptide is selected from (a) a polypeptide which comprises the amino acid sequence set forth in any one of SEQ ID NOS:4–6 (SEQ ID NO:4, GenBank Acc. No. P08581; SEQ ID NO:5, Acc. No. AAA59591; SEQ ID NO:6, NM_000245); (b) a polypeptide which comprises a transmembrane domain and a cytoplasmic domain of the polypeptide of (a) as described in Zhu et al. (1994 Cell Growth Differ. 5(4):359–366), and which comprises the amino acid sequence set forth in SEQ ID NO:7; (c) at least one p120$^{ctn}$ polypeptide comprising an amino acid sequence as set forth in any one of SEQ ID NOS:8–12 (GenBank Acc. Nos. AF062321, AF062317, AF062319, AF062338, AF062342, respectively); and (d) a Gab1 polypeptide comprising an amino acid sequence as set forth in SEQ ID NO: 13 (GenBank Acc. No. NM_002039).

According to certain further embodiments of either of the above-described methods for altering transduction of a biological signal, formation of the complex results in dephosphorylation of the DEP-1 substrate polypeptide. In a still further embodiment the DEP-1 substrate polypeptide is selected from (i) a polypeptide which comprises the amino acid sequence set forth in any one of SEQ ID NOS:4–6 (SEQ ID NO:4, GenBank Acc. No. P08581; SEQ ID NO:5, Acc. No. AAA59591; SEQ ID NO:6, NM_000245); and (ii) a polypeptide which comprises a transmembrane domain and a cytoplasmic domain of the polypeptide of (i) as described in Zhu et al. (1994 Cell Growth Differ. 5(4):359–366), and which comprises the amino acid sequence set forth in SEQ ID NO:7, and at least one phosphorylated amino acid selected from the amino acid corresponding to position 1349 of SEQ ID NO:4 and the amino acid corresponding to position 1365 of SEQ ID NO:4 is dephosphorylated. In certain other further embodiments of either of the above-described methods for altering transduction of a biological signal, transduction of the biological signal results in altered cell proliferation, differentiation or survival. In certain other further embodiments of either of the above-described methods for altering transduction of a biological signal, transduction of the biological signal results in altered cellular morphogenesis or altered cellular motility.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 1A: Immunoblot of tyrosine phosphorylated proteins trapped by DEP-1(DA). T-47D cells were treated with 50 µM pervanadate for 20 minutes prior to lysis. Maltose binding protein (MBP) or MBP.DEP-1 fusion proteins (MBP fused to wildtype DEP-1: MBP.DEP-1; MBP fused to catalytically inactive DEP-1: MBP.DEP-1(CS); and MBP fused to DEP-1 substrate trapping mutant MBP.DEP-1(DA)) were incubated with cell lysates and protein complexes were analyzed by SDS-PAGE and immunoblotting using anti-phosphotyrosine antibodies. An anti-phosphotyrosine immunoprecipitation was also performed on pervanadate treated cell lysates to illustrate the full complement of tyrosine-phosphorylated proteins (PY IP). FIG. 1B: T-47D cells were treated as in FIG. 1A. Cells were lysed with (+) or without (−) 2 mM vanadate. MBP-.DEP-1 (wildtype DEP-1 fusion protein) and MBP.DEP-1 (CA) fusion protein were pre-incubated with (+) or without (−) 2 mM vanadate and added to cell lysates. Protein complexes were analyzed by SDS-PAGE and immunoblotting using anti-phosphotyrosine antibodies.

FIGS. 2A and 2B present immunoblots of tyrosine phosphorylated proteins trapped by DEP-1(DA) from pervanadate treated MDA-MB-231 breast tumor cells. FIG. 2A:

MDA-MB-231 cells were treated with 100 μM pervanadate for 20 minutes prior to lysis. MBP or MBP.DEP-1; MBP-.DEP-1(CS); and MBP.DEP-1(DA) fusion proteins were incubated with cell lysates and protein complexes were analyzed by SDS-PAGE and immunoblotting using anti-phosphotyrosine antibodies. FIG. 2B. Effects of vanadate on the interaction between tyrosine phosphorylated proteins with the DEP-1(DA) substrate-trapping mutant. MDA-MB-231 cells treated with pervanadate as described above were lysed in lysis buffer with (+) or without (−) 2 mM vanadate. MBP.DEP-1 and MBP.DEP-1(DA) fusion proteins were pre-incubated with (+) or without (−) 2 mM vanadate and added to cell lysates. Protein complexes were analyzed by SDS-PAGE and immunoblotting using anti-phosphotyrosine antibodies.

FIG. 4A: Cell lysates were immunoprecipitated with anti-DEP-1 monoclonal antibodies A3 and 143-41 and analyzed by immunoblot (IP DEP-1). Immunoblots probed with the polyclonal anti-DEP-1 antibody CS895A revealed the levels of DEP-1 in the immunoprecipitates (DEP-1) (upper immunoblot). Blots were stripped and re-probed for Met (Met) (lower immunoblot). FIG. 4B: Immunoblot analysis of the phosphorylation state of Met in the presence of wild type or mutant forms of DEP-1. Met was immunoprecipitated from the cell lysates using the polyclonal antibody 144 (IP Met). Immunoblots probed with the polyclonal antibody C-12, which is directed to the intracellular segment of Met, revealed the levels of CSF-MET in the immunoprecipitates (Met) (upper immunoblot). Immunoblots were stripped and re-probed with anti-phosphotyrosine antibodies (PY) (lower immunoblot).

FIG. 5A: 293 cells were transfected with 20 μg of CSF-MET DNA and 0, 1, 2.5, 5, 10 μg of DEP1 DNA or 10 μg of DEP-1(CS) DNA. Cell lysates (50 μg) were analyzed for the expression levels of DEP-1 (upper immunoblot) and Met (lower immunoblot). FIG. 5B: Site-specific dephosphorylation of Met by DEP-1. Met was immunoprecipitated using the polyclonal antibody 144 from the lysates of serum-starved 293 cells transfected as described above. Immunoblots probed with the polyclonal anti-Met antibody C-12 revealed a constant level of Met immunoprecipitated from the cell lysates (MET). This blot was stripped and re-probed with the phospho-specific antibody to Tyr$^{1349}$ in Met (Phospho-Met Y$^{1349}$). A duplicate blot was probed with anti-phosphotyrosine antibodies to illustrate the total phosphotyrosine content (PY), then sequentially stripped and re-probed with phospho-specific antibodies to examine the phosphorylation status of Tyr$^{1230}$, Tyr$^{1234}$, and Tyr$^{1235}$ (Phospho-Met Y$^{1230/34/35}$), and of Tyr$^{1365}$ (phospho-Met Y$^{1365}$). FIG. 5C: Immunoblot analysis of the association of Grb2 with Met. The immunoblots of Met immunoprecipitates described in FIG. 5B were probed with an antibody to Grb2 to reveal the level of Grb2 associated with Met (Met IP/Grb2 IB) (upper immunoblot). Cell lysates (50 μg) were also probed with an anti-Grb2 antibody to determine the level of expression of Grb2 in the transfected cells (Lysate) (lower immunoblot).

DETAILED DESCRIPTION OF THE INVENTION

Figure 1A:
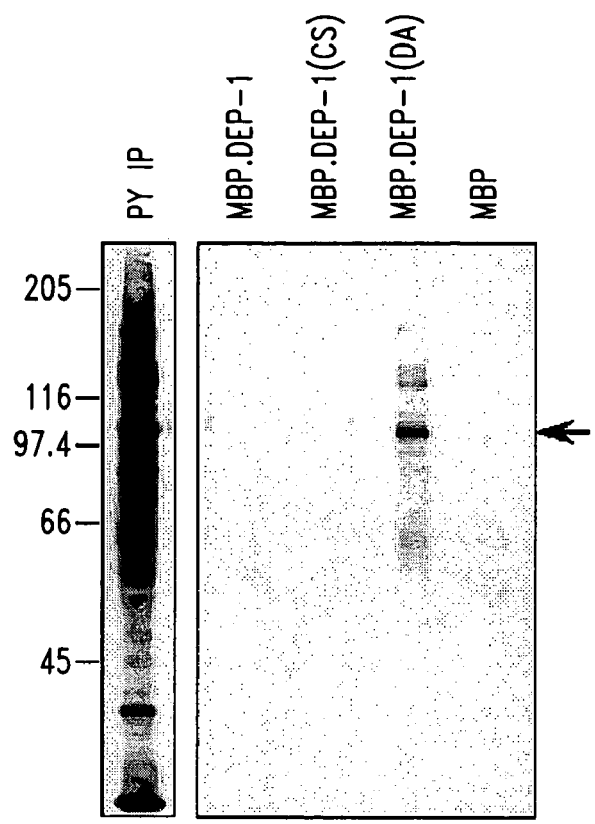
FIGS. 1A and 1B present immunoblot results of tyrosine phosphorylated proteins trapped by DEP-1(DA) from pervanadate-treated T-47D breast tumor cells.

The present invention is directed in part to the identification of an unexpected set of proteins with which DEP-1 specifically interacts to form heretofore unrecognized molecular complexes that can be isolated, and to related methods. As disclosed herein, DEP-1 specifically interacts with Met polypeptides, with the junctional component catenin p120$^{ctn}$, and with Gab1 polypeptides. Also disclosed herein is the specific interaction of DEP-1 with plakoglobin and with β-catenin.

Isolated complexes provided by the present invention may be used in a variety of contexts relevant to defining and molecularly manipulating biological signal transduction pathways, including defining therapeutic targets and also including, for example, determining additional molecular components of such pathways. In certain preferred embodiments the invention relates to screening assays for agents that alter (i.e., increase or decrease in a statistically significant manner) the interaction of a DEP-1 polypeptide with a DEP-1 substrate polypeptide, for example by altering the association in a complex of DEP-1 with a DEP-1 substrate, and/or by altering the dephosphorylation by DEP-1 of a DEP-1 substrate. Agents so identified will be useful for therapeutic intervention in contexts in which it is desirable to influence biological processes in which DEP-1 complexes play a role, for instance, cell growth or proliferation including cell cycle regulation and contact inhibition of cell growth, cellular differentiation including altered cellular morphogenesis or motility or other cellular activities characterized by alterations in cytoskeletal organization and/or in cellular gene expression, or cell survival including cellular responses to apoptotic stimuli.

Thus, and as described herein, protein complexes according to the present invention may comprise a DEP-1 polypeptide in specific association with a Met polypeptide (e.g., hepatocyte growth factor-receptor, HGF-R, also known as scatter factor receptor, SF-R, GenBank Acc. Nos. P08581 (SEQ ID NO:4), AAA59591 (SEQ ID NO:5), NM_000245 (SEQ ID NO:6); see OMIM (Online Mendelian Inheritance in Man) Acc. No. 164860 (Met proto-oncogene), [online], [retrieved from the Internet on Nov. 25, 2002] Internet <ncbi.nlm.nih.gov/entrez/query.fcgi?db=OMIM>) including a Met-derived polypeptide (SEQ ID NO:7) comprising the transmembrane and cytoplasmic domains of such a Met polypeptide (Zhu et al., 1994 *Cell Growth Differ.* 5(4): 359–366; amino acid positions 938–1408 of GenBank Acc. No. NP_000236; GenBank AAA59591); (see also Park et al., *Proc. Natl. Acad. Sci: USA* 84:6379–83 (1987)).

Met induces mitogenic, motogenic and morphogenic responses after ligand activation by recruiting a number of signaling and docking molecules and has been implicated in the phosphorylation of cell junction proteins. Disruption of normal signaling through Met has been implicated in certain cancers (see, e.g., Maulik et al., *Cytokine Growth Factor*

Rev. 13:41–59 (2002)). Ligand induced activation of Met by HGF/SF leads to the autophosphorylation of specific tyrosine residues within the PTK. Phosphorylation of Tyr$^{1234}$ and Tyr$^{1235}$ in the activation loop of Met is required for kinase activity, whereas phosphorylation of C-terminal tyrosine residues (Tyr$^{1349}$, Tyr$^{1356}$) is required for the recruitment of signaling and adapter molecules including Gab1 (reviewed in Furge et al., *Oncogene* 19:5582–89 (2000))). Additional C-terminal tyrosines such as Tyr$^{1365}$ appear to be important for mediating a morphogenic signal although the identity of proteins that interact with this site is currently unknown (Weidner et al., *Proc. Natl. Acad. Sci. USA* 92:2597–601 (1995); see also Kovalenko et al., *J. Biol. Chem.* 275:14119–23 (2000)). Also described herein is the surprising observation that DEP-1 preferentially dephosphorylates specific tyrosine residues in the C-terminal domain of Met. Without wishing to be bound by theory, such selective dephosphorylation of specific sites in the kinase may provide a mechanism by which DEP-1 attenuates particular signaling events emanating from Met, thus regulating the outcome of cellular responses induced by HGF/SF stimulation.

Met is the prototypic member of a small subfamily of receptor PTKs that includes Ron and the chicken homologue of Ron, Sea. HGF/SF is the ligand for Met, whereas macrophage stimulating protein (MSP) is the ligand for Ron and Sea. Members of this subfamily of PTKs are expressed in a variety of cell types including epithelial, endothelial, and hematopoietic cells. Interestingly, the expression pattern of DEP-1 overlaps with the expression pattern of these receptor PTKs consistent with a possible interaction between these enzymes under physiological conditions.

Following activation by HGF/SF, Met is able to exert a variety of effects by recruiting docking and signaling molecules (see, e.g., Vadnais et al., *J. Biol. Chem.* 277:48342–50 (2002). Epub Oct. 7, 2002). Phosphorylation of the tyrosine residues in the activation loop of the PTK domain potentiates the intrinsic kinase activity of Met, whereas phosphorylation of the two docking site tyrosine residues (Tyr$^{1349}$, Tyr$^{1356}$) allows for the recruitment of adaptor molecules including Grb2, SHC and Gab 1 and signaling enzymes including phosphotidylinositol 3-kinase (PI3K), phospholipase Cγ (PLC-γ), the PTK src, the PTP SHP2, as well as the transcription factor STAT3 (reviewed in Furge et al., supra). This multisubstrate docking site sequence is primarily responsible for Met-mediated signal transduction and chimeric receptors containing this sequence can induce mitogenic, motogenic and morphogenic responses similar to Met (Zhu et al., supra; Komada et al., *Oncogene* 8:2381–90 (1993); Weidner et al., *J. Cell Biol.* 121:145–54 (1993); Sachs et al., *J. Cell Biol.* 133:1095–107 (1996); see also, e.g., Giordano et al., *Nat. Cell Biol.* 4:720–24 (2002)). Cells expressing Met with mutations at Tyr$^{1349}$ and Tyr$^{1356}$ are unresponsive to HGF/SF stimulation in vitro (Ponzetto et al., *Cell* 77:261–71 (1994)), and transgenic mice with these mutations display a lethal phenotype that resembles the phenotype of mice lacking Met or HGF/SF (Maina et al., *Cell* 87:531–43 (1996)). Modulating the phosphorylation status of the multisubstrate docking site represents an important mechanism for regulating HGF/SF induced cellular responses. As described in greater detail in the Examples herein, DEP-1 preferentially dephosphorylated the docking site residue Tyr$^{1349}$.

The role of specific adaptor and signaling molecules in transducing Met signals has been studied extensively. The adapter protein Grb2 recruits SOS to activated receptor PTKs to induce Ras-MAP kinase signaling. In Met signaling Ras stimulation is necessary and sufficient to induce proliferation (Ponzetto et al., *J. Biol. Chem.* 271:14119–23 (1996)). Grb2 binds to Met directly at a binding site that contains phosphorylated Tyr$^{1356}$ (Fixman et al., *Oncogene* 10:237–49; Ponzetto et al. (1994), supra; Fournier et al., *J. Biol. Chem.* 271:22211–17 (1996)). In addition Grb2 can be recruited to Met via the adapter protein SHC (Pelicci et al., *Oncogene* 10:1631–38 (1995)). After Met activation the adapter molecule Gab 1 is strongly tyrosine phosphorylated and recruited to Met directly through Tyr$^{1349}$ (Weidner et al., *Nature* 384:173–76 (1996)) and indirectly via Grb2 bound to Tyr$^{1356}$ (Bardelli et al., *Oncogene* 15:3103–11 (1997); Nguyen et al., *J. Biol. Chem.* 272:20811–19 (1997); Lock et al., *J. Biol. Chem.* 31536–45 (2000)). Gab 1 can amplify and diversify Met signaling by recruiting additional signaling proteins such as PI3K, PLC-γ, SHP-2 and the adapter protein Crk. Tyrosine phosphorylation of Gab 1 at specific residues is required for the recruitment of the signaling molecules. Transgenic mice lacking Gab 1 display a lethal phenotype that resembles the phenotype of mice lacking Met or HGF/SF suggesting that Gab 1 is important for Met signaling in vivo (see, e.g., Sachs et al., *J. Cell Biol.* 150:1375–84 (2000); see also Baker et al., *Mol. Cell Biol.* 21:2393–403 (2001)).

As also disclosed herein, protein complexes according to the invention may comprise a DEP-1 polypeptide in specific association with, p120$^{ctn}$, a junctional component catenin polypeptide (e.g., GenBank Acc. Nos. AF062321 (SEQ ID NO:8), AF062317 (SEQ ID NO:9), AF062319 (SEQ ID NO:10), AF062338 (SEQ ID NO:11), AF062342 (SEQ ID NO:12); see OMIM (Online Mendelian Inheritance in Man) Acc. No. 601045 (catenin), [online][retrieved on Nov. 26, 2002]. Retrieved from the Internet:ncbi.nlm.nih.gov/entrez/query.fcgi?db=OMIM>). Also described herein is the association of DEP-1 with Gab1, an adaptor protein (e.g., GenBank Acc. No. NM_002039 (SEQ ID NO:13); see OMIM (Online Mendelian Inheritance in Man) Acc. No. 604439 (Gab1), [online], [retrieved on Nov. 25, 2002]. Retrieved from the Internet:URL:http://www.ncbi.nlm.nih-.gov/entrez/query.fcgi?db=OMIM>). Interactions between DEP-1 and plakoglobin (e.g., GenBank Acc. Nos. BC011865 (SEQ ID NO:14), Z68228 (SEQ ID NO:15), NM_021991 (SEQ ID NO: 22; see OMIM (Online Mendelian Inheritance in Man) Acc. No. 173325 (plakoglobin), [online][retrieved from the Internet on Nov. 25, 2002] Retrieved from the Internet:ncbi.nlm.nih.gov/entrez/query.fcgi?db=OMIM>), and between DEP-1 and β-catenin (e.g., GenBank Acc. No. NM_001904 (SEQ ID NO:16); see OMIM (Online Mendelian Inheritance in Man) Acc. No. 116806 (beta-catenin), [online], [retrieved on Nov. 25, 2002]; retrieved from the Internet:ncbi.nlm.nih.gov/entrez/query.fcgi?db=OMIM>) are also described herein (see also Shibamoto et al., *Cell Adhes. Commun.* 1:295–305 (1994); Holsinger et al., *Oncogene* 21:7067–76 (2002)).

Preferred embodiments of the present invention relate to DEP-1 polypeptides, which include the human DEP-1 polypeptide comprising the amino acid sequence set forth in GenBank Acc. No. U10886 (SEQ ID NO:2), or portions thereof that are capable of specific association with a DEP-1 substrate polypeptide, for instance, a polypeptide comprising the amino acid sequence of positions 997–1337 of SEQ ID NO:2 (as set forth in SEQ ID NO:3), or a truncated polypeptide which comprises at least the amino acid sequence set forth at positions 1205–1245 of SEQ ID NO:2, or a variant thereof as provided herein.

A truncated DEP-1 polypeptide or a variant of such a truncated polypeptide that comprises at least amino acids 1205–1245 of SEQ ID NO:2 may comprise, at either or both of the N-terminus and the C-terminus of the peptide defined by positions 1205–1245 of SEQ ID NO:2, a portion comprising a sequence of an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, or 146 or more of the amino acid residues as set forth in SEQ ID NO:2 that are situated N-terminal to and C-terminal to the fragment defined by positions 1205–1245, and such a polypeptide may further include amino acid substitutions, insertions or deletions at no more than 20%, more preferably no more than 15%, more preferably no more than 10%, still more preferably no more than 5% of the amino acids set forth in SEQ ID NO:2, so long as the polypeptide is capable of specific association with a DEP-1 substrate polypeptide. It should be noted that the DEP-1 polypeptide defined by positions 997–1337 of SEQ ID NO:2 comprises the DEP-1 cytoplasmic domain and that positions 1060–1296 of SEQ ID NO:2 comprise the DEP-1 PTP catalytic domain, which domains may be preferred DEP-1 polypeptides according to certain embodiments of the invention.

In certain embodiments, the present invention thus provides a truncated DEP-1 polypeptide for use in the instant compositions and methods, and in certain other embodiments the invention provides nucleic acids encoding such a truncated DEP-1 polypeptide. A truncated molecule may be any molecule that comprises less than a full-length version of the molecule. Truncated molecules provided by the present invention may include truncated biological polymers, and in preferred embodiments of the invention such truncated molecules may be truncated nucleic acid molecules or truncated polypeptides. Truncated nucleic acid molecules have less than the full-length nucleotide sequence of a known or described nucleic acid molecule. Such a known or described nucleic acid molecule may be a naturally occurring, a synthetic, or a recombinant nucleic acid molecule, so long as one skilled in the art would regard it as a full-length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

In other preferred embodiments, truncated molecules are polypeptides that comprise less than the full-length amino acid sequence of a particular protein or polypeptide component, for instance, a DEP-1 polypeptide or a DEP-1 substrate polypeptide as provided herein. As used herein "deletion" has its common meaning as understood by those familiar with the art, and may refer to molecules that lack one or more of a portion of a sequence from either terminus or from a non-terminal region, relative to a corresponding full-length molecule, for example, as in the case of truncated molecules provided herein. Truncated molecules that are linear biological polymers such as nucleic acid molecules or polypeptides may have one or more of a deletion from either terminus of the molecule and/or a deletion from a non-terminal region of the molecule. Such deletions may be deletions of 1–1500 contiguous nucleotide or amino acid residues, preferably 1–500 contiguous nucleotide or amino acid residues and more preferably 1–300 contiguous nucleotide or amino acid residues, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31–40, 41–50, 51–74, 75–100, 101–150, 151–200, 201–250 or 251–299 contiguous nucleotid or amino acid residues. In certain particularly preferred embodiments truncated nucleic acid molecules may have at least one deletion of approximately 270–330 contiguous nucleotides. In certain other particularly preferred embodiments truncated polypeptide molecules may have at least one deletion of 40–140 contiguous amino acids.

A DEP-1 polypeptide for use according to certain embodiments of the present invention comprises a polypeptide that binds to an antibody which specifically recognizes (e.g., binds to) a polypeptide that comprises the amino acid sequence set forth in SEQ ID NO:2. According to certain other embodiments a DEP-1 polypeptide comprises a polypeptide that binds to an antibody which specifically recognizes (e.g., binds to) a polypeptide that comprises the amino acid sequence set forth in SEQ ID NO:3.

Therefore, also contemplated by the present invention is the use according to certain embodiments of an antibody that specifically binds to a DEP-1 polypeptide, or the use of other molecules that specifically bind to a DEP-1 polypeptide and which may include peptides, polypeptides, and other non-peptide molecules that specifically bind to a DEP-1 polypeptide and in particularly preferred embodiments, to a polypeptide comprising the amino acid sequence of SEQ ID NO:2 or SEQ ID NO:3. As used herein, a molecule is said to "specifically bind" to a DEP-1 peptide or polypeptide if it reacts at a detectable level with the DEP-1 peptide or polypeptide, but does not react detectably with peptides containing an unrelated sequence or a sequence of a different phosphatase. Preferred binding molecules include antibodies, which may be, for example, polyclonal, monoclonal, single chain, chimeric, anti-idiotypic, or CDR-grafted immunoglobulins, or fragments thereof, such as proteolytically generated or recombinantly produced immunoglobulin F(ab')$_2$, Fab, Fv, and Fd fragments. Binding properties of an antibody to a DEP-1 may generally be assessed using immunodetection methods including, for example, an enzyme-linked immunosorbent assay (ELISA), immunoprecipitation, immunoblotting and the like, which maybe readily performed by those having ordinary skill in the art. In certain preferred embodiments, the invention method may relate to isolating a DEP-1 polypeptide with an antibody that specifically binds to the phosphatase; such embodiments may include without limitation methodologies for immuno-isolation (e.g., immunoprecipitation, immunoaffinity chromatography) and/or immunodetection (e.g., western blot).

Methods well known in the art may be used to generate antibodies, polyclonal antisera or monoclonal antibodies, that are specific for DEP-1; a number of DEP-1-specific antibodies are also commercially available. As used herein, an antibody is said to be "immunospecific" or to "specifically bind" a DEP-1 polypeptide if it reacts at a detectable level with DEP-1, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinity of an antibody for its cognate antigen is also commonly expressed as a dissociation constant $K_D$, and an anti-DEP-1 antibody specifically binds to DEP-1 if it binds with a $K_D$ of less than or equal to $10^{-4}$ M, more preferably less than or equal to about $10^{-5}$ M, more preferably less than or equal to about $10^{-6}$ M, still more preferably less than or equal to $10^{-7}$ M, and still more preferably less than or equal to $10^{-8}$ M. Affinities of binding partners or antibodies can be readily determined using conventional techniques, for example, those described by Scatchard et al. (*Ann. N.Y. Acad. Sci. USA* 51:660 (1949)) or by surface plasmon resonance (BIAcore, Biosensor, Piscataway, N.J.) (see, e.g., Wolff et al., *Cancer Res.* 53:2560–2565 (1993)).

Antibodies may generally be prepared by any of a variety of techniques known to those having ordinary skill in the art. See, e.g., Harlow et al., *Antibodies: A Laboratory Manual*, Cold Spring Harbor Laboratory (1988). In one such technique, an animal is immunized with an antigen to generate polyclonal antisera. Suitable animals include, for example, rabbits, sheep, goats, pigs, cattle, and may also include smaller mammalian species, such as mice, rats, and hamsters, or other species. An immunogen may be comprised of cells expressing DEP-1, purified or partially purified DEP-1 polypeptides or variants or fragments (e.g., peptides) thereof, or DEP-1 peptides. PTP peptides may be generated by proteolytic cleavage or may be chemically synthesized. For instance, nucleic acid sequences encoding DEP-1 polypeptides are provided herein, such that those skilled in the art may routinely prepare these polypeptides for use as immunogens. Polypeptides or peptides useful for immunization may also be selected by analyzing the primary, secondary, and tertiary structure of DEP-1 according to methods known to those skilled in the art, in order to determine amino acid sequences more likely to generate an antigenic response in a host animal. See, e.g., Novotny, 1991 *Mol. Immunol.* 28:201–207; Berzofsky, 1985 *Science* 229: 932–40.

Certain embodiments of the invention contemplate mutant DEP-1 polypeptides, including those that comprise at least one amino acid substitution in the amino acid sequence set forth in SEQ ID NO:2, which in certain preferred embodiments comprises substitution of the aspartate at position 1205 of SEQ ID NO:2 and/or substitution of the cysteine at position 1239 of SEQ ID NO:2. In certain particularly preferred embodiments aspartate at position 1205 is substituted with alanine. In certain particularly preferred embodiments cysteine at position 1239 is substituted with serine.

Portions of two polypeptide sequences (e.g., DEP-1 polypeptides, DEP-1 substrate polypeptides or other DEP-1 interacting or DEP-1 associating polypeptides) are regarded as "corresponding" amino acid sequences, regions, fragments or the like, based on a convention of numbering one sequence according to amino acid position number, and then aligning the sequence to be compared in a manner that maximizes the number of amino acids that match or that are conserved residues, for example, that remain polar (e.g., D, E, K, R, H, S, T, N, Q), hydrophobic (e.g., A, P, V, L, I, M, F, W, Y) or neutral (e.g., C, G) residues at each position. Similarly, a DNA sequence encoding a candidate polypeptide that is to be mutated as provided herein, or a portion, region, fragment or the like, may correspond to a known wildtype polypeptide-encoding DNA sequence according to a convention for numbering nucleic acid sequence positions in the known wildtype DNA sequence, whereby the candidate DNA sequence is aligned with the known DNA such that at least 70%, preferably at least 80% and more preferably at least 90% of the nucleotides in a given sequence of at least 20 consecutive nucleotides of a sequence are identical. In certain preferred embodiments, a candidate DNA sequence is greater than 95% identical to a corresponding known DNA sequence. In certain particularly preferred embodiments, a portion, region or fragment of a candidate DNA sequence is identical to a corresponding known DNA sequence. As is well known in the art, an individual whose DNA contains no irregularities (e.g., a common or prevalent form) in a particular gene responsible for a given trait may be said to possess a wildtype genetic complement (genotype) for that gene, while the presence of irregularities known as mutations in the DNA for the gene, for example, substitutions, insertions or deletions of one or more nucleotides, indicates a mutated or mutant genotype.

As noted above, in certain embodiments of the present invention a substrate trapping mutant PTP is provided in which the catalytic domain invariant aspartate and, optionally, at least one tyrosine residue are replaced, as provided in U.S. Pat. Nos. 5,912,138, 5,951,979, and PCT/US00/14211 (WO 00/75339), all incorporated by reference. Preferably the tyrosine residue that is replaced is located in the PTP catalytic domain, which refers to the approximately 250 amino acid region that is highly conserved among the various PTPs, as noted above (see also, e.g., Barford, 1998 *Ann. Rev. Biophys. Biomol. Struct.* 27:133; Jia, 1997 *Biochem. Cell Biol.* 75:17; Van Vactor et al., 1998 *Curr. Opin Genet. Devel.* 8:112). More preferably, the tyrosine residue is located in a PTP active site, which refers to the region within the PTP catalytic domain that contains the PTP signature motif and which also includes those amino acids that form the PTP binding site pocket or "cradle" for substrate binding and dephosphorylation, further including the invariant aspartate-containing loop (when present) and adjacent peptide backbone sequences that contribute to substrate recognition and catalysis (see, e.g., Jia, 1997).

Within the conserved catalytic domain is a unique signature sequence motif, $CX_5R$ (SEQ ID NO: 17), that is invariant among all PTPs. In a majority of PTPs, an 11 amino acid conserved sequence ([I/V]HCXAGXXR[S/T]G (SEQ ID NO: 18)) containing the signature sequence motif is found. The cysteine residue in this motif is invariant in members of the family and is essential for catalysis of the phosphotyrosine dephosphorylation reaction. It functions as a nucleophile to attack the phosphate moiety present on a phosphotyrosine residue of the incoming substrate. In certain embodiments the cysteine residue that is present in the PTP signature catalytic motif $CX_5R$ (SEQ ID NO: 17) is modified to yield a catalytically inactive PTP; typically the cysteine residue is replaced with serine as described, for example, by Sun et al. (1993 *Cell* 75:487–493), but other substitutions may also be made. If the cysteine residue is altered by site-directed mutagenesis to serine (e.g., in cysteine-to-serine or "CS" mutants) or alanine (e.g., cysteine-to-alanine or "CA" mutants), the resulting PTP is catalytically deficient but retains the ability to complex with, or bind, its substrate, at least in vitro.

Identification of the catalytic domain invariant aspartate residue in PTP sequences other than those disclosed in Barford et al. (1995), or of the cysteine residue that is present in the PTP signature catalytic motif $CX_5R$ (SEQ ID NO: 17), may be achieved by comparing sequences using computer algorithms well known to those having ordinary skill in the art, such as GENEWORKS, Align or the BLAST algorithm (Altschul, *J. Mol. Biol.* 219:555–565, 1991; Henikoff and Henikoff, *Proc. Natl. Acad. Sci. USA* 89:10915–10919, 1992), which is available at the NCBI website. Therefore it should be recognized that mutant DEP-1 polypeptides other than those specifically described herein can readily be made by aligning the amino acid sequence of a DEP-1 catalytic domain with the amino acid sequence of DEP-1 polypeptides that are described herein (including those provided by the cited references), identifying the catalytic domain invariant aspartate residue and, optionally, at least one tyrosine residue, and changing these residues, for example by site-directed mutagenesis of DNA encoding the PTP.

Accordingly, certain embodiments of the invention pertain in part to PTPs in which the invariant aspartate residue is replaced with an amino acid which does not cause significant alteration of the Km of the enzyme (that is, does not cause a statistically significant increase or decrease of the Km) but which results in a reduction in Kcat to less than 1 per minute (less than 1 min$^-$). That is, replacement of the wildtype aspartate residue results in a reduction of Kcat such that the Kcat of the substrate trapping mutant is less than 1 per minute, which is a reduction in Kcat compared with the wildtype PTP. As understood by persons skilled in the art, the Michaelis constant Km is a term that indicates a measure of the substrate concentration required for effective catalysis to occur and is the substrate concentration at which the reaction is occurring at one-half its maximal rate (½ Vmax). The Kcat of an enzyme provides a direct measure of the catalytic production of product under optimum conditions (particularly, saturated enzyme). The reciprocal of Kcat is often referred to as the time required by an enzyme to "turn over" one substrate molecule, and Kcat is sometimes called the turnover number. Vmax and Kcat are directly proportional; therefore, if, for example, Kcat of a substrate trapping mutant is reduced by $10^4$ compared to the Kcat of the wildtype enzyme, Vmax is also decreased by a factor of $10^4$. These substrate trapping mutant PTPs retain the ability to form a complex with, or bind to, their tyrosine phosphorylated substrates, but are catalytically attenuated (i.e., a substrate trapping mutant PTP retains a similar Km to that of the corresponding wildtype PTP, but has a Vmax which is reduced by a factor of at least $10^{2-10.5}$ relative to the wildtype enzyme, depending on the activity of the wildtype enzyme relative to a Kcat of less than 1 min$^-$). This attenuation includes catalytic activity that is either reduced or abolished relative to the wildtype PTP. For example, the invariant aspartate residue can be changed or mutated to an alanine, valine, leucine, isoleucine, proline, phenylalanine, tryptophan, methionine, glycine, serine, threonine, cysteine, tyrosine, asparagine, glutamine, lysine, arginine or histidine.

Without wishing to be bound by theory, such a substrate trapping mutant PTP may reduce the activity of the corresponding wildtype PTP by forming a complex with the tyrosine phosphorylated protein substrate of the wildtype PTP, thereby rendering the substrate unavailable for catalytic dephosphorylation by the wildtype enzyme. The substrate trapping mutant PTP thus binds to the phosphoprotein substrate without dephosphorylating it (or catalyzing dephosphorylation at a greatly reduced rate), thereby blocking the activity of the dephosphorylated protein substrate and reducing its downstream effects. As used herein, "reducing" includes both reduction and complete abolishment of one or more activities or functions of the phosphorylated protein substrate.

The preferred substrate trapping mutant PTPs described herein, in which the invariant aspartate residue is replaced with an amino acid which does not cause significant alteration of the Km of the enzyme but which results in a reduction in Kcat to less than 1 per minute (less than 1 min$^{-1}$), and/or in which at least one tyrosine residue is replaced with an amino acid that is not capable of being phosphorylated, may additionally or alternatively comprise other mutations. In particularly preferred embodiments, such additional mutations relate to substitutions, insertions or deletions (most preferably substitutions) that assist in stabilizing the PTP/substrate complex. For example, mutation of the serine/threonine residue in the signature motif to an alanine residue (S/T→A mutant) may change the rate-determining step of the PTP-mediated substrate dephosphorylation reaction. For the unmodified PTP, formation of the transition state may be rate-limiting, whereas in the case of the S/T→A mutant, the breakdown of the transition state may become rate-limiting, thereby stabilizing the PTP/substrate complex. Such mutations may be valuably combined with the replacement of the PTP catalytic domain invariant aspartate residue and the replacement of PTP tyrosine as provided herein, for example, with regard to stabilizing the PTP-substrate complex and facilitating its isolation. As another example, substitution of any one or more other amino acids present in the wildtype PTP that are capable of being phosphorylated as provided herein (e.g., serine, threonine, tyrosine) with an amino acid that is not capable of being phosphorylated may be desirable, with regard to the stability of a PTP-substrate complex.

As noted above, in certain embodiments the present invention relates to substrate trapping mutant PTPs in which catalytic domain invariant aspartate and at least one tyrosine residue are replaced, wherein the tyrosine is replaced with an amino acid that is not capable of being phosphorylated. The amino acid that is not capable of being phosphorylated may, in preferred embodiments, be alanine, cysteine, aspartic acid, glutamine, glutamic acid, phenylalanine, glycine, histidine, isoleucine, lysine, leucine, methionine, asparagine, proline, arginine, valine or tryptophan. The desirability of the tyrosine replacement derives from the observation that under certain conditions in vivo, a PTP enzyme may itself undergo tyrosine phosphorylation in a manner that can alter interactions between the PTP and other molecules, including PTP substrates (e.g., WO 00/75339).

DEP-1 substrate polypeptides as provided herein include any naturally or non-naturally tyrosine-phosphorylated peptide, polypeptide or protein that can specifically associate with, bind to and/or be dephosphorylated by a DEP-1 polypeptide as provided herein. Thus, in addition to substitution of DEP-1 invariant aspartate (e.g., position 1205 of SEQ ID NO:2 or a corresponding amino acid in a truncated DEP-1 polypeptide) and/or of DEP-1 $CX_5R$ cysteine (e.g., position 1239 of SEQ ID NO:2 or a corresponding amino acid in a truncated DEP-1 polypeptide), replacement of a tyrosine residue found in the wildtype DEP-1 amino acid sequence with another amino acid as provided herein may stabilize the complex formed by the mutant DEP-1 polypeptide and the DEP-1 substrate polypeptide such that the amount of complex that is present increases and/or the affinity of the mutant DEP-1 for the substrate increases, relative to the amount of complex formed using a DEP-1 polypeptide in which the tyrosine residue is not replaced.

As noted above, in certain embodiments the present invention exploits mutant DEP-1 polypeptides described herein (e.g., substrate trapping mutants) to provide a method of screening for an agent that alters (i.e., increases or decreases in a statistically significant manner relative to an appropriate control as will be known to the ordinarily skilled artisan) an activity or interaction (e.g., binding to form a complex or catalytic dephosphorylation) between a tyrosine phosphorylated protein that is a substrate of a wildtype DEP-1 and the DEP-1 polypeptide, which in preferred embodiments will be a method of screening for an inhibitor of an interaction between a DEP-1 polypeptide and a DEP-1 substrate polypeptide.

According to this aspect of the invention, a sample comprising at least one tyrosine phosphorylated protein (e.g., a DEP-1 substrate polypeptide as described herein such as a Met polypeptide, a p120$^{ctn}$ polypeptide or a Gab 1 polypeptide that is capable of specific association with, and optionally dephosphorylation by, an appropriate DEP-1 polypeptide) or at least one polypeptide (e.g., a plakoglobin or a β-catenin polypeptide as provided herein) that is capable of specific association with a DEP-1 polypeptide, is combined with at least one DEP-1 polypeptide, for example a substrate trapping mutant DEP-1 as provided herein, and the presence or absence of a complex comprising the substrate and the DEP-1 polypeptide is determined.

The binding interaction between a DEP-1 polypeptide and a DEP-1 substrate polypeptide or other interacting polypeptide may thus result in the formation of a complex, which refers to the affinity interaction of the DEP-1 and the DEP-1 substrate. A complex may include a signaling complex, which refers to any complex that, by virtue of its formation, its stable association and/or its dissociation directly or indirectly provides a biological signal. Such signals may include, for example by way of illustration and not limitation, intracellular and/or intercellular events that lead to molecular binding, covalent or non-covalent modification of molecular structure, gene expression, genetic recombination, genetic integration, nucleic acid synthesis or subcellular particle assembly, and may also include endocytic, phagocytic, nucleolytic, proteolytic, lipolytic, hydrolytic, catalytic, or other regulatory events.

Determination of the presence of a stable complex between a DEP-1 polypeptide and a DEP-1 substrate polypeptide (or other DEP-1-interacting polypeptide) refers to the use of any methodology known in the art for demonstrating an intermolecular interaction between a PTP and a PTP substrate according to the present disclosure. Such methodologies may include, by way of illustration and not limitation, co-purification, co-precipitation, co-immunoprecipitation, radiometric or fluorimetric assays, western immunoblot analyses, affinity capture including affinity techniques such as solid-phase ligand-counterligand sorbent techniques, affinity chromatography and surface affinity plasmon resonance, and the like. For these and other useful affinity techniques, see, for example, Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques. A DEP-1 polypeptide may interact with a DEP-1 substrate polypeptide, or with another DEP-1-interacting polypeptide, via specific binding if the DEP-1 binds the substrate (or interacting polypeptide) with a $K_a$ of greater than or equal to about $10^4$ M$^{-1}$, preferably of greater than or equal to about $10^5$ M$^{-1}$, more preferably of greater than or equal to about $10^6$ M$^{-1}$ and still more preferably of greater than or equal to about $10^7$ M$^{-1}$ to $10^9$ M$^{-1}$. Affinities of binding partners such as a DEP-1 polypeptide and a DEP-1 substrate polypeptide can be readily determined using conventional techniques, for example by surface plasmon resonance and those described by Scatchard et al., *Ann. N.Y. Acad. Sci.* 51:660 (1949). Similarly, as described above for the affinity of an antibody and its cognate antigen, affinity of DEP-1 for its substrate may be expressed as a dissociation constant $K_D$, and DEP-1 specifically binds to a DEP-1 substrate if it binds with a $K_D$ of less than or equal to $10^{-4}$ M, more preferably less than or equal to about $10^{-5}$ M, more preferably less than or equal to about $10^{-6}$ M, still more preferably less than or equal to $10^{-7}$ M, and still more preferably less than or equal to $10^{-8}$ M.

Modification of DNA may be performed by a variety of methods, including site-specific or site-directed mutagenesis of DNA encoding the PTP (e.g., a DEP-1 polypeptide as provided herein) and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (e.g., a member of the PTP family). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. Additional disclosure relating to site-directed mutagenesis may be found, for example, in Kunkel et al. (*Methods in Enzymol.* 154:367, 1987); and in U.S. Pat. Nos. 4,518,584 and 4,737,462. The heteroduplex is introduced into appropriate bacterial cells, and clones that include the desired mutation are selected. The resulting altered DNA molecules may be expressed recombinantly in appropriate host cells to produce the modified protein.

Specific substitutions of individual amino acids through introduction of site-directed mutations are well-known and may be made according to methodologies with which those having ordinary skill in the art will be familiar. The effects on catalytic activity of the resulting mutant DEP-1 polypeptide may be determined empirically merely by testing the resulting modified protein for the preservation of the Km and reduction of Kcat to less than 1 per minute as provided herein and as previously disclosed (e.g., WO98/04712; Flint et al., 1997 *Proc. Nat. Acad. Sci.* 94:1680). The effects on the ability to tyrosine phosphorylate the resulting mutant PTP molecule can also be determined empirically merely by testing such a mutant for the presence of phosphotyrosine, as also provided herein, for example, following exposure of the mutant to conditions in vitro or in vivo where it may act as a PTK acceptor.

Although the specific examples of mutant DEP-1 polypeptides described herein are DA (aspartate to alanine) mutants, YF (tyrosine to phenylalanine) mutants, CS mutants and combinations thereof, it will be understood that the subject invention substrate trapping mutant DEP-1 polypeptides are not limited to these amino acid substitutions. The invariant aspartate residue can be changed, for example by site-directed mutagenesis, to any amino acid that does not cause significant alteration of the Km of the enzyme but which results in a reduction in Kcat to less than 1 per minute (less than 1 min$^-$). For example, the invariant aspartate residue can be changed or mutated to an alanine, valine, leucine, isoleucine, proline, phenylalanine, tryptophan, methionine, glycine, serine, threonine, cysteine, tyrosine, asparagine, glutamine, lysine, arginine or histidine, or other natural or non-natural amino acids known in the art including derivatives, variants and the like. Similarly, substitution of at least one tyrosine residue may be with any amino acid that is not capable of being phosphorylated (i.e., stable, covalent modification of an amino acid side chain at a hydroxyl with a phosphate group), for example alanine, cysteine, aspartic acid, glutamine, glutamic acid, phenylalanine, glycine, histidine, isoleucine, lysine, leucine, methionine, asparagine, proline, arginine, valine or tryptophan, or other natural or non-natural amino acids known in the art including derivatives, variants and the like.

The nucleic acids of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A nucleic acid molecule encoding a DEP-1 polypeptide, or a substrate trapping mutant DEP-1 in which the wildtype protein tyrosine phosphatase catalytic domain invariant aspartate residue is replaced with an amino acid which does not cause significant alteration of the Km of the enzyme but which results in a reduction in Kcat to less than 1 per minute, and in which at least one wildtype tyrosine residue is replaced with an amino acid that is not capable of being phosphorylated, may be identical to the coding sequence known in the art for DEP-1 (e.g., SEQ ID NO:1), or may be a different coding sequence, which, as a result of the redundancy or degeneracy of the genetic code, encodes the same PTP.

According to certain embodiments of the present invention, a DEP-1 polypeptide may be encoded by a polynucleotide that hybridizes under moderately stringent conditions to a nucleic acid molecule which comprises a nucleotide sequence that is a reverse complement of SEQ ID NO:1. Suitable moderately stringent conditions include, for example, prewashing in a solution of 5×SSC, 0.5% SDS, 1.0 mM EDTA (pH 8.0); hybridizing at 50° C.–70° C., 5×SSC, for 1–16 hours (e.g., overnight); followed by washing once or twice at 22–65° C. for 20–40 minutes with one or more each of 2×, 0.5× and 0.2×SSC containing 0.05–0.1% SDS. By way of example, conditions for a moderately stringent wash may include 0.2×SSC and 0.1% SDS for 15 minutes at 42° C. For additional stringency, conditions may include a wash in 0.1×SSC and 0.1% SDS at 50–70° C. for 15–40 minutes. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences, length, and base composition of the probe used, and of the blotted, proband nucleic acid sample.

The present invention further relates to variants of the herein described nucleic acids which encode fragments, analogs and derivatives of a DEP-1 polypeptide, including a mutated DEP-1 such as a substrate trapping mutant DEP-1 or a catalytically inactive DEP-1. The variants of the nucleic acids encoding DEP-1 polypeptides may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded PTP polypeptide.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation. Other equivalents can be prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

The present invention further relates to DEP-1 polypeptides including substrate trapping mutant PTPs, and in particular to methods for producing recombinant DEP polypeptides by culturing host cells containing DEP-1 expression constructs, and to isolated recombinant DEP-1 polypeptides. The polypeptides and nucleic acids of the present invention are preferably provided in an isolated form, and in certain preferred embodiments are purified to homogeneity. The terms "fragment," "derivative" and "analog" when referring to DEP-1 polypeptides or fusion proteins, including substrate trapping mutant DEP-1 polypeptides, refers to any DEP-1 polypeptide or fusion protein that retains essentially the same biological function or activity as such polypeptide (e.g., ability to specifically associate with a DEP-1 substrate polypeptide or other DEP-1 associating polypeptide). Thus, an analog includes a proprotein that can be activated by cleavage of the proprotein portion to produce an active DEP-1 polypeptide. The polypeptides of the present invention may be recombinant polypeptides or synthetic polypeptides, and are preferably recombinant polypeptides.

A fragment, derivative or analog of a DEP-1 polypeptide or fusion protein, including substrate trapping mutant DEP-1, may be (i) one in which one or more of the amino acid residues are substituted with a conserved or non-conserved amino acid residue (preferably a conserved amino acid residue), and such substituted amino acid residue may or may not be one encoded by the genetic code, or (ii) one in which one or more of the amino acid residues includes a substituent group, or (iii) one in which the DEP-1 polypeptide is fused with another compound, such as a compound to increase the half-life of the polypeptide (e.g., polyethylene glycol), or (iv) one in which additional amino acids are fused to the DEP-1 polypeptide, including amino acids that are employed for purification of the DEP-1 polypeptide or a proprotein sequence. Such fragments, derivatives and analogs are deemed to be within the scope of those skilled in the art from the teachings herein.

These and related properties of a DEP-1 polypeptide may be advantageously engineered into such a polypeptide where a particular use is contemplated. For example, according to certain embodiments of the invention there is provided a method of altering transduction of a biological signal in a cell comprising introducing into a cell a DEP-1 polypeptide that is capable of specific association with a DEP-1 substrate polypeptide under conditions and for a time sufficient to permit formation of a complex comprising the DEP-1 polypeptide in specific association with the substrate. Accordingly, related embodiments of the invention contemplate DEP-1 polypeptides that are fusion proteins comprising a truncated DEP-1 polypeptide domain as provided herein that is capable of specific association with a DEP-1 substrate, fused to a domain selected to deliver the polypeptide into a cell. A number of such polypeptide domains are known to the art (e.g., Mahat et al., 1999 Curr. Opin. Mol. Ther. 1:226; Snyder et al., 2001 Curr. Opin. Mol. Ther. 3:147; Gariepy et al., 2001 Trends Biotechnol. 19:21).

Alternatively, established methodologies for introducing into a cell a DEP-1 polypeptide that is not a targeted fusion protein may be employed. For example, Chariot™ is a transfection method that quickly and efficiently delivers biologically active proteins, peptides, and antibodies directly into cultured mammalian cells. The Chariot™ peptide (available from Active Motif, Carlsbad, Calif.) forms a non-covalent bond with the macromolecule of interest, which stabilizes the protein, protecting it from degradation, and preserving its natural characteristics during the transfection process (Morris et al. J. Biol. Chem. 274 (35): 24941–46 (1999); Morris, M. et al. Nature Biotech, 19: 1173–76 (2001)). After delivery, the complex dissociates, leaving the macromolecule biologically active and free to proceed to its target organelle. As another example, Photochemical Internalization (PCI) may be employed for delivery of macromolecules into the cytoplasm, including proteins (e.g., Selbo et al., Int. J. Cancer 87:853–59 (2000); Selbo et al., Tumour Biol. 23:103–12 (2002). Protein transduction technology has also been reviewed recently (Wadia & Dowdy, 2002 Curr Opin Biotechnol. 13(1):52–56) and its applicability to introducing a DEP-1 polypeptide into a cell is contemplated by the present invention.

The polypeptides of the present invention include PTP polypeptides and fusion proteins having amino acid sequences that are identical or similar to PTP sequences known in the art. For example by way of illustration and not limitation, the human PTP polypeptides (including substrate trapping mutant PTPs) referred to below in the Examples are contemplated for use according to the instant invention, as are polypeptides having at least 70% similarity (preferably 70% identity), more preferably 80% similarity (more preferably 80% identity), more preferably 90% similarity (more preferably 90% identity), more preferably 95% similarity (still more preferably 95% identity), and still more preferably 98% similarity (still more preferably 98% identity) to the polypeptides described in references cited herein and in the Examples and to portions of such polypeptides, wherein such portions of a PTP polypeptide generally contain at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide (e.g., using GENEWORKS, Align or the BLAST algorithm, as described above). Fragments or portions of the polypeptides of the present invention may be employed for producing the corresponding full-length polypeptide by peptide synthesis; therefore, the fragments may be employed as intermediates for producing the full-length polypeptides. Fragments or portions of the nucleic acids of the present invention may be used to synthesize full-length nucleic acids of the present invention.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition, and still be isolated in that such vector or composition is not part of the natural environment for the nucleic acid or polypeptide. The term "gene" means the segment of DNA involved in producing a polypeptide chain; it includes regions preceding and followin the coding region "leader and trailer" as well as intervening sequences (introns) between individual coding segments (exons).

As described herein, certain embodiments of the invention contemplate a fusion protein comprising a polypeptide of interest that is fused to a DEP-1 polypeptide, which fusion protein is encoded by nucleic acids that have the DEP-1 polypeptide coding sequence fused in frame to an additional coding sequence. The presence of such a fusion domain joined to the DEP-1 polypeptide may permit, for example by way of illustration and not limitation, detection, isolation and/or purification of the DEP-1 fusion protein by protein-protein affinity, metal affinity or charge affinity-based polypeptide purification, or by specific protease cleavage of a fusion protein containing a fusion sequence that is cleavable by a protease such that the DEP-1 polypeptide is separable from the fusion protein.

Thus, DEP-1 polypeptides may include PTP fusion proteins that comprise affinity tag polypeptide sequences, which refers to polypeptides or peptides added to DEP-1 to facilitate detection and isolation of the PTP via a specific affinity interaction with a ligand. The ligand may be any molecule, receptor, counterreceptor, antibody or the like with which the affinity tag may interact through a specific binding interaction as provided herein. Such peptides include, for example, poly-His or the antigenic identification peptides described in U.S. Pat. No. 5,011,912 and in Hopp et al., (1988 Bio/Technology 6:1204), or the XPRESS™ epitope tag (Invitrogen, Carlsbad, Calif.). The affinity sequence may be a hexa-histidine tag as supplied, for example, by a pBAD/His (Invitrogen) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 Cell 37:767).

PTP fusion proteins may further comprise immunoglobulin constant region polypeptides added to PTP to facilitate detection, isolation and/or localization of PTP. The immunoglobulin constant region polypeptide preferably is fused to the C-terminus of a PTP polypeptide. General preparation of fusion proteins comprising heterologous polypeptides fused to various portions of antibody-derived polypeptides (including the Fc domain) has been described, e.g., by Ashkenazi et al. (Proc. Natl. Acad. Sci. USA 88:10535, 1991) and Byrn et al. (Nature 344:677, 1990). A gene fusion encoding the PTP:Fc fusion protein is inserted into an appropriate expression vector. In certain embodiments of the invention, PTP:Fc fusion proteins may be allowed to assemble much like antibody molecules, whereupon interchain disulfide bonds form between Fc polypeptides, yielding dimeric PTP fusion proteins.

PTP fusion proteins having specific binding affinities for pre-selected antigens by virtue of fusion polypeptides comprising immunoglobulin V-region domains encoded by DNA sequences linked in-frame to sequences encoding PTP are also within the scope of the invention, including variants and fragments thereof as provided herein. General strategies for the construction of fusion proteins having immunoglobulin V-region fusion polypeptides are disclosed, for example, in EP 0318554; U.S. Pat. No. 5,132,405; U.S. Pat. No. 5,091,513; and U.S. Pat. No. 5,476,786.

The expressed recombinant DEP-1 polypeptides or fusion proteins (including substrate trapping mutant DEP-1) may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed recombinant DEP-1 polypeptides or fusion proteins can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The nucleic acid of the present invention may also encode a fusion protein comprising a PTP polypeptide fused to other polypeptides having desirable affinity properties, for example an enzyme such as glutathione-S-transferase. As another example, PTP fusion proteins may also comprise a PTP polypeptide fused to a *Staphylococcus aureus* protein A polypeptide; protein A encoding nucleic acids and their use in constructing fusion proteins having affinity for immunoglobulin constant regions are disclosed generally, for example, in U.S. Pat. No. 5,100,788. Other useful affinity polypeptides for construction of PTP fusion proteins may include streptavidin fusion proteins, as disclosed, for example, in WO 89/03422; U.S. Pat. No. 5,489,528; U.S. Pat. No. 5,672,691; WO 93/24631; U.S. Pat. No. 5,168,049; U.S. Pat. No. 5,272,254 and elsewhere, and avidin fusion proteins (see, e.g., EP 511,747). As provided herein and in the cited references, PTP polypeptide sequences, including substrate trapping mutant PTPs, may be fused to fusion polypeptide sequences that may be full length fusion polypeptides and that may alternatively be variants or fragments thereof.

The present invention also contemplates PTP fusion proteins that contain polypeptide sequences that direct the fusion protein to the cell nucleus, to reside in the lumen of the endoplasmic reticulum (ER), to be secreted from a cell via the classical ER-Golgi secretory pathway (see, e.g., von Heijne, *J. Membrane Biol.* 115:195–201, 1990), to be incorporated into the plasma membrane, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar (See, e.g., Rothman, *Nature* 372:55–63, 1994, Adrani et al., 1998 *J. Biol. Chem.* 273:10317, and references cited therein.). Accordingly, these and related embodiments are encompassed by the instant compositions and methods directed to targeting a polypeptide of interest to a predefined intracellular, membrane or extracellular localization.

The present invention also relates to vectors and to constructs that include nucleic acids of the present invention, and in particular to "recombinant expression constructs" that include any nucleic acids encoding DEP-1 polypeptides according to the invention as provided above; to host cells which are genetically engineered with vectors and/or constructs of the invention and to the production of DEP-1 polypeptides and fusion proteins of the invention, or fragments or variants thereof, by recombinant techniques. DEP-1 polypeptides can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described, for example, by Sambrook, et al., *Molecular Cloning: A Laboratory Manual*, Third Edition, Cold Spring Harbor, N.Y., (2001).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression constructs for bacterial use are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice. Any other plasmid or vector may be used as long as they are replicable and viable in the host.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotech, Madison, Wis., USA). These pBR322 "backbone" sections are combined with an appropriate promoter and the structural sequence to be expressed.

Following transformation of a suitable host strain and growth of the host strain to an appropriate cell density, the selected promoter, if it is a regulated promoter as provided herein, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Thus, for example, the nucleic acids of the invention as provided herein may be included in any one of a variety of expression vector constructs as a recombinant expression construct for expressing a DEP-1 polypeptide. Such vectors and constructs include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (2001 *Molecular Cloning*, Third Ed., Cold Spring Harbor Laboratory, Plainview, N.Y.); Maniatis et al. (1982 *Molecular Cloning*, Cold Spring Harbor Laboratory, Plainview, N.Y.); and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a DEP-1 polypeptide is described herein.

As noted above, in certain embodiments the vector may be a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980–990 (1989), or any other promoter (e.g., cellular promoters such as eukaryotic cellular promoters including, but not limited to, the histone, pol III, and β-actin promoters). Other viral promoters that may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14x, VT-19-17-H2, ψCRE, ψCRIP, GP+E-86, GP+envAm12, and DAN cell lines as described in Miller, *Human Gene Therapy*, 1:5–14 (1990), which is incorporated herein by reference in its entirety. The vector may transduce the packaging cells through any means known in the art. Such means include, but are not limited to, electroporation, the use of liposomes, and calcium phosphate precipitation. In one alternative, the retroviral plasmid vector may be encapsulated into a liposome, or coupled to a lipid, and then administered to a host.

The producer cell line generates infectious retroviral vector particles that include the nucleic acid sequence(s) encoding the DEP-1 polypeptides or fusion proteins. Such retroviral vector particles then may be employed, to transduce eukaryotic cells, either in vitro or in vivo. The transduced eukaryotic cells will express the nucleic acid sequence(s) encoding the DEP-1 polypeptide or fusion protein. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, bronchial epithelial cells and various other culture-adapted cell lines.

As another example of an embodiment of the invention in which a viral vector is used to prepare the recombinant DEP-1 expression construct, in one preferred embodiment, host cells transduced by a recombinant viral construct directing the expression of DEP-1 polypeptides or fusion proteins may produce viral particles containing expressed PTP polypeptides or fusion proteins that are derived from portions of a host cell membrane incorporated by the viral particles during viral budding. In another preferred embodiment, PTP encoding nucleic acid sequences are cloned into a baculovirus shuttle vector, which is then recombined with a baculovirus to generate a recombinant baculovirus expression construct that is used to infect, for example, Sf9 host cells, as described in *Baculovirus Expression Protocols, Methods in Molecular Biology* Vol. 39, Christopher D. Richardson, Editor, Human Press, Totowa, N.J., 1995; Piwnica-Worms, "Expression of Proteins in Insect Cells Using Baculoviral Vectors," Section II in Chapter 16 in: *Short Protocols in Molecular Biology*, $2^{nd}$ Ed., Ausubel et al., eds., John Wiley & Sons, New York, N.Y., 1992, pages 16–32 to 16–48.

In another aspect, the present invention relates to host cells containing the above described recombinant DEP-1 expression constructs. Host cells are genetically engineered (transduced, transformed, or transfected) with the vectors and/or expression constructs of this invention that may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding DEP-1 polypeptides or DEP-1 fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. The invention is therefore directed in part to a method of producing a recombinant DEP-1 polypeptide, by culturing a host cell comprising a recombinant expression construct that comprises at least one promoter operably linked to a nucleic acid sequence encoding the DEP-1 polypeptide, wherein the promoter may be a regulated promoter as provided herein, for example a tetracylcine-repressible promoter. In certain embodiments the recombinant expression construct is a recombinant viral expression construct as provided herein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of PTP expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

In certain particularly preferred embodiments, the present invention provides host cells capable of expressing a DEP-1 polypeptide following a growth period for cell propagation. By way of background, attempts to express DEP-1 constitutively in breast cells and macrophages (Keane et al., supra; Osborne et al., supra) have apparently been hindered by DEP-1-mediated growth inhibition, precluding development of stable cell lines. In order to overcome this limitation, according to the present invention a recombinant expression construct is provided that comprises a regulated promoter that is operably linked to a polynucleotide encoding a DEP-1 polypeptide. Preferably the regulated promoter is an inducible promoter, and still more preferably the promoter is a tightly regulated promoter. According to non-limiting theory, the use of a tightly regulated promoter that permits little or no transcription of the DEP-1-encoding polynucleotide permits growth of host cells that have stably incorporated the subject invention recombinant expression construct, such that cell growth is not impaired by the growth inhibitory effects of DEP-1 polypeptides. Further according to theory, only at a desired time, for instance after a population of host cells has been grown to a useful quantity, can DEP-1 expression be induced by contacting the cells with an appropriate inducing agent that activates the inducible promoter or the tightly regulated promoter. Such host cells may then be employed in the methods of the present invention, such as screening methods for agents that alter DEP-1 interaction with substrates, or that alter DEP-1 dephosphorylation of substrates. Preferably the host cell can be adapted to sustained propagation in culture to yield a cell line according to art-established methodologies. In certain preferred embodiments the cell line is an immortal cell line, which refers to a cell line that can be repeatedly (and at least ten times while remaining viable) passaged in culture following log-phase growth. In other preferred embodiments the host cell used to generate a cell line according to the invention is a cell that is capable of unregulated growth, such as a cancer cell, or a transformed cell, or a malignant cell.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J. Bacteriology* 177:4121–30 (1995); Smith et al., *J. Biol. Chem.* 253: 6931–33 (1978); Hirsh et al., *Cell* 11:545–50 (1977)), which controls the arabinose metabolic pathway. A variety of vectors employing this system are commercially available. Other examples of tightly regulated promoter-driven expression systems include PET Expression Systems (U.S. Pat. No. 4,952,496) available from Stratagene (La Jolla, Calif.) or tet-regulated expression systems (Gossen & Bujard, *Proc. Natl. Acad. Sci. USA* 89:5547–51 (1992) and Gossen et al., *Science* 268:1766–69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (e.g., Sauer, 1998 *Methods* 14:381; Furth, 1997 *J. Mamm. Gland Biol. Neoplas.* 2:373), which may also be employed for host cell immortalization (e.g., Cascio, 2001 *Artif. Organs* 25:529).

Identification of nucleic acid molecules for use as antisense agents, which includes antisense oligonucleotides and ribozymes specific for nucleic acid sequences encoding DEP-1 (including substrate trapping mutant DEP-1) or variants or fragments thereof; and of DNA oligonucleotides encoding DEP-1 genes (including substrate trapping mutant DEP-1) for targeted delivery for genetic therapy, involve methods well known in the art. For example, the desirable properties, lengths and other characteristics of such oligonucleotides are well known. In certain preferred embodiments such an antisense oligonucleotide comprises at least 15 consecutive nucleotides complementary to an isolated nucleic acid molecule encoding a substrate trapping mutant PTP as provided herein. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.*

26:2191–2194 (1985); Moody et al., *Nucleic Acids Res.* 12:4769–4782 (1989); Uznanski et al., *Nucleic Acids Res.* (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein In: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucleic Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

According to this embodiment of the invention, particularly useful antisense nucleotides and triplex molecules are molecules that are complementary to or bind the sense strand of DNA or mRNA that encodes a PTP polypeptide (including substrate trapping mutant DEP-1), such that inhibition of translation of mRNA encoding the DEP-1 polypeptide is effected.

A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such PTP (including substrate trapping mutant PTP) mRNA-specific ribozyme, or a nucleic acid encoding such a ribozyme, may be delivered to a host cell to effect inhibition of PTP gene expression. Ribozymes, and the like may therefore be delivered to the host cells by DNA encoding the ribozyme linked to a eukaryotic promoter, such as a eukaryotic viral promoter, such that upon introduction into the nucleus, the ribozyme will be directly transcribed.

A biological signaling pathway may be induced in subject or biological source cells by contacting such cells with an appropriate stimulus, which may vary depending upon the signaling pathway under investigation, whether known or unknown. For example, a signaling pathway that, when induced, results in protein tyrosine phosphorylation and/or protein tyrosine dephosphorylation may be stimulated in subject or biological source cells using any one or more of a variety of well known methods and compositions known in the art to stimulate protein tyrosine kinase and/or PTP (e.g., DEP-1) activity. These stimuli may include, without limitation, exposure of cells to cytokines, growth factors, hormones, peptides, small molecule mediators, cell stressors (e.g., ultraviolet light; temperature shifts; osmotic shock; ROS or a source thereof, such as hydrogen peroxide, superoxide, ozone, etc. or any agent that induces or promotes ROS production (see, e.g., Halliwell and Gutteridge, *Free Radicals in Biology and Medicine* (3$^{rd}$ Ed.) 1999 Oxford University Press, Oxford, UK); heavy metals; alcohol) or other agents that induce PTK-mediated protein tyrosine phosphorylation and/or PTP-mediated phosphoprotein tyrosine dephosphorylation. Such agents may include, for example, interleukins (e.g., IL-1, IL-3), interferons (e.g., IFN-γ), human growth hormone, insulin, epidermal growth factor (EGF), platelet derived growth factor (PDGF), granulocyte colony stimulating factor (G-CSF), granulocyte-megakaryocyte colony stimulating factor (GM-CSF), transforming growth factor (e.g., TGF-β1), tumor necrosis factor (e.g., TNF-α) and fibroblast growth factor (FGF; e.g., basic FGF (bFGF)), any agent or combination of agents capable of triggering T lymphocyte activation via the T cell receptor for antigen (TCR; TCR-inducing agents may include superantigens, specifically recognized antigens and/or MHC-derived peptides, MHC peptide tetramers (e.g., Altman et al., 1996 *Science* 274:94–96) TCR-specific antibodies or fragments or derivatives thereof), lectins (e.g., PHA, PWM, ConA, etc.), mitogens, G-protein coupled receptor agonists such as angiotensin-2, thrombin, thyrotropin, parathyroid hormone, lysophosphatidic acid (LPA), sphingosine-1-phosphate, serotonin, endothelin, acetylcholine, platelet activating factor (PAF) or bradykinin, as well as other agents with which those having ordinary skill in the art will be familiar (see, e.g., Rhee et al., Sci STKE. 2000 Oct. 10;2000(53):PE1 and references cited therein).

As noted above, regulated tyrosine phosphorylation contributes to specific pathways for biological signal transduction, including those associated with cell division, cell survival, apoptosis, proliferation and differentiation, and "inducible signaling pathways" in the context of the present invention include transient or stable associations or interactions among molecular components involved in the control of these and similar processes in cells. Depending on the particular pathway of interest, an appropriate parameter for determining induction of such pathway may be selected. For example, for signaling pathways associated with cell proliferation, there is available a variety of well known methodologies for quantifying proliferation, including, for example, incorporation of tritiated thymidine into cellular DNA, monitoring of detectable (e.g., fluorimetric or colorimetric) indicators of cellular respiratory activity, or cell counting, or the like. Similarly, in the cell biology arts there are known multiple techniques for assessing cell survival (e.g., vital dyes, metabolic indicators, etc.) and for determining apoptosis (e.g., annexin V binding, DNA fragmentation assays, caspase activation, etc.). Other signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, etc.), or altered cellular morphology, and the like, such that cellular responsiveness to a particular stimulus as provided herein can be readily identified to determine whether a particular cell comprises an inducible signaling pathway. For example, given the disclosure provided herein for the first time that DEP-1 associates with, and is capable of being isolated in a complex with, the Met cell surface receptor, certain cellular morphogenetic and motility properties associated with Met activity may provide evidence of biological signal transduction in a cell (e.g., Vadnais et al., 2002 *J. Biol. Chem.* [epub ahead of print], Manuscript M209481200, Oct. 7, 2002).

A "sample" as used herein refers to a biological sample containing at least one tyrosine phosphorylated protein, and may be provided by obtaining a blood sample, biopsy specimen, tissue explant, organ culture or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication or any other means for processing a sample derived from a subject or biological source. In certain preferred embodiments, the sample is a cell lysate, and in certain particularly preferred embodiments the lysate is a detergent solubilized cell lysate from which insoluble components have been removed according to standard cell biology techniques. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. Optionally, in certain situations it may be desirable to treat cells in a biological sample with pervanadate as described herein, to enrich the sample in tyrosine phosphorylated proteins. Other means may also be employed to effect an increase in the population of tyrosine phosphorylated proteins present in the sample, including the use of a subject or biological source that is a cell line that has been transfected with at least one gene encoding a protein tyrosine kinases. Additionally or alternatively, protein tyrosine phosphorylation may be stimulated in subject or biological source cells using any one or more of a variety of well known methods and compositions known in the art to stimulate protein tyrosine kinase activity. These stimuli may include, without limitation, exposure of cells to cytokines, growth factors, hormones, peptides, small molecule mediators or other agents that induce PTK-mediated protein tyrosine phosphorylation. Such agents may include, for example, interleukins, interferons, human growth hormone, insulin and fibroblast growth factor (FGF), as well as other agents with which those having ordinary skill in the art will be familiar.

According to the subject invention, a sample comprising at least one tyrosine phosphorylated protein or polypeptide is combined with at least one substrate trapping mutant PTP as provided herein, under conditions and for a time sufficient to permit formation of a complex between the tyrosine phosphorylated protein and the substrate trapping mutant PTP. Suitable conditions for formation of such complexes are known in the art and can be readily determined based on teachings provided herein, including solution conditions and methods for detecting the presence of a complex. Next, the presence or absence of a complex comprising the tyrosine phosphorylated protein and the substrate trapping mutant PTP is determined, wherein the presence of the complex indicates that the tyrosine phosphorylated protein is a substrate of the PTP with which it forms a complex.

Substrate trapping mutant PTPs that associate in complexes with tyrosine phosphorylated protein substrates may be identified by any of a variety of techniques known in the art for demonstrating an intermolecular interaction between a PTP and a PTP substrate as described above, for example, co-purification, co-precipitation, co-immunoprecipitation, radiometric or fluorimetric assays, western immunoblot analyses, affinity capture including affinity techniques such as solid-phase ligand-counterligand sorbent techniques, affinity chromatography and surface affinity plasmon resonance, and the like (see, e.g., U.S. Pat. No. 5,352,660).

Determination of the presence of a PTP/substrate complex may employ antibodies, including monoclonal, polyclonal, chimeric and single-chain antibodies, and the like, that specifically bind to the PTP or the tyrosine phosphorylated protein substrate. Labeled PTPs and/or labeled tyrosine phosphorylated substrates can also be used to detect the presence of a complex. The PTP or phosphorylated protein can be labeled by covalently or non-covalently attaching a suitable reporter molecule or moiety, for example any of various enzymes, fluorescent materials, luminescent materials and radioactive materials. Examples of suitable enzymes include, but are not limited to, horseradish peroxidase, biotin, alkaline phosphatase, β-galactosidase and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride and phycoerythrin. Appropriate luminescent materials include luminol, and suitable radioactive materials include radioactive phosphorus [$^{32}$P], iodine [$^{125}$I or $^{131}$I] or tritium [$^{3}$H].

Using such approaches, representative complexes of PTP1B with p210 bcr:abl, of PTP-PEST with p130$^{cas}$, of TC-PTP with Shc (e.g., Tiganis et al., 1998 Mol. Cell. Biol. 18:1622–1634) and of PTPH1 with pp97/VCP may be readily identified by western immunoblot analysis as described below. These associations may be observed, for example, in lysates from several cell lines and in transfected cells, indicating that p210bcr:abl, p130$^{cas}$, Shc and VCP represent major physiologically relevant substrates for PTP1B, PTP-PEST, TC-PTP and PTPH1, respectively. The compositions and methods of the present invention, which may be used, as exemplified herein, to identify specific tyrosine phosphorylated substrates for PTP1B, PTP-PEST and PTPH1, are generally applicable to any member of the PTP family, including but not limited to TC-PTP, PTPγ, MKP-1, DEP-1, PTPμ, SHP2, PTP-PEZ, PTP-MEG1, LC-PTP, CD45, LAR and PTPX10.

In certain embodiments of this aspect of the invention, the sample may comprise a cell that naturally expresses the tyrosine phosphorylated protein that is a PTP substrate, while in certain other embodiments the sample may comprise a cell that has been transfected with one or more nucleic acid molecules encoding the substrate protein. For example, the sample may comprise a cell or population of cells that has been transfected with a nucleic acid library such as a cDNA library that contains at least one nucleic acid molecule encoding a substrate protein. Any tyrosine phosphorylated protein is suitable as a potential substrate in the present invention. Tyrosine phosphorylated proteins are well known in the art. Specific examples of appropriate substrates include, without limitation, p130$^{cas}$, pp 97/VCP, the EGF receptor, p210 bcr:abl, MAP kinase, Shc and the insulin receptor. Of particular interest are tyrosine phosphorylated proteins that have been implicated in a mammalian disease or disorder.

According to the present invention, substrates may include full length tyrosine phosphorylated proteins and polypeptides as well as fragments (e.g., portions), derivatives or analogs thereof that can be phosphorylated at a tyrosine residue. Such fragments, derivatives and analogs include any PTP substrate polypeptide that retains at least the biological function of interacting with a PTP as provided herein, for example by forming a complex with a PTP. A fragment, derivative or analog of a PTP substrate polypeptide, including substrates that are fusion proteins, may be (i) one in which one or more of the amino acid residues are substituted with a conserved or non-conserved amino acid residue (preferably a conserved amino acid residue), and such substituted amino acid residue may or may not be one encoded by the genetic code, or (ii) one in which one or more of the amino acid residues includes a substituent group, or (iii) one in which the substrate polypeptide is fused with another compound, such as a compound to increase the half-life of the polypeptide (e.g., polyethylene glycol) or a detectable moiety such as a reporter molecule, or (iv) one in which additional amino acids are fused to the substrate polypeptide, including amino acids that are employed for purification of the substrate polypeptide or a proprotein sequence. Such fragments, derivatives and analogs are deemed to be within the scope of those skilled in the art.

The subject invention also contemplates certain embodiments wherein the substrate trapping mutant PTP (that is combined with the sample) is a mutant PTP that is expressed by a cell, including embodiments wherein the cell has been transfected with one or more nucleic acid molecules encoding the mutant PTP. Thus, the method of identifying a tyrosine phosphorylated protein which is a substrate of a PTP may include in certain embodiments combining a sample comprising a tyrosine phosphorylated protein with a mutant PTP wherein the sample comprises a cell expressing either or both of the tyrosine phosphorylated protein and the mutant PTP. Optionally, the cell may be transfected with nucleic acids encoding either or both of the tyrosine phosphorylated protein and the mutant PTP.

In another aspect, the invention provides methods of identifying an agent that alters the interaction between a PTP and a tyrosine phosphorylated protein that is a substrate of the PTP, through the use of screening assays that detect the ability of a candidate agent to alter (i.e., increase or decrease) such interaction. The interaction between the PTP and its substrate may be determined enzymatically, for example by detecting catalytic substrate dephosphorylation. Alternatively, the interaction between the PTP (including a substrate trapping mutant PTP) and its substrate may be determined as a binding interaction, and in preferred embodiments such interaction is manifested as detection of a complex formed by PTP-substrate binding, according to criteria described herein. Agents identified according to these methods may be agonists (e.g., agents that enhance or increase the activity of the wildtype PTP) or antagonists (e.g., agents that inhibit or decrease the activity of the wildtype PTP) of PTP activity. Agents may be identified from among naturally occurring or non-naturally occurring compounds, including synthetic small molecules as described below.

In certain embodiments, wherein the screening assay is directed to PTP catalytic activity, the tyrosine phosphorylated protein that is a substrate of the PTP can be identified as described above, which method features the use of a novel substrate trapping mutant PTP as disclosed herein. Accordingly, a PTP and a tyrosine phosphorylated substrate are combined in the absence and in the presence of a candidate agent, where the substrate has first been identified as described above using a substrate trapping mutant PTP. The PTP and the substrate are combined under conditions permissive for the detectable dephosphorylation of the substrate to occur.

Any suitable method may be used to detect phosphoprotein dephosphorylation; such methods are well known in the art and include, without limitation, detection of substrate catalysis by one or more of, e.g., radiometric, fluorimetric, densitometric, spectrophotometric, chromatographic, electrophoretic, colorimetric or biometric assays. The level of dephosphorylation of the substrate in the absence of the agent is compared to the level of dephosphorylation of the substrate in the presence of the agent, such that a difference in the level of substrate dephosphorylation (e.g., a statistically significant increase or decrease) indicates the agent alters the interaction between the protein tyrosine phosphatase and the substrate.

For instance, an enzymatic activity assay utilizing a wildtype PTP can be carried out in the absence and presence of a candidate agent. Enzymatic activity assays known in the art include, for example, PTP activity assays using a tyrosine phosphorylated $^{32}$P-labeled substrate as described in Flint et al. (1993 EMBO J. 12:1937–1946). A decrease in the PTP enzymatic activity in the presence of the candidate agent indicates that the agent inhibits the interaction between the PTP and its substrate. Conversely, an increase in PTP enzymatic activity in the presence of the agent indicates that the agent enhances the interaction between the PTP and its substrate.

In certain other embodiments, wherein the screening assay is directed to identifying an agent capable of altering a substrate trapping mutant PTP:substrate binding interaction, the substrate trapping mutant PTP (as described herein) and a tyrosine phosphorylated substrate are combined in the absence and in the presence of a candidate agent under conditions and for a time sufficient to permit formation of a complex between the tyrosine phosphorylated substrate protein and the substrate trapping mutant PTP, thereby producing a combination. The formation of a complex comprising the tyrosine phosphorylated substrate protein and the substrate trapping mutant protein tyrosine phosphatase in the combination is next determined (as also provided herein), wherein a difference between the level of complex formation (e.g., a statistically significant difference) in the absence and in the presence of the agent indicates that the agent alters (i.e., increases or decreases) the interaction between the protein tyrosine phosphatase and the substrate. Alternatively, a competitive binding assay can be carried out utilizing the substrate trapping mutant PTP in the absence and presence of a candidate agent. Competitive binding assays known in the art include, for example, U.S. Pat. No. 5,352,660, which describes methods suitable for use according to these embodiments of the present invention. A decrease in the extent of PTP-substrate binding in the presence of the agent to be tested indicates that the agent inhibits the interaction between the PTP and its substrate. Conversely, an increase in the extent of binding in the presence of the agent to be tested indicates that the agent enhances the interaction between the PTP and its substrate.

Candidate agents for use in a method of screening for an agent that alters the interaction between a PTP and its tyrosine phosphorylated protein substrate according to the present invention (e.g., an inhibitor of PTP1B binding to a PTP1B substrate) may be provided as "libraries" or collections of compounds, compositions or molecules. Candidate agents that may interact with one or more PTPs (including agents that interact with a substrate trapping mutant PTP as provided herein) may include members of phosphotyrosyl peptide libraries as described in Songyang et al. (1995 Nature 373:536–539; 1993 Cell 72:767–778) that bind to the PTP. Peptides identified from such peptide libraries can then be assessed to determine whether tyrosine phosphorylated proteins containing these peptides exist in nature. Alternatively, libraries of candidate molecules to be screened may typically include compounds known in the art as "small molecules" and having molecular weights less than $10^5$ daltons, preferably less than $10^4$ daltons and still more preferably less than 10³ daltons. For example, members of a library of test compounds can be administered to a plurality of samples, each containing at least one substrate trapping mutant PTP and at least one tyrosine phosphorylated protein that is a substrate of the PTP as provided herein, and then assayed for their ability to enhance or inhibit mutant PTP binding to the substrate. Compounds so identified as capable of altering PTP-substrate interaction (e.g., binding and/or substrate phosphotyrosine dephosphorylation) are valuable for therapeutic and/or diagnostic purposes, since they permit treatment and/or detection of diseases associated with PTP activity. Such compounds are also valuable in research directed to molecular signaling mechanisms that involve PTPs, and to refinements in the discovery and development of future compounds exhibiting greater specificity.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694, PCT/US91/04666, which are hereby incorporated by reference in their entireties) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures, and tested using substrate trapping mutant PTPs according to the present disclosure.

Similarly, the invention relates to a method of reducing the formation of inducible or induced signaling complexes associated with PTP-mediated pathways, and in preferred embodiments DEP-1-mediated biological signaling pathways as known to the art and as disclosed herein. DEP-1 overexpression in a cell comprising an inducible biological signaling pathway, which cell has been contacted with a stimulus that induces the pathway to generate an increased level of a molecular complex comprising DEP-1 and a DEP-1 substrate polypeptide as provided herein, may also be used to alter (i.e., increase or decrease) a DEP-1-mediated biological signal with therapeutic benefit.

The methods of the present invention are specifically exemplified herein with respect to the DEP-1 polypeptide comprising the amino acid sequence set forth in SEQ ID NO:2 and may also in certain preferred embodiments relate to the DEP-1 polypeptide comprising the amino acid sequence set forth in SEQ ID NO:3; however, it is understood that the invention is not limited to these specific DEP-1 polypeptides but may be applicable to certain other DEP-1 polypeptides as provided herein. In certain embodiments, the invention relates in part to DEP-1(D1205A), in which the aspartate residue at position 1205 of wildtype DEP-1 (SEQ ID NO:2) is replaced with alanine, and in which further a PTP tyrosine residue may optionally be replaced with a non-phosphorylatable residue.

As disclosed herein and described in the Examples, the substrate specificities of DEP-1 polypeptide comprising the amino acid sequence set forth in SEQ ID NO:2 may be characterized by methods that relate to PTP catalytic and/or binding interactions with substrate, e.g., dephosphorylation and substrate trapping in vitro and in vivo. DEP-1 (see, e.g., U.S. Pat. No. 6,114,140; WO 95/30008) is well known in the art. The substrate trapping methods provided herein are generally applicable to any DEP-1 polypeptide by virtue of the invariant PTP catalytic domain aspartate residue and the frequency of tyrosine in PTP amino acid sequences, and should therefore prove useful in delineating the substrate preferences of other PTP family members. In particular, the use of mutant, catalytically impaired PTPs to trap, and thereby isolate, potential substrates permits the identification of physiologically important substrates for individual PTPs, leading to improved understanding of the roles of these enzymes in regulation of cellular processes. Furthermore, replacement of PTP tyrosine residues with amino acids that cannot be phosphorylated provides substrate trapping mutant PTPs that are not impaired in their ability to interact with tyrosine phosphorylated protein substrates.

The present invention also pertains to pharmaceutical compositions comprising an agent that is capable of altering the specific association of a DEP-1 polypeptide with a DEP-1 substrate polypeptide. For administration to a patient, one or more such agents are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intraocular, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

For pharmaceutical compositions comprising an agent that is a nucleic acid molecule encoding a DEP-1 polypeptide or a DEP-1 substrate polypeptide that is capable of altering the specific association of a DEP-1 polypeptide with a DEP-1 substrate polypeptide (such that the polypeptide is generated in situ), the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692,1993. The uptake of naked DNA may be increased by coating the DNA onto biodegradable beads, which are efficiently transported into the cells.

Within a pharmaceutical composition, a DEP-1 or a DEP-1 substrate polypeptide, a DEP-1- or a DEP-1 substrate-encoding nucleic acid molecule or an agent that is capable of altering the specific association of a DEP-1 polypeptide with a DEP-1 substrate polypeptide may be linked to any of a variety of compounds. For example, such a polypeptide, nucleic acid molecule or agent may be linked to a targeting moiety (e.g., a monoclonal or polyclonal antibody, a protein or a liposome) that facilitates the delivery of the agent to the target site. As used herein, a "targeting moiety" may be any substance (such as a compound or cell) which, when linked to an agent, enhances the transport of the agent to a target cell or tissue, thereby increasing the local concentration of the agent. Targeting moieties include antibodies or fragments thereof, receptors, ligands and other molecules that bind to cells of, or in the vicinity of the target tissue. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) at which the agent is expected to exert a therapeutic benefit.

Pharmaceutical compositions may be administered in a manner appropriate to the disease to be treated (or prevented), for example, a condition, disorder or disease associated with cell growth, differentiation or survival, such as cancer or any other malignant condition, autoimmune disease, inflammatory disease or any other condition wherein a beneficial response may be elicited by specific manipulation of a DEP-1 signal transduction pathway. An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival). For prophylactic use, a dose should be sufficient to prevent, delay the onset of or diminish the severity of a disease associated with a defect in cell signaling, for example a defect leading to abnormal cell cycle regulation, proliferation, activation, differentiation, senescence, apoptosis, adhesion, metabolic activity, gene expression or the like.

Optimal dosages may generally be determined using experimental models and/or clinical trials. In general, the amount of polypeptide present in a dose, or produced in situ by DNA present in a dose, ranges from about 0.01 µg to about 100 µg per kg of host, typically from about 0.1 µg to about 10 µg. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art. Suitable dose sizes will vary with the size of the patient, but will typically range from about 1 mL to about 500 mL for a 10–60 kg subject.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The following Examples are offered by way of illustration and not by way of limitation.

EXAMPLES

Example 1

Experimental Procedures

Generation of DEP-1 cDNA constructs—Full-length human DEP-1 cDNA was isolated and subcloned into the mammalian expression vector pMT2 (Ostman et al., *Proc. Natl. Acad. Sci. USA* 91:9680–84 (1994)). The nucleotide and amino acid numbers listed below correspond to the human DEP-1 sequence reported previously (Ostman et al., supra) GenBank Accession Number U10886. DEP-1 point mutants (C1239S, D1205A) were generated by overlap extension using pMT2.DEP-1 as template. The resulting mutant PCR products were exchanged with wild type sequence in pMT2.DEP-1 and sequenced to confirm the mutations. As used herein, a polynucleotide encoding a DEP-1(DA) mutant describes a DEP-1 mutant that has the aspartate residue at position 1205 of SEQ ID NO:2 substituted with an alanine residue, and a polynucleotide encoding a DEP-1(CS) mutant describes a DEP-1 mutant that has the cysteine residue at position 1239 of SEQ ID NO:2 substituted with a serine residue.

DEP-1 cytoplasmic domain constructs were generated using the pMT2.DEP-1 wild type or point mutant (C1239S, D1205A) constructs as template. A 5' primer introduced a BamHI site before the DEP-1 cytoplasmic sequence at nucleotide 3338, whereas a 3' primer added a SalI site after the DEP-1 stop codon. The resulting PCR products (DEP-1 nucleotides 3338–4362) were cloned into the BamHI/SalI sites of the pMAL-c2E vector from New England Biolabs (Beverly, Mass.) generating wild type and point mutant (C1239S, D1205A) pMAL.DEP-1 constructs. The fusion proteins were expressed in *Escherichia coli* and purified on amylose resin according to the manufacturer's instructions. The resulting proteins (~84 kDa) have maltose binding protein (MBP) fused to the N-terminus of the DEP-1 cytoplasmic domain (amino acids 997–1337).

Met chimeric construct—The chimeric receptor CSF-MET comprising the extracellular domain of human CSF-1R and the transmembrane and cytoplasmic domains of human Met was described by Zhu et al., (1994) supra. Briefly, the human extracellular domain of the CSF-MET fusion protein corresponded to amino acids at positions 1–507 of CSF-1R (see, e.g., GenBank Acc. No. NP_005205; Acc. No. 1204266A; and Acc. No. P07333). The histidine at position 508 in CSF (see Acc. No. NP_005202) was mutated to an aspartic acid residue to generate a restriction site for cloning purposes (see Zhu et al., (1994) supra, FIG. 1). To this aspartate was fused the MET transmembrane and cytoplasmic domains (amino acids at positions 938–1408 of MET proto-oncogene, Zhu et al., (1994) supra; see GenBank Acc. No. NP_000236; Acc. No. AAA59591).

Cell culture and transfections—MDA-MB-231 (ATTC HTB-26) and T-47D (ATCC HTB-133) human breast tumor cells (American Type Culture Collection, Manassas, Va.) were cultured in DMEM containing 5% fetal bovine serum, 100 units/ml penicillin and 100 µg/ml streptomycin and 1% non-essential amino acids. The T-47D/Met cell line (Shen et al., *Cell* 103:501–10 (2000)) was cultured in DMEM as above further supplemented with 200 µg/ml G418. Human embryonal kidney 293 cells (ATTC CRL-1573) were cultured in DMEM containing 10% bovine calf serum, 100 units/ml penicillin and 100 µg/ml streptomycin.

Transfection of 293 cells was performed using the calcium phosphate-mediated transfection protocol. For trapping experiments, 293 cells were transfected with 20 µg CSF-MET DNA (pXM.CSF-MET) and 20 µg of empty vector DNA (pMT2) or 20 µg DEP-1 DNA (pMT2.DEP-1, pMT2.DEP-1(CS), pMT2.DEP-1(DA)) per 10 cm dish. To examine dephosphorylation in 293 cells, 20 µg CSF-MET DNA (pXM.CSF-MET) were co-transfected with increasing amounts of DEP-1 DNA (pMT2.DEP-1) (0, 1, 2, 5, 10 µg) or 10 µg DEP-1(CS) DNA (pMT2.DEP-1(CS)) per 10 cm dish of cells. The total amount of DNA in each transfection was normalized using empty vector DNA (pMT2).

Antibodies—DEP-1 monoclonal antibodies A3 and 143-41 used for immunoprecipitations were generous gifts from Dr. Gregorio Aversa and Dr. Antoni Gaya, respectively (Palou et al., supra; Tangye et al., supra). The DEP-1 polyclonal antibody CS895A was generated against the DEP-1 extracellular domain peptide (CDASNTERSRAG-SPTAP, SEQ ID NO: 19) corresponding to amino acids 292–307 coupled to KLH (Pierce, Rockford, Ill.). The Met polyclonal antibody 144 used for immunoprecipitations was generated against a carboxy-terminal peptide (Rodrigues et al., *Mol. Cell Biol.* 11:2962–70). The anti-phosphotyrosine monoclonal antibodies G98 and G104 were generated as described (Garton et al., *Mol. Cell Biol.* 16:6408–18 (1996)). Anti-phosphotyrosine-agarose (PT-66) was purchased from Sigma (St. Louis, Mo.) and anti-phosphotyrosine (4G10) agarose conjugate was purchased from Upstate Biotechnology (Lake Placid, N.Y.). The Met antibody C-12 was purchased from Santa Cruz Biotechnology (Santa Cruz, Calif.). Antibodies for p120$^{ctn}$, E-cadherin, Grb2, and phosphotyrosine (PY20) were purchased from BD Transduction Labs (Lexington Ky.). Antibodies specific for β-catenin (6F9) and plakoglobin (15F11) were purchased from Sigma (St. Louis, Mo.), and the Gab 1 C-terminal antibody was purchased from Upstate Biotechnology (Lake Placid, N.Y.). Anti-c-Met (pYpYpY$^{1230/1234/1235}$) and (pY$^{1365}$) antibodies were purchased from BioSource International (Camarillo, Calif.), and Phospho-Met (Tyr$^{1349}$) antibody was purchased from Cell Signaling Technology (Beverly, Mass.).

Substrate trapping—Prior to lysis, T-47D and T-47D/Met cells were treated with 50 µM pervanadate for 20 minutes, whereas MDA-MB-231 cells were treated with 100 µM pervanadate for 20 minutes. Cells were rinsed with PBS and lysed in 1% NP-40 buffer (1% NP-40,150 mM NaCl, 20 mM HEPES pH7.5, 1 mM EDTA, 5 µg/ml aprotinin, 5 µg/ml leupeptin, 1 mM benzamidine). For trapping experiments in vitro, the lysis buffer also contained 5 mM iodoacetic acid to inhibit cellular PTPs irreversibly. After incubation on ice for 5 minutes, dithiothreitol was added to a final concentration of 10 mM to inactivate any unreacted iodoacetic acid. Insoluble material was removed by centrifugation. T-47D lysate (1 mg) or MDA-MB-231 lysate (5 mg) was mixed with MBP or the MBP-DEP-1 constructs bound to amylose resin at a ratio of 1 µg fusion to 500 µg lysate. Lysates and fusion proteins were incubated at 4° C. for 2 hours and washed extensively with 1% NP-40 buffer. Tyrosine phosphorylated proteins were immunoprecipitated using 0.1 mg T-47D cell lysate and a combination of 5 µl each of anti-phosphotyrosine antibodies PT-66 and 4G10. Lysate and antibodies were incubated at 4° C. for 2 hours and washed extensively with 1% NP-40 buffer. Protein complexes were released by incubation in reducing Laemmli SDS-PAGE sample buffer at 95° C., subjected to SDS-PAGE on 8% gels, and transferred onto Immobilon-P membranes (Millipore, Bedford, Mass.) for immunoblotting.

In order to determine whether the tyrosine phosphorylated proteins bound to the substrate-trapping mutants at the PTP active site, the effects of vanadate on complex formation were tested. MBP fusion proteins bound to amylose were pre-incubated in 1% NP-40 buffer (without EDTA) with or without 2 mM vanadate. Cells were rinsed with PBS and lysed in 1% NP-40 buffer (without EDTA) with or without 2 mM vanadate. For vanadate competition experiments, the lysis buffer also contained 5 mM iodoacetic acid. After 5 minutes on ice, dithiothreitol was added to a final concentration of 10 mM. Insoluble material was removed by centrifugation, and samples were processed as described above.

Proteins bound to the DEP-1 substrate-trapping mutant were analyzed by immunoblotting. T-47D and T-47D/Met cells were treated and lysed as above. Lysates (30 mg) were mixed with MBP.DEP-1 or MBP-DEP-1(DA) bound to amylose resin at a ratio of 1 μg fusion protein to 500 μg lysate. Lysates and fusion proteins were incubated at 4° C. for 2 hours and then washed extensively with 1% NP-40 buffer. Protein complexes were released by incubation in reducing Laemmli SDS-PAGE sample buffer at 95° C., subjected to SDS-PAGE on 8% gels, and transferred onto Immobilon-P membranes for immunoblotting. The samples were divided into 5 mg lysate equivalents per fusion per lane.

Immunoprecipitations—Transfected cells were rinsed with PBS and lysed in 1% NP-40 buffer (1% NP-40, 150 mM NaCl, 20 mM HEPES pH7.5, 1 mM EDTA, 5 μg/ml aprotinin, 5 μg/ml leupeptin, 1 mM benzamidine, 50 mM NaF, 5 mM iodoacetic acid) and processed as above. For substrate-trapping experiments, DEP-1 was immunoprecipitated from 1 mg lysate with the DEP-1 antibodies, A3 and 143-41, and Met was immunoprecipitated from 1 mg of cell lysate using the Met antibody 144.

For dephosphorylation and recruitment experiments, transfected cells were rinsed with PBS and lysed in 1% NP-40 buffer (1% NP-40,150 mM NaCl, 20 mM HEPES pH 7.5, 1 mM EDTA, 5 μg/ml aprotinin, 5 μg/ml leupeptin, 1 mM benzamidine, 50 mM NaF, 5 mM iodoacetic acid, 1 mM vanadate) and processed as above. Met was immunoprecipitated from 1 mg lysate using the Met antibody 144. Lysate and antibody were incubated at 4° C. for 1 hour. Protein A Sepharose 4 Fast Flow (Amersham Pharmacia Biotech, Uppsala, Sweden) was added for 45 minutes at 4° C. Immune complexes were washed extensively with 1% NP-40 buffer, released by incubation in reducing Laemmli SDS-PAGE sample buffer at 95° C., subjected to SDS-PAGE on 8% gels, and transferred onto Immobilon-P membranes for immunoblotting.

Example 2

Figure 1B:
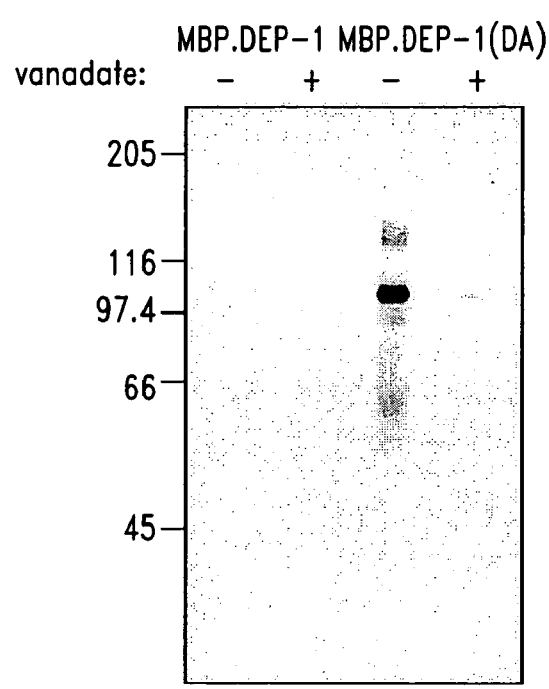

Interaction of a DEP-1(DA) Substrate-Trapping Mutant with a Subset of Tyrosine Phosphorylated Proteins from Two Human Breast Tumor Lines Two human breast tumor lines (T-47D and MDA-MB-23 1), which express DEP-1, were used for in vitro studies to identify potential physiological substrates of the PTP. The cells were treated with pervanadate to generate the broadest spectrum of potential phosphotyrosine containing substrates for analysis. DEP-1 fusion proteins comprising the maltose binding protein (MBP) fused to the N-terminus of the DEP-1 cytoplasmic domain (amino acids 997–1337) were generated. Wild type DEP-1 (MBP.DEP-1), catalytically inactive (MBP.DEP-1(CS)) and substrate-trapping (MBP.DEP-1 (DA)) mutant forms of DEP-1 were used for purification of potential substrates by affinity chromatography. T-47D cells were treated with 50 μM pervanadate for 20 minutes prior to cell lysis. DEP-1 fusion proteins were incubated with lysate of pervanadate treated T-47D cells. Tyrosine phosphorylated proteins that interacted with the fusion proteins were visualized by immunoblotting with anti-phosphotyrosine antibodies. The results are presented in FIG. 1A. Only the substrate-trapping mutant form of DEP-1 (MBP-DEP-1 (DA)) bound tyrosine phosphorylated proteins. In addition, when a comparison was made between the tyrosine phosphorylated proteins that bound to the DEP-1 substrate-trapping mutant and the proteins immunoprecipitated with anti-phosphotyrosine antibodies, MBP-DEP-1(DA) recognized only a small subset of the tyrosine phosphorylated proteins from the lysate of pervanadate treated T-47D cells (FIG. 1A).

To determine whether the proteins that interacted with MBP-DEP-1(DA) were potential substrates, the fusion proteins were pre-incubated with vanadate. Vanadate is a competitive inhibitor that blocks the PTP active site and prevents substrate binding and phosphatase activity (Huyer et al., *J. Biol. Chem.* 272:843–51 (1997)). Cells were lysed in lysis buffer (see Material and Methods) with (+) or without (−) 2 mM vanadate. MBP and MBP.DEP-1 fusion proteins were pre-incubated with (+) or without (−) 2 mM vanadate and added to cell lysates. Protein complexes were analyzed by SDS-PAGE and immunoblotting using anti-phosphotyrosine antibodies (see Example 1). The immunoblot results are presented in FIG. 1B. The interaction between the tyrosine phosphorylated proteins and MBP-DEP-1(DA) was inhibited by vanadate, suggesting that they bound to the active site and may represent substrates of DEP-1.

Similarly, DEP-1 fusion proteins were incubated with the lysate of pervanadate treated MDA-MB-231 cells. MDA-MB-231 cells were treated with 100 μM pervanadate for 20 minutes prior to lysis. MBP or MBP.DEP-1 fusion proteins (MBP.DEP-1, MBP.DEP-1 (CS), MBP.DEP-1 (DA)) were incubated with cell lysates, and protein complexes were analyzed by SDS-PAGE and immunoblotting using anti-phosphotyrosine antibodies. As was observed with the T-47D cell lysates, only the substrate-trapping mutant form of DEP-1 (MBP-DEP-1(DA)) interacted with tyrosine phosphorylated proteins from MDA-MB-231 cell lysates (FIG. 2A). Only a small subset of the pool of available tyrosine phosphorylated proteins was recognized by the PTP. MDA-MB-231 cells were treated with 100 μM pervanadate for 20 minutes and then lysed in lysis buffer (see Example 1) with or without 2 mM vanadate. MBP and MBP.DEP-1 fusion proteins were pre-incubated with or without 2 mM vanadate and then added to the cell lysates. The protein complexes that formed were analyzed by SDS-PAGE and immunoblotting using anti-tyrosine antibodies (see Example 1). The immunoblot presented in FIG. 2B illustrates that the interaction of the substrate-trapping mutant form of DEP-1 (MBP-DEP-1(DA)) with tyrosine phosphorylated proteins (FIG. 1B) was also inhibited by vanadate. Pervanadate treatment resulted in the accumulation of tyrosine phosphorylated proteins in both T-47D and MDA-MB-231 cell lines.

Example 3

Identification of Proteins that Interacted with the DEP-1 Substrate-Trapping Mutant Although the tyrosine-phosphorylated proteins that interacted with MBP.DEP-1(DA) were easily detected by immunoblotting with anti-phosphotyrosine antibodies, these proteins were difficult to detect on Coomassie stained gels, suggesting that they were not abundant proteins. From a large-scale preparation of DEP-1 substrates from T-47D cells, cell lysates were prepared and subjected to affinity chromatography using the substrate-trapping mutant form of DEP-1 coupled to the affinity matrix. The bound fraction was separated by SDS-PAGE. On Coomassie stained gels, a 100 kDa protein was detected that corresponded to a 100 kDa tyrosine phosphorylated protein that was detected by immunoblotting (see FIG. 1A, arrow). The protein band of apparent Mr 100 kDa was excised from the SDS-PAGE gel.

Peptides derived from this protein were sequenced by mass spectrometry according to methods known in the art. Two individual peptides (NLSYQVHR, SEQ ID NO: 20; SQSSHSYDDSTLPLIDR, SEQ ID NO: 21) matched sequences in the src substrate and adherens junction component, p120$^{ctn}$ (Table 1). Both sequences can be found in all the p120$^{ctn}$ isoforms identified to date (see Keirsebilck et al., Genomics 50:129–46 (1998)). The table presents the peptide sequences and their positions within the various isoforms of p120$^{ctn}$.

TABLE 1

Identification of p120$^{ctn}$ as a substrate of DEP-1

| p120$^{ctn}$ isoform | Peptide sequence and positions of matching amino acids in p120$^{ctn}$ isoforms | | GenBank Accession Number |
| --- | --- | --- | --- |
| | NLSYQVHR (SEQ ID NO: 20) | SQSSHSYDDSTLPLIDR (SEQ ID NO: 21) | |
| 1ABC | 585–592 | 859–875 | AF062321, AF062317 |
| 2ABC | 531–538 | 805–821 | AF062319 |
| 3AB | 484–491 | 752–768 | AF062338 |
| 4ABC | 262–269 | 536–552 | AF062342 |

Figure 3:
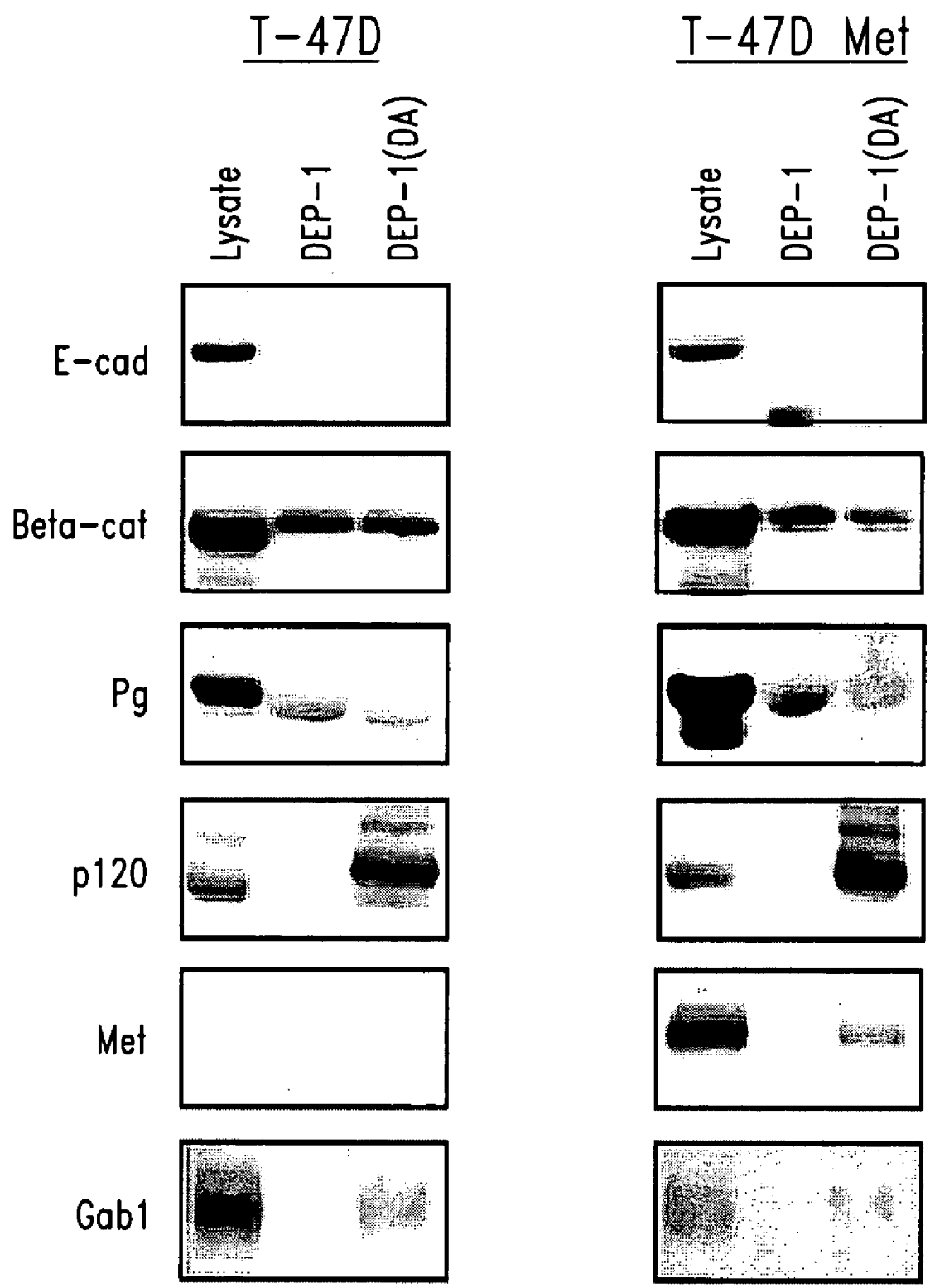
FIG. 3 shows immunoblots that identify tyrosine phosphorylated proteins that interacted with the DEP-1(DA) substrate-trapping mutant. T-47D and T-47 cells ectopically expressing Met (T-47D Met) were treated with 50 μM pervanadate for 20 minutes prior to lysis. MBP.DEP-1 or MBP.DEP-1(DA) fusion proteins were incubated with cell lysates, and protein complexes were analyzed by SDS-PAGE and immunoblotting using antibodies directed towards E-cadherin (E-cad); β-catenin (Beta-cat); plakoglobin (Pg); p120$^{ctn}$ (p120); Met (Met); and Gab 1 (Gab 1). Cell lysate (50 μg) was loaded to confirm the expression and molecular weight of each of the proteins analyzed by immunoblotting (Lysate).

Interaction of DEP-1 with other functional components was investigated. T-47D and T-47D/MET cells were cultured as described in Example 1 and were then treated with 50 µM pervanadate for 20 minutes prior to lysis. MBP-.DEP-1 or MBP.DEP-1(DA) fusion proteins were incubated with cell lysates. Protein complexes were analyzed by SDS-PAGE and immunoblotting using antibodies directed towards E-cadherin (E-cad), β-catenin (Beta-cat), plakoglobin (Pg), p120$^{ctn}$ (p120), Met (Met) and Gab 1 (Gab 1) (see Example 1). Total cell lysate was analyzed to confirm the expression and molecular weight of each of the proteins identified by immunoblotting. As shown in FIG. 2, immunoblot analysis revealed that the DEP-1 substrate-trapping mutant (DA) did not interact with the transmembrane protein E-cadherin from pervanadate treated T-47D cell lysates. The cytoplasmic proteins β-catenin and plakoglobin, however, were found in a complex with MBP.DEP-1(DA). Although p120$^{ctn}$ only interacted with the DEP-1 substrate-trapping mutant, β-catenin and plakoglobin also interacted with the wild type form of the enzyme (MBP-DEP-1) (FIG. 3).

As discussed above, the DEP-1 substrate-trapping mutant bound several tyrosine-phosphorylated proteins from both T-47D and MDA-MB-231 cell lines (see FIG. 1, FIG. 2). On the basis of the molecular weights of these proteins and the observation that DEP-1 interacted with components of adherens junctions, experiments were conducted to probe for signaling molecules known to localize to cell-cell junctions. MBP.DEP-1(DA) trapped Met, the HGF/SF receptor, from pervanadate-treated MDA-MB-231 cells (data not shown). Since Met is expressed at low levels in T-47D cells, a T-47D stable cell line ectopically expressing the PTK (T-47D/Met) was employed, which has been used previously in analysis of Met function (Shen et al., supra). MBP-DEP-1(DA) also trapped Met from pervanadate treated T-47D/Met cell lysate, and this interaction was not observed between the wild type DEP-1 (MBP-DEP-1) and Met (FIG. 3). This suggested a transient interaction between DEP-1 and Met, which is consistent with that of enzyme and substrate.

MBP-DEP-1(DA) trapped the docking protein Gab 1 from T-47D/Met cell lysates (FIG. 3), which is consistent with earlier reports of pleiotropic effects mediated by Met through recruitment of a number of docking and signaling molecules (reviewed in Furge et al., supra). Following activation of Met, Gab 1 was reported to be recruited to the kinase and phosphorylated on tyrosine residues, permitting recruitment of other signaling and adapter molecules, thereby amplifying downstream signals. As shown in FIG. 3, MBP.DEP-1(DA) also trapped Gab 1 from T-47D cells suggesting that the Gab 1-DEP-1 interaction is at least partially direct in a manner that does not require Met.

Example 4

Figure 4A:
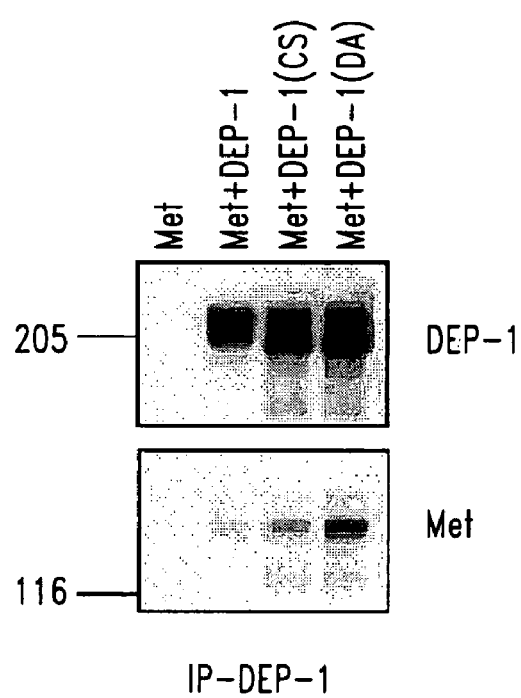
FIGS. 4A and 4B present immunoblots illustrating co-expression of DEP-1 and Met in 293 cells. 293 cells were transfected with CSF-MET alone (Met) or in combination with wild type (Met+DEP-1) or mutant forms of DEP-1 (Met+DEP-1(CS) or Met+DEP-1(DA).

Interaction Between Full Length DEP-1(DA) Substrate-Trapping Mutant and MET (HGF-R/SF-R) from 293 Cells As noted above, full length DEP-1 is a transmembrane PTP. As shown in the preceding Examples, however, by using only the cytoplasmic domain of the substrate-trapping mutant DEP-1, an interaction of DEP-1 with Met was observed. To determine whether the trapping mutant form of full length DEP-1 also trapped Met, each of full length DEP-1 and the mutants DEP-1 (CS) and DEP-1(DA) was co-expressed with a chimeric Met construct CSF-MET. This chimeric receptor, which comprised the extracellular domain of human colony stimulating factor 1 receptor (CSF-1R) and the transmembrane and cytoplasmic domains of human Met (Zhu et al., supra), was constitutively active when expressed in 293 cells, bypassing the requirement for ligand stimulation. 293 cells were tranfected with CSF-MET alone or in combination with wild type or mutant forms of DEP-1. Cells were serum-starved and then cell lysates were prepared as described in Example 1. The wild type DEP-1 and the DEP-1 mutants were immunoprecipitated from half of the cell lysates using monoclonal antibodies, A3 and 143-41 under conditions that preserved protein complexes. The immunoprecipitates were then separated by SDS-PAGE and transferred to Immobilon P membranes for immunoblotting. The levels of wild type DEP-1 and the DEP-1 (DA) and DEP-1 (CS) were deterinined by probing the immunoblots with the polyclonal antibody CS895A. The immunoblots were then stripped and reprobed for Met. The results are presented in FIG. 4A. Similar levels of DEP-1, DEP-1 (CS), and DEP-1(DA) were immunoprecipitated from 293 cell lysates (FIG. 4A). No endogenous DEP-1 could be detected in immunoprecipitates from 293 cells expressing the Met chimera alone. As with the DEP-1(DA) cytoplasmic domain fusion protein, full length DEP-1(DA) formed a stable complex with Met (FIG. 4A). The full length DEP-1(CS) mutant also bound Met, but less efficiently than the DEP-1(DA) mutant. Similar results were observed in the interaction between PTP-PEST and its substrate p130$^{cas}$ (Garton et al., supra). No stable interaction was observed between wild type DEP-1 and Met when co-expressed in 293 cells (FIG. 4A, second lane).

Figure 4B:
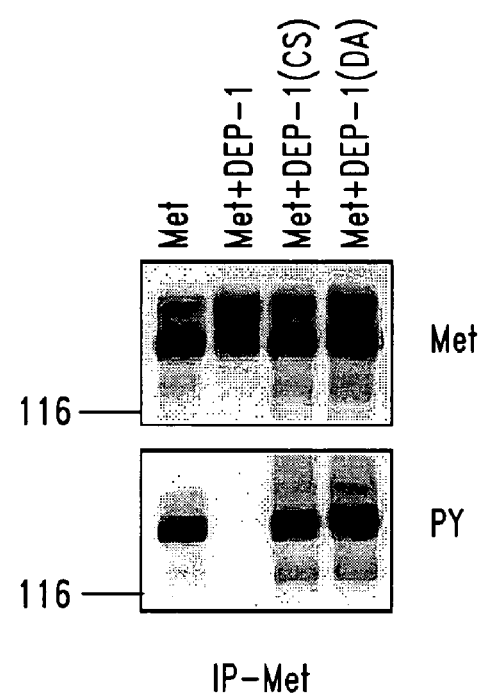

Full-length wild type DEP-1 was also observed to dephosphorylate Met in 293 cells. Because full-length substrate-trapping mutant forms of DEP-1 bound Met when co-expressed in 293 cells (FIG. 4A), whether full-length wild type DEP-1 could dephosphorylate Met was investigated. Full-length DEP-1 and the mutants DEP-1 (CS) and DEP-1(DA) were co-expressed with the CSF-MET chimera in 293 cells as described above. The Met chimera was immunoprecipitated from cell lysates with an antibody specific for the Met portion of the chimera. As shown in FIG. 4B, immunoblots revealed that similar levels of CSF-MET were immunoprecipitated in each condition. The Met chimera was tyrosine phosphorylated when it was expressed alone in 293 cells; however, the presence of tyrosine phosphorylation was not detected when it was co-expressed with wild type DEP-1 (FIG. 4B, lane 2, lower immunoblot). Although the DEP-1(CS) and DEP-1 (DA) mutants interacted with the Met chimera (FIG. 4A), Met was not dephosphorylated in the cells expressing these mutants, suggesting that dephosphorylation required DEP-1 catalytic activity.

Example 5

Preferential Dephosphorylation of C-Terminal Phosphotyrosine Residues in MET by DEP-1

Figure 5A:
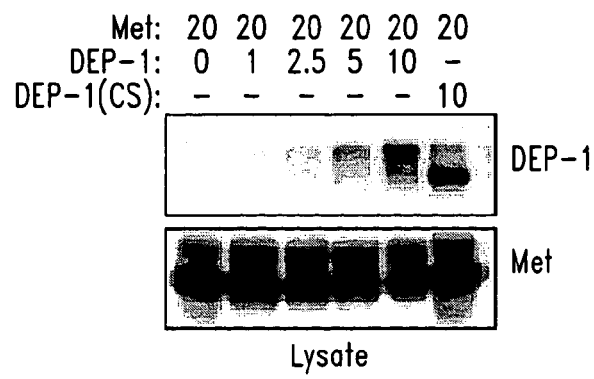
FIGS. 5A–5C present immunoblots demonstrating the effects of expression of DEP-1 on the phosphorylation of Met and on the association of Met with Grb2.

When equal amounts of wild type DEP-1 and CSF-MET plasmid DNA were transfected into 293 cells, the level of DEP-1 protein expressed was sufficient to dephosphorylate Met (FIG. 4B). A dose-response analysis was performed to determine whether varying the expression level of DEP-1 would affect its ability to dephosphorylate Met. 293 cells were transfected with a constant concentration of CSF-MET DNA (20 µg) and increasing amounts of wild type DEP-1 DNA (0, 1, 2.5, 5, 10 µg) or 10 µg of the catalytically inactive DEP-1(CS) mutant DNA (FIG. 5A). Immunoblots showed that as the levels of DEP-1 plasmid DNA used for transfection were increased, the level of DEP-1 protein that was expressed also increased, whereas the levels of Met protein detected were similar, independent of the level of DEP-1 expressed (FIG. 5A).

Figure 5B:
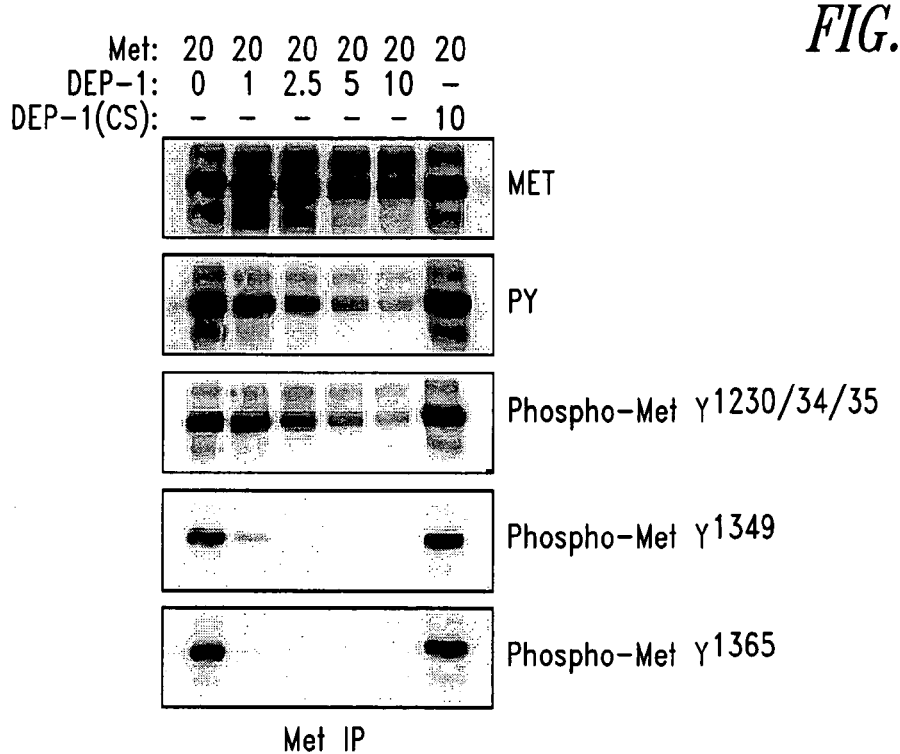

Dephosphorylation by DEP-1 of specific tyrosine residues of the Met polypeptide was examined. Met was immunoprecipitated from the lysates of serum-starved 293 cells prepared as described above using the polyclonal antibody 144. The immunoprecipitates were separated by SDS-PAGE in duplicate and transferred to membranes for immunoblotting as described in Example 1. An immunoblots was probed with the polyclonal antibody C-12 as shown in FIG. 5B, which revealed a constant level of Met immunoprecipitated from the cell lysates (MET). This blot was stripped and re-probed with the phospho-specific antibody to $Tyr^{1349}$ in Met (Phospho-Met $Y^{1349}$). A duplicate blot was probed with anti-phosphotyrosine antibodies to illustrate the total phosphotyrosine content (PY), then sequentially stripped and re-probed with phospho-specific antibodies to examine the phosphorylation status of $Tyr^{1230}$, $Tyr^{1234}$ and $Tyr^{1235}$ (Phospho-Met $Y^{1230/34/35}$), and $Tyr^{1365}$ (phospho-Met $Y^{1365}$). Although similar amounts of Met were immunoprecipitated from 293 cell lysates, a gradual decrease in the level of phosphorylation of Met was detected with increasing expression of wild type DEP-1 (FIG. 5B). The phosphorylation of Met when Met was expressed alone was similar with the phosphorylation of Met when expressed with the catalytically inactive form of DEP-1 (DEP-1(CS)).

Met contains three tyrosines in the activation loop of the catalytic domain ($Tyr^{1230}$, $Tyr^{1234}$ and $Tyr^{1235}$), and phosphorylation of $Tyr^{1234}$ and $Tyr^{1235}$ is required for full activation of the kinase (Rodrigues et al., *Oncogene* 9:2019–27 (1994)). To determine whether DEP-1 acted on these tyrosine residues, phospho-specific antibodies were employed. Met was immunoprecipitated from the lysates of serum-starved 293 cells (see above) using the polyclonal antibody 144. Duplicate samples of immunoprecipitates were separated by SDS-PAGE and immunoblotted. Immunoblots probed with the polyclonal antibody C-12 revealed a constant level of Met immunoprecipitated from the cell lysates (MET). This blot was stripped and re-probed with the phospho-specific antibody to $Tyr^{1349}$ in Met (Phospho-Met $Y^{1349}$). A duplicate blot was probed with anti-phosphotyrosine antibodies to illustrate the total phosphotyrosine content, then sequentially stripped and re-probed with phospho-specific antibodies to examine the phosphorylation status of $Tyr^{1230}$, $Tyr^{1234}$, and $Tyr^{1235}$ (Phospho-Met $Y^{1230/34/35}$), and $Tyr^{1365}$ (phospho-Met $Y^{1365}$). FIG. 5B shows that similar to the effects on the overall levels of Met phosphorylation, a gradual decrease in the level of phosphorylation of the activation loop tyrosine residues was observed with increasing expression of wild type DEP-1, and no effect on phosphorylation of Met was observed with the expression of DEP-1(CS). Phosphorylation of $Tyr^{1349}$ and $Tyr^{1356}$ in the multi-substrate docking site of Met was required for the transduction of downstream signals: $Tyr^{1349}$ was previously shown to be a binding site for the adapter protein Gab 1, whereas $Tyr^{1356}$ was primarily responsible for binding Grb2, PI3K, PLC-γ and SHP2 (reviewed in Furge et al., supra). Phospho-specific antibodies towards $Tyr^{1349}$ were used to determine whether DEP-1 dephosphorylated this site. In contrast to the gradual reduction in phosphorylation that was seen for the activation loop tyrosine residues, $Tyr^{1349}$ was nearly completely dephosphorylated in the presence of low levels of DEP-1 (FIG. 5B). This dephosphorylation also required DEP-1 catalytic activity since no change in the phosphorylation level of $Tyr^{1349}$ was observed in the presence of DEP-1(CS). In addition to the docking site tyrosine residues, other tyrosine residues have been shown to impact Met signaling. For example, $Tyr^{1365}$ was important for mediating a morphogenic signal (Weidner et al., (1995), supra). Phospho-specific antibodies directed towards this site revealed that $Tyr^{1365}$ was nearly completely dephosphorylated in the presence of low levels of DEP-1 (FIG. 5B).

Example 6

Effects of Increased DEP-1 Expression on the Interaction Between MET and GRB2

Figure 5C:
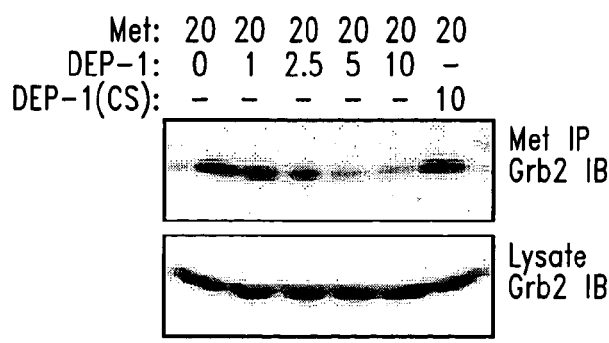

Ligand-induced activation of Met resulted in the recruitment of a number of proteins that were important for transmitting downstream signals. The dephosphorylation of a docking site tyrosine residue in Met, as detected in the preceding Examples, prompted examination of the recruitment of Grb2. Met was immunoprecipitated as described in Example 5 from serum-starved 293 cells co-expressing CSF-MET. Varying amounts of DEP-1 and the immunoprecipitates were probed for the presence of the Grb2 adapter protein. Grb2 was previously reported to bind to Met directly via $Tyr^{1365}$ (Fixman et al., supra; Ponzetto et al. (1994), supra). Immunoblots of cell lysates and MET-immunoprecipitates probed with an antibody specific for Grb2 (BD Transduction Labs) revealed that the level of Grb2 was not affected by the expression of DEP-1 and Met in these cells (FIG. 5C, lower blot). However, with increasing levels of DEP-1 a gradual decrease in the amount of Grb2 that co-immunoprecipitated with Met was observed (FIG. 5C, upper blot) coincident with the changes in overall tyrosine phosphorylation status of the PTK.

From the foregoing it will be appreciated that, although specific embodiments of the invention have been described herein for purposes of illustration, various modifications may be made without deviating from the spirit and scope of the invention.

What is claimed is:

1. A method of altering transduction of a biological signal in a cell, comprising:

introducing into a cell a density enchanced phospatase-1 (DEP-1) polypeptide that is capable of specific association with a DEP-1 substrate polypeptide under conditions and for a time sufficient to permit formation of a complex comprising the DEP-1 polypeptide in specific association with the DEP-1 substrate polypeptide, wherein:

(i) the DEP-1 polypeptide is selected from the group consisting of:

(a) a polypeptide which comprises the amino acid sequence set forth in SEQ ID NO:2, (b) a polypeptide which comprises the amino acid sequence set forth in SEQ ID NO:3, (c) a polypeptide that is encoded by a polynucleotide that hybridizes under moderately stringent conditions, wherein moderately stringent conditions comprise prewashing in a solution of 5×SSC, 0.5% SDS, 1.0 mM EDTA (pH 8.0) and hybridizing at 50° C.–70° C., 5×SSC, for 1–16 hours to a nucleic acid molecule which comprises a nucleotide sequence that is a reverse complement of SEQ ID NO:1, (d) a truncated DEP-1 polypeptide which comprises at least the amino acid sequence set forth at positions 1205–1245 of SEQ ID NO:2, (e) a mutant polypeptide which comprises at least one amino acid substitution in the amino acid sequence set forth in SEQ ID NO:2, wherein the amino acid substitution is selected from a substitution of aspartate at position 1205 and a substitution of cysteine at position 1239, (f) a mutant polypeptide according to (e) wherein aspartate at position 1205 is substituted with alanine, (g) a mutant polypeptide according to (e) wherein cysteine at position 1239 is substituted with serine, (h) a mutant polypeptide which comprises an amino acid sequence as set forth at positions 997–1337 of SEQ ID NO:2, said mutant polypeptide comprising at least one amino acid substitution that is selected from a substitution of aspartate at position 1205 and a substitution of cysteine at position 1239, (i) a mutant polypeptide according to (h) wherein aspartate at position 1205 is substituted with alanine, (j) a mutant polypeptide according to (h) wherein cysteine at position 1239 is substitute with serine, (k) a polypeptide that is encoded by a polynucleotide that hybridizes under moderately stringent conditions, wherein moderately stringent conditions comprise prewashing in a solution of 5×SSC, 0.5% SDS, 1.0 mM EDTA (pH 8.0) and hybridizing at 50° C.–70° C., 5×SSC, for 1–16 hours to a nucleic acid molecule which comprises a reverse complement of a nucleotide sequence that encodes a polypeptide selected from any one of (e)–(j), (l) a polypeptide to which binds an antibody that specifically recognizes a polypeptide that comprises the amino acid sequence set forth in SEQ ID NO:2, and (m) a polypeptide to which binds an antibody that specifically recognizes a polypeptide that comprises the amino acid sequence set forth in SEQ ID NO:3, and wherein (ii) the cell comprises a DEP-1 substrate polypeptide that is selected from the group consisting of
  (a) a polypeptide which comprises the amino acid sequence set forth in any one of SEQ ID NOS:4–6, and
  (b) a polypeptide comprising the amino acid sequence set forth in SEQ ID NO:7 which comprises a transmembrane domain and a cytoplasmic domain of the polypeptide of (a).

2. The method of claim 1 wherein the step of introducing comprises inducing expression of a polynucleotide that encodes the DEP-1 polypeptide, wherein said polynucleotide is present within the cell.

3. The method of claim 1 wherein the step of introducing comprises transforming or transfecting the cell with a recombinant expression construct that comprises a polynucleotide which encodes the DEP-1 polypeptide.

4. A method of altering transduction of a biological signal in a cell, comprising contacting a cell with an agent,
  (i) wherein the cell comprises a DEP-1 polypeptide and a DEP-1 substrate polypeptide, said DEP-1 polypeptide being capable of specific association with the DEP-1 substrate polypeptide to form a complex,
  (ii) wherein the agent is capable of altering the specific association of the DEP-1 polypeptide with the DEP-1 substrate polypeptide,
  (iii) wherein the DEP-1 polypeptide is selected from the group consisting of:
    (a) a polypeptide which comprises the amino acid sequence set forth in SEQ ID NO:2,
    (b) a polypeptide which comprises the amino acid sequence set forth in SEQ ID NO:3,
    (c) a polypeptide that is encoded by a polynucleotide that hybridizes under moderately stringent conditions, wherein moderately stringent conditions comprise prewashing in a solution of 5×SSC, 0.5% SDS, 1.0 mM EDTA (pH 8.0) and hybridizing at 50° C.–70° C., 5×SSC, for 1–16 hours to a nucleic acid molecule which comprises a nucleotide sequence that is a reverse complement of SEQ ID NO:1,
    (d) a truncated DEP-1 polypeptide which comprises at least the amino acid sequence set forth at positions 1205–1245 of SEQ ID NO:2,
    (e) a mutant polypeptide which comprises at least one amino acid substitution in the amino acid sequence set forth in SEQ ID NO:2, wherein the amino acid substitution is selected from a substitution of aspartate at position 1205 and a substitution of cysteine at position 1239,
    (f) a mutant polypeptide according to (e) wherein aspartate at position 1205 is substituted with alanine,
    (g) a mutant polypeptide according to (e) wherein cysteine at position 1239 is substituted with serine,
    (h) a mutant polypeptide which comprises an amino acid sequence as set forth at positions 997–1337 of SEQ ID NO:2, said mutant polypeptide comprising at least one amino acid substitution that is selected from a substitution of aspartate at position 1205 and a substitution of cysteine at position 1239,
    (i) a mutant polypeptide according to (h) wherein aspartate at position 1205 is substituted with alanine,
    (j) a mutant polypeptide according to (h) wherein cysteine at position 1239 is substitute with serine,
    (k) a polypeptide that is encoded by a polynucleotide that hybridizes under moderately stringent conditions, wherein moderately stringent conditions comprise prewashing in a solution of 5×SSC, 0.5% SDS, 1.0 mM EDTA (pH 8.0) and hybridizing at 50° C.–70° C., 5×SSC, for 1–16 hours to a nucleic acid molecule which comprises a reverse complement of a nucleotide sequence that encodes a polypeptide selected from any one of (e)–(j),
    (l) a polypeptide to which binds an antibody that specifically recognizes a polypeptide that comprises the amino acid sequence set forth in SEQ ID NO:2, and
    (m) a polypeptide to which binds an antibody that specifically recognizes a polypeptide that comprises the amino acid sequence set forth in SEQ ID NO:3, and
  (iv) wherein the DEP-1 substrate polypeptide is selected from the group consisting of
    (a) a polypeptide which comprises the amino acid sequence set forth in any one of SEQ ID NOS:4–6, and
    (b) a polypeptide comprising the amino acid sequence set forth in SEQ ID NO:7 which comprises a transmembrane domain and a cytoplasmic domain of the polypeptide of (a).

5. The method of either claim 1 or claim 4 wherein formation of the complex results in dephosphorylation of the DEP-1 substrate polypeptide.

6. The method of claim 5 wherein the DEP-1 substrate polypeptide is selected from the group consisting of (i) a polypeptide which comprises the amino acid sequence set forth in any one of SEQ ID NOS:4–6, and (ii) a polypeptide comprising the amino acid sequence set forth in SEQ ID NO:7 which comprises a transmembrane domain and a cytoplasmic domain of the polypeptide of (i), and wherein at least one phosphorylated amino acid selected from the group consisting of the amino acid corresponding to position 1349 of SEQ ID NO:4 and the amino acid corresponding to position 1365 of SEQ ID NO:4 is dephosphorylated.

7. The method of either claim 1 or claim 4 wherein transduction of the biological signal results in altered cell proliferation, differentiation or survival.

8. The method of either claim 1 or claim 4 wherein transduction of the biological signal results in altered cellular morphogenesis or altered cellular motility.

* * * * *

UNITED STATES PATENT AND TRADEMARK OFFICE
CERTIFICATE OF CORRECTION

| | | |
|---|---|---|
| PATENT NO. | : 7,205,121 B2 | Page 1 of 1 |
| APPLICATION NO. | : 10/723606 | |
| DATED | : April 17, 2007 | |
| INVENTOR(S) | : Helena L. Palka-Hamblin et al. | |

It is certified that error appears in the above-identified patent and that said Letters Patent is hereby corrected as shown below:

Title Page Two Item 56
Other Publications, first column, twentieth source, Keirsebilck, A. et al., "Molecular Cloning of the Huma p120$^{ctn}$ Catenin Gene (CTNNDI): Expression of Multiple Alternatively Spliced Isoforms.," should read -- Molecular Cloning of the Human p120$^{ctn}$ Catenin Gene (CTNND1): Expression of Multiple Alternatively Spliced Isoforms., --

Title Page Three Item 56
Other Publications, first column, fourteenth source, "Shulz" should read -- Shultz --

Other Publications, first column, sixteenth source, "Scottt" should read -- Scott --

Signed and Sealed this

First Day of April, 2008

JON W. DUDAS
*Director of the United States Patent and Trademark Office*